US011859015B2

(12) United States Patent
Scheinberg et al.

(10) Patent No.: US 11,859,015 B2
(45) Date of Patent: Jan. 2, 2024

(54) IMMUNOGENIC WT-1 PEPTIDES AND METHODS OF USE THEREOF

(71) Applicant: MEMORIAL SLOAN KETTERING CANCER CENTER, New York, NY (US)

(72) Inventors: David A. Scheinberg, New York, NY (US); Tao Dao, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 646 days.

(21) Appl. No.: 17/007,415

(22) Filed: Aug. 31, 2020

(65) Prior Publication Data

US 2020/0392183 A1 Dec. 17, 2020

Related U.S. Application Data

(60) Division of application No. 15/920,335, filed on Mar. 13, 2018, now Pat. No. 10,815,273, which is a continuation-in-part of application No. 14/760,997, filed as application No. PCT/US2014/011711 on Jan. 15, 2014, now Pat. No. 9,919,037.

(60) Provisional application No. 61/752,799, filed on Jan. 15, 2013.

(51) Int. Cl.

| | |
|---|---|
| ***C07K 7/06*** | (2006.01) |
| ***C07K 7/08*** | (2006.01) |
| ***A61K 38/10*** | (2006.01) |
| ***A61P 35/00*** | (2006.01) |
| ***A61K 38/08*** | (2019.01) |
| ***C07K 14/47*** | (2006.01) |
| ***A61K 45/06*** | (2006.01) |

(52) U.S. Cl.

CPC ................ *C07K 7/06* (2013.01); *A61K 38/08* (2013.01); *A61K 38/10* (2013.01); *A61K 45/06* (2013.01); *A61P 35/00* (2018.01); *C07K 7/08* (2013.01); *C07K 14/4748* (2013.01)

(58) Field of Classification Search

None

See application file for complete search history.

(56) References Cited

U.S. PATENT DOCUMENTS

| | | | |
|---|---|---|---|
| 5,229,115 | A | 7/1993 | Lynch |
| 5,622,835 | A | 4/1997 | Herlyn et al. |
| 5,633,142 | A | 5/1997 | Herlyn et al. |
| 5,726,288 | A | 3/1998 | Call et al. |
| 5,981,217 | A | 11/1999 | Subramaniam et al. |
| 6,156,316 | A | 12/2000 | Scheinberg et al. |
| 6,207,375 | B1 | 3/2001 | Subramaniam et al. |
| 6,316,599 | B1 | 11/2001 | Call et al. |
| 6,593,299 | B1 | 7/2003 | Bennett et al. |
| 6,805,861 | B2 | 10/2004 | Stauss |
| 6,861,234 | B1 | 3/2005 | Simard et al. |
| 7,030,212 | B1 | 4/2006 | Sugiyama et al. |
| 7,063,854 | B1 | 6/2006 | Gaiger et al. |
| 7,115,272 | B1 | 10/2006 | Gaiger et al. |
| 7,144,581 | B2 | 12/2006 | Gaiger et al. |
| 7,323,181 | B2 | 1/2008 | Gaiger et al. |
| 7,329,410 | B1 | 2/2008 | Gaiger et al. |
| 7,420,034 | B2 | 2/2008 | Sugiyama et al. |
| 7,368,119 | B2 | 5/2008 | Gaiger et al. |
| 7,488,718 | B2 | 2/2009 | Scheinberg et al. |
| 7,517,950 | B2 | 4/2009 | Sugiyama et al. |
| 7,553,494 | B2 | 6/2009 | Gaiger et al. |
| 7,597,894 | B2 | 10/2009 | Graddis et al. |
| 7,598,221 | B2 | 10/2009 | Scheinberg et al. |
| 7,608,685 | B1 | 10/2009 | Sugiyama et al. |
| 7,655,249 | B2 | 2/2010 | Gaiger et al. |
| 7,662,386 | B2 | 2/2010 | Gaiger et al. |
| 7,666,985 | B2 | 2/2010 | Sugiyama et al. |
| 7,745,391 | B2 | 6/2010 | Mintz et al. |
| 7,807,792 | B2 | 10/2010 | Sugiyama et al. |
| 7,833,775 | B2 | 11/2010 | Dubensky et al. |
| 7,901,693 | B2 | 3/2011 | Gaiger et al. |
| 7,915,393 | B2 | 3/2011 | Gaiger et al. |
| 7,939,627 | B2 | 5/2011 | Nishihara et al. |
| 8,071,732 | B2 | 12/2011 | Gaiger et al. |
| 8,105,604 | B2 | 1/2012 | Sugiyama |
| 8,216,595 | B2 | 7/2012 | Moon et al. |
| 8,288,355 | B2 | 10/2012 | Sugiyama et al. |
| 8,529,904 | B2 | 9/2013 | Stauss et al. |
| 8,557,247 | B2 | 10/2013 | Lemoine |
| 8,735,357 | B2 | 5/2014 | Sugiyama |
| 8,765,687 | B2 | 7/2014 | Scheinberg et al. |
| 8,771,702 | B2 | 7/2014 | Paterson et al. |

(Continued)

FOREIGN PATENT DOCUMENTS

| | | | |
|---|---|---|---|
| EP | 1447091 | A1 | 8/2004 |
| EP | 1536009 | | 6/2005 |

(Continued)

OTHER PUBLICATIONS

Bellantuono et al. "Two distinct HLA-A0201-presented epitopes of the Wilms tumor antigen 1 can function as targets for leukemia-reactive CTL" Blood. Nov. 15, 2012;100(10):3835-7.

Bergmann et al. "High levels of Wilms' tumor gene (wt1) mRNA in acute myeloid leukemias are associated with a worse long-term outcome" Blood. Aug. 1, 1997;90(3):1217-25.

Borbulevych et al. "Structures of native and affinity-enhanced WT1 epitopes bound to HLA-A* 0201: implications for WT1-based cancer therapeutics" Molecular Immunology. Sep. 30, 2010;47(15):2519-24.

Bruening et al. "A non-AUG translational initiation event generates novel WT1 isoforms" Journal of Biological Chemistry. Apr. 12, 1996;271(15):8646-54.

(Continued)

*Primary Examiner* — Daniel C Gamett

(74) *Attorney, Agent, or Firm* — Mark S. Cohen; PEARL COHEN ZEDEK LATZER BARATZ LLP

(57) ABSTRACT

This invention provides peptides, immunogenic compositions and vaccines, and methods of treating, reducing the incidence of, and inducing immune responses to a WT1-expressing cancer, comprising heteroclitic peptides derived from the WT-1 protein.

20 Claims, 6 Drawing Sheets

Specification includes a Sequence Listing.

(56) References Cited

U.S. PATENT DOCUMENTS

| | | | |
|---|---|---|---|
| 8,778,350 | B2 | 7/2014 | Sugiyama |
| 8,920,776 | B2 | 12/2014 | Gaiger et al. |
| 9,045,556 | B2 | 6/2015 | Udaka et al. |
| 9,181,302 | B2 | 11/2015 | Li et al. |
| 9,216,205 | B2 | 12/2015 | Chakraborty et al. |
| 9,226,955 | B2 | 1/2016 | Hilton et al. |
| 9,233,149 | B2 | 1/2016 | Scheinberg et al. |
| 9,248,173 | B2 | 2/2016 | Li et al. |
| 9,265,816 | B2 | 2/2016 | Scheinberg et al. |
| 9,266,932 | B2 | 2/2016 | Sugiyama |
| 9,272,026 | B2 | 3/2016 | Sugiyama |
| 9,403,886 | B2 | 8/2016 | Sugiyama |
| 9,499,602 | B2 | 11/2016 | Paterson et al. |
| 9,518,126 | B2 | 12/2016 | Kang et al. |
| 2002/0127718 | A1 | 9/2002 | Kuppner et al. |
| 2003/0032050 | A1 | 2/2003 | Berzofsky et al. |
| 2003/0045499 | A1 | 3/2003 | Gabrilovich et al. |
| 2003/0072761 | A1 | 4/2003 | Gaiger et al. |
| 2003/0082194 | A1 | 5/2003 | Scheinberg et al. |
| 2003/0175272 | A1 | 9/2003 | Gruenberg |
| 2004/0018204 | A1 | 1/2004 | Gaiger et al. |
| 2005/0002951 | A1 | 1/2005 | Sugiyama et al. |
| 2005/0119185 | A1 | 6/2005 | Scheinberg et al. |
| 2005/0147621 | A1 | 7/2005 | Higgins et al. |
| 2005/0214268 | A1 | 9/2005 | Cavanaugh et al. |
| 2005/0221481 | A1 | 10/2005 | Migliaccio et al. |
| 2005/0260217 | A1 | 11/2005 | Johnson et al. |
| 2006/0057130 | A1 | 3/2006 | Nair et al. |
| 2006/0083716 | A1 | 4/2006 | Kaufman et al. |
| 2006/0084609 | A1 | 4/2006 | Scheinberg et al. |
| 2006/0165708 | A1 | 7/2006 | Mayumi et al. |
| 2007/0082860 | A1 | 4/2007 | Sugiyama et al. |
| 2007/0128207 | A1 | 6/2007 | Sugiyama et al. |
| 2007/0298093 | A1 | 12/2007 | Kanur et al. |
| 2008/0070835 | A1 | 3/2008 | Sugiyama et al. |
| 2009/0143291 | A1 | 6/2009 | Sugiyama et al. |
| 2010/0034842 | A1 | 2/2010 | Graddis et al. |
| 2010/0040614 | A1 | 2/2010 | Ahmed et al. |
| 2010/0092522 | A1 | 4/2010 | Scheinberg et al. |
| 2010/0111986 | A1 | 5/2010 | Scheinberg et al. |
| 2010/0166738 | A1 | 7/2010 | Gaiger et al. |
| 2010/0247556 | A1 | 9/2010 | Sugiyama |
| 2011/0070251 | A1 | 3/2011 | Sugiyama et al. |
| 2011/0136141 | A1 | 6/2011 | Adamczyk et al. |
| 2011/0223187 | A1 | 9/2011 | Shahabi et al. |
| 2011/0287055 | A1 | 11/2011 | Lauer et al. |
| 2011/0318380 | A1 | 12/2011 | Brix et al. |
| 2012/0301492 | A1 | 11/2012 | Gaiger et al. |
| 2013/0064812 | A1 | 3/2013 | Gallatin et al. |
| 2013/0196427 | A1 | 8/2013 | Sugiyama |
| 2013/0243800 | A1 | 9/2013 | Sugiyama |
| 2013/0266958 | A1 | 10/2013 | Sugiyam et al. |
| 2014/0086831 | A1 | 3/2014 | Scheinberg et al. |
| 2014/0179004 | A1 | 6/2014 | Fujii et al. |
| 2014/0220055 | A1 | 8/2014 | Okubo et al. |
| 2014/0220057 | A1 | 8/2014 | Okubo et al. |
| 2014/0220059 | A1 | 8/2014 | Asari et al. |
| 2014/0220105 | A1 | 8/2014 | Maeda et al. |
| 2014/0255941 | A1 | 9/2014 | Sugiyama |
| 2014/0271693 | A1 | 9/2014 | Nakatani |
| 2014/0341939 | A1 | 11/2014 | Udaka |
| 2015/0030533 | A1 | 1/2015 | Algate et al. |
| 2015/0118208 | A1 | 4/2015 | Schmitt et al. |
| 2015/0150975 | A1 | 6/2015 | Tanka et al. |
| 2015/0328278 | A1 | 11/2015 | Kubo et al. |
| 2015/0329874 | A1 | 11/2015 | Fukumura et al. |
| 2015/0352201 | A1 | 12/2015 | Scheinberg et al. |
| 2015/0368612 | A1 | 12/2015 | Palucka et al. |
| 2016/0058852 | A1 | 3/2016 | Ter Meulen et al. |
| 2016/0058854 | A1 | 3/2016 | Bender et al. |
| 2016/0068801 | A1 | 3/2016 | Lubenau |
| 2016/0084841 | A1 | 3/2016 | Sugiyam et al. |
| 2016/0030536 | A1 | 4/2016 | Weiner et al. |
| 2016/0114017 | A1 | 4/2016 | Okada |
| 2016/0114019 | A1 | 4/2016 | Li et al. |
| 2016/0166665 | A1 | 6/2016 | Ito |
| 2016/0176939 | A1 | 6/2016 | Sugiyama |
| 2016/0201141 | A1 | 7/2016 | Albitar et al. |
| 2016/0280756 | A1 | 9/2016 | Smith et al. |
| 2016/0317634 | A1 | 11/2016 | Springer et al. |
| 2016/0362465 | A1 | 12/2016 | Nishimura et al. |
| 2016/0367649 | A1 | 12/2016 | Sugiyama |
| 2016/0368948 | A1 | 12/2016 | Scheinberg et al. |
| 2017/0007693 | A1 | 1/2017 | Weinder et al. |
| 2017/0072038 | A1 | 3/2017 | Sugiyam et al. |

FOREIGN PATENT DOCUMENTS

| | | | |
|---|---|---|---|
| EP | 1696027 | | 8/2006 |
| EP | 1961761 | A1 | 8/2008 |
| EP | 2070947 | A1 | 6/2009 |
| EP | 2228072 | A1 | 9/2010 |
| EP | 2338509 | A2 | 6/2011 |
| EP | 2762156 | A1 | 8/2014 |
| EP | 2762159 | A1 | 8/2014 |
| EP | 2565201 | B1 | 11/2014 |
| EP | 1951281 | B1 | 4/2015 |
| EP | 2010209 | B1 | 6/2015 |
| EP | 2933261 | A1 | 10/2015 |
| EP | 2119778 | B1 | 11/2015 |
| EP | 2982681 | A1 | 2/2016 |
| EP | 2998740 | A1 | 3/2016 |
| EP | 2283112 | B1 | 10/2016 |
| EP | 3112378 | A1 | 1/2017 |
| EP | 3117836 | A1 | 1/2017 |
| WO | WO 1995/029240 | | 11/1995 |
| WO | WO 1996/035438 | A1 | 11/1996 |
| WO | WO 1997/011091 | | 3/1997 |
| WO | WO 1999/038973 | A2 | 8/1999 |
| WO | WO 2000/006602 | | 2/2000 |
| WO | WO 2000/026249 | A1 | 5/2000 |
| WO | WO 2000/037491 | | 6/2000 |
| WO | WO 2000/055351 | | 9/2000 |
| WO | WO 2001025273 | A2 | 4/2001 |
| WO | WO 2001/062920 | | 8/2001 |
| WO | WO 2002/028414 | A1 | 4/2002 |
| WO | WO 2003/037060 | A2 | 5/2003 |
| WO | WO 2004/111075 | A2 | 12/2004 |
| WO | WO 2005/053618 | | 6/2005 |
| WO | WO 2007/047764 | A2 | 4/2007 |
| WO | WO 2007/120673 | | 10/2007 |
| WO | WO 2010037395 | A2 | 4/2010 |
| WO | WO 2014/113490 | | 7/2014 |
| WO | WO 2016/093326 | A1 | 6/2016 |
| WO | WO 2016/208332 | | 12/2016 |
| WO | WO 2017/049074 | | 3/2017 |

OTHER PUBLICATIONS

Buzyn et al. Peptides derived from the whole sequence of BCR-ABL bind to several class I molecules allowing specific induction of human cytotoxic T lymphocytes European journal of immunology. Aug. 1, 1997;27(8):2066-72.

Call et al. "Isolation and characterization of a zinc finger polypeptide gene at the human chromosome 11 Wilms' tumor locus" Cell. Feb. 9, 1990;60(3):509-20.

Cathcart et al. "All CML patients vaccinated with a multivalent bcr-abl peptide vaccine show specific immune responses in a phase II trial" Blood, 2001. 98(11): p. 728a-728a.

Cathcart et al. "A multivalent bcr-abl fusion peptide vaccination trial in patients with chronic myeloid leukemia". Blood. Feb. 1, 2004;103(3):1037-42.

Cheever et al. "The prioritization of cancer antigens: a national cancer institute pilot project for the acceleration of translational research" Clinical Cancer Research. Sep. 1, 2009;15(17):5323-37.

Chen et al. "Expression patterns of WT-1 and Bcr-Abl measured by TaqMan quantitative real-time RT-PCR during follow-up of leukemia patients with the Ph chromosome" Chinese medical journal. Jul. 2004;117(7):968-71.

Cilloni et al. "Significant correlation between the degree of WT-1 expression and the International Prognostic Scoring System Score

(56) References Cited

OTHER PUBLICATIONS in patients with myelodysplastic syndromes" J Clin Oncol. 2003;21(10):1988-1995.
Clay et al. "Changes in the fine specificity of gp100 (209-217)-reactive T cells in patients following vaccination with a peptide modified at an HLA-A2. 1 anchor residue". The Journal of Immunology. Feb. 1, 1999;162(3):1749-55.
Dao et al. "An immunogenic WT1-derived peptide that induces T cell response in the context of HLA-A* 02: 01 and HLA-2* 24: 02 molecules" OncoImmunology. Feb. 1, 2017;6(2):e1252895.
Database Biosis [Online], Biosicience Information Service; Pirilla Javier, Breaking tolerance to the bcr/abl.
Database Biosis [online]; Nov. 16, 2003, pinilla Javier et al. "Breaking tolerance to the bcr/abl p201 b2a2 protein by use of mutated, heterocitic breakpoint peptides"; Database accession No. PREV200400147743, Abstract; and Blood vol. 102 No. 11, Nov. 16, 2003, p. 654a, 45th annual meeting of the American Society of Hematology, Dec. 6-9, 2003.
Database Bisis [online]; Nov. 16, 2003, Pinilla Javier et al. "Breaking tolerance to the bcr/abl p201 b2a2 protein by use of mutated, heterocitic breakpoint peptides"; Database accession No. PREV200400147740, Abstract; and Blood vol. 102 No. 11, Nov. 16, 2003, p. 654a, 45th annual meeting of the American Society of Hematology, Dec. 6-9, 2003.
De Groot et al. "An interactive Web site providing major histocompatibility ligand predictions: application to HIV research" AIDS research and human retroviruses. May 1, 1997;13(7):529-31.
Doubrovina et al. "In vitro stimulation with WT1 peptide-loaded Epstein-Barr virus-positive B cells elicits high frequencies of WT1 peptid-specific T cells with in vitro and in vivo tumoricidal activity" Clinical Cancer Research. Nov. 1, 2004;10(21):7207-19.
Doubrovina et al. "Sensitization of Human T Cells with Overlapping Pentadecapeptides Spanning the Wt1 Protein Induces Expansion of Leukemocidal T Cells Specific for Both Previously Identified and Novel WT1 Epitopes" Blood. Nov. 16, 2004;104(11):3873-.
Doubrovina et al. "Generation of T Cells of Desired HLA Restriction Specific for Epitopes of a Self-Antigen, WT1, for the Adoptive Immunotherapy of WT1 Positive Malignancies Using A Panel of Artificial Antigen Presenting Cells Expressing Prevalent HLA Alleles" Blood. Nov. 20, 2009;114(22):4086-.
Doubrovina et al. "Leukemia-Reactive Cytotoxic CD8+ and CD4+ T-Cells Specific for Novel WT-1 Epitopes Are Generated in Vitro by Sensitization With Overlapping Pentadecapeptides (15-MERS) Spanning the Wilms Tumor Protein" Blood. Nov. 16, 2007;110(11):1810-.
Dyall et al. "Heteroclitic immunization induces tumor immunity" Journal of Experimental Medicine. Nov. 2, 1998;188(9):1553-61.
Elisseeva et al. "Humoral immune responses against Wilms tumor gene WT1product in patients with hematopoieitc malignancies" Blood. May 1, 2002;99(9):3272-9.
Ellisen et al. "The Wilms tumor suppressor WT1 directs stage-specific quiescence and differentiation of human hematopoietic progenitor cells" The EMBO Journal. Apr. 17, 2001;20(8):1897-909.
Fujiki et al. "A WT1 protein-derived, naturally processed 16-mer peptide, WT1332, is a promiscuous helper peptide for induction of WT1-specific Th1-type CD4+ T cells" Microbiology and immunology. Dec. 1, 2008;52(12):591-600.
Gaiger et al. "Immunity to WT1 in the animal model and in patients with acute myeloid leukemia" Blood. Aug. 15, 2000;96(4):1480-9.
Gao et al. "Human cytotoxic T lymphocytes specific for Wilms' tumor antigen-1 inhibit engraftment of leukemia-initiating stem cells in non-obese diabetic-severe combined immunodeficient recipients" Transplantation. May 15, 2003;75(9):1429-36.
Gao e al. "Selective elimination of leukemic CD34+ progenitor cells by cytotoxic T lymphocytes specific for WT1" Blood. Apr. 1, 2000;95(7):2198-203.
Gao et al. "Antigen-specific CD4+ T-cell help is required to activate a memory CD8+ T cell to a fully functional tumor killer cell" Cancer research. Nov. 15, 2002;62(22):6438-41.
Gerber et al. "Characterization of chronic myeloid leukemia stem cells" American journal of hematology. Jan. 1, 2011;86(1):31-7.
Gessler et al. Homozygous deletion in Wilms tumours of a zinc-finger gene identified by chromosome jumping. Nature. Feb. 22, 1990;343(6260):774.
Gillmore et al. "Detection of Wilms' tumor antigen-specific CTL in tumor-draining lymph nodes of patients with early breast cancer" Clinical Cancer Research. Jan. 1, 2006;12(1):34-42.
Graff-Dubois et al. "Generation of CTL recognizing an HLA-A* 0201-restricted epitope shared by MAGE-A1,-A2,-A3,-A4,-A6,-A10, and-A12 tumor antigens: implication in a broad-spectrum tumor immunotherapy" The Journal of Immunology. Jul. 1, 2002;169(1):575-80.
Greco et al. "Two-brc-abl junction peptides bind HLA-A3 molecules and allow specific induction of human cytotoxic T lymphocytes". Leukemia. Apr. 1996;10(4):693-9.
Greiner et al. "Leukemia-associated antigens are critical for the proliferation of acute myeloid leukemia cells" Clinical Cancer Research. Nov. 15, 2008;14(22):7161-6.
Haber et al. "Alternative splicing and genomic structure of the Wilms tumor gene WT1" Proceedings of the National Academy of Sciences. Nov. 1, 1991;88(21):9618-22.
Healthline.om, "Non-hodgkin's Lymphoma: In Depth-Overview", pp. 1-3, http://www.healthline.com/channel/non-hodgkins-lymphoma indepth-overview, Dec. 2, 2008.
Hosen et al. "Very low frequencies of human normal CD34+ haematopoietic progenitor cells express the Wilms' tumour gene WT1 at levels similar to those in leukaemia cells" British journal of haematology. Feb. 1, 2002;116(2):409-20.
Ibrahim et al. "Identification of a distinct antibacterial domain within the N-lobe of ovotransferrin" Biochimica et Biophysica Acta (BBA)-Molecular Cell Research. Mar. 5, 1998;1401(3):289-303.
International Search Report for PCT application No. PCTUS1411711 dated Aug. 5, 2014.
Kaida et al. "Phase 1 trial of Wilms tumor 1 (WT1) peptide vaccine and gemcitabine combination therapy in patients with advanced pancreatic or biliary tract cancer" Journal of Immunotherapy. Jan. 1, 2011;34(1):92-9.
Keilholz et al. "A clinical and immunologic phase 2 trial of Wilms tumor gene product 1 (WT1) peptide vaccination in patients with AML and MDS" Blood. Jun. 25, 2009;113(26):6541-8.
Kelly et al. "Lung Cancer—Vaccines" Cancer journal (Sudbury, Mass.). Sep. 2011;17(5):302.
Kessler et al. "Effects of Epitope Modification on T Cell Receptor—Ligand Binding and Antigen Recognition by Seven H-2Kd-restricted Cytotoxic T Lymphocyte Clones Specific for a Photoreactive Peptide Derivative" Journal of Experimental Medicine. Feb. 17, 1997;185(4):629-40.
Kiecker et al. "Analysis of antigen-specific T-cell responses with synthetic peptides—what kind of peptide for which purpose?" Human Immunology. May 31, 2004;65(5):523-36.
King et al. "IL15 can reverse the unresponsiveness of Wilms' tumor antigen-specific CTL in patients with prostate cancer" Clinical cancer research. Feb. 15, 2009;15(4):1145-54.
Kobayashi et al. "Defining MHC class II T helper epitopes for WT1 tumor antigen" Cancer Immunology, Immunotherapy. Jul. 1, 2006;55(7):850-60.
Kreidberg et al. "WT-1 is required for early kidney development" Cell. Aug. 27, 1993;74(4):679-91.
Krug et al. "WT1 peptide vaccinations induce CD4 and CD8 T cell immune responses in patients with mesothelioma and non-small cell lung cancer." Cancer immunology, immunotherapy 59.10 (2010): 1467-1479.
Lapillonne et al. "High WT1 expression after induction therapy predicts high risk of relapse and death in pediatric acute myeloid leukemia" Journal of Clinical Oncology. Apr. 1, 2006;24(10):1507-15.
Lehe et al. "The Wilms' tumor antigen is a novel target for human CD4+ regulatory T cells: implications for immunotherapy" Cancer Research. Aug. 1, 2008;68(15):6350-9.

(56) References Cited

OTHER PUBLICATIONS

Maslak et al. "Vaccination with synthetic analog peptides derived from WT1 oncoprotein induces T-cell responses in patients with complete remission from acute myeloid leukemia." Blood 116.2 (2010): 171-179.
May et al. "Peptide epitopes from the Wilms' tumor 1 oncoprotein stimulate CD4+ and CD8+ T cells that recognize and kill human malignant mesothelioma tumor cells" Clinical Cancer Research. Aug. 1, 2007;13(15):4547-55.
McKee et al. "T cell avidity and tumor recognition: implications and therapeutic strategies" Journal of translational medicine. Sep. 20, 2005;3(1):35.
Meister et al. "Two novel T cell epitope prediction algorithms based on MHC-binding motifs; comparison of predicted and published epitopes from *Mycobacterium tuberculosis* and HIV protein sequences" Vaccine. Jan. 1, 1995;13(6):581-91.
Menssen et al. "Wilms' tumor gene (WT1) expression in lung cancer, colon cancer and glioblastoma cell lines compared to freshly isolated tumor specimens" Journal of cancer research and clinical oncology. Mar. 4, 2000;126(4):226-32.
Murao et al. "High frequencies of less differentiated and more proliferative WT1-specific CD8+ T cells in bone marrow in tumor-bearing patients: An important role of bone marrow as a secondary lymphoid organ" Cancer science. Apr. 1, 2010;101(4):848-54.
Nicholson et al. "Heteroclitic proliferative responses and changes in cytokine profile induced by altered peptides: implications for autoimmunity". Proceedings of the National Academy of Sciences. Jan. 6, 1998;95(1):264-9.
Nieda et al. "Dendritic cells stimulate the expansion of bcr-abl specific CD8+ T cells with cytotoxic activity against leukemic cells from patients with chronic myeloid leukemia". Blood, 1998. 91(3): p. 977-983.
Ochsenreither et al. "Wilms' tumor protein 1 (WT1) peptide vaccination in AML patients: predominant TCR CDR3β sequence associated with remission in one patient is detectable in other vaccinated patients" Cancer Immunology, Immunotherapy. Mar. 1, 2012;61(3):313-22.
Ohminami et al. "HLA class I-restricted lysis of leukemia cells by a CD8+ cytotoxic T-lymphocyte clone specific for WT1 peptide" Blood. Jan. 1, 2000;95(1):286-93.
Oka et al. "Human cytotoxic T-lymphocyte responses specific for peptides of the wild-type Wilms' tumor gene (WT1) product" Immunogenetics. Feb. 16, 2000;51(2):99-107.
Oka et al. "Induction of WT1 (Wilms' tumor gene)-specific cytotoxic T lymphocytes by WT1 peptide vaccine and the resultant cancer regression" Proceedings of the National Academy of Sciences of the United States of America. Sep. 21, 2004;101(38):13885-90.
Oka et al. "Cancer Immunotherapy targeting Wilms' tumor gene WT1 product" The Journal of Immunology. Feb. 15, 2000;164(4):1873-80.
Parkhurst et al. "Improved induction of melanoma-reactive CTL with peptides from the melanoma antigen gp100 modified at HLA-A* 0201-binding residues" The Journal of Immunology. Sep. 15, 1996;157(6):2539-48.
Parmiani et al. "Cancer immunotherapy with peptide-based vaccines: what have we achieved? Where are we going?" Journal of the National Cancer Institute. Jun. 5, 2002;94(11):805-18.
Pinilla-Ibarz et al. "Improved human T-cell responses against synthetic HLA-0201 analog peptides derived from the WT1 oncoprotein" Leukemia. Nov. 1, 2006;20(11):2025-33.
Pinilla-Ibarz et al. "Synthetic peptide analogs derived from bcr/abl fusion proteins and the induction of heteroclitic human T-cell responses" Haematologica. Jan. 1, 2005;90(10):1324-32.
Pinalla-Ibarz et al. "Vaccination of patients with chronic myelogenous leukemia with bcr-abl oncogene breakpoint fusion peptides generates specific immune responses" Blood. Mar. 1, 2000;95(5):1781-7.
Pinilla-Ibarz et al. "Synthetic analogue bcr/abl fusion peptides improve class I immunogenicity to the native protein" InBlood Nov. 16, 2000 (vol. 96, No. 11, pp. 510A-510A).
Pospori et al. "Specificity for the tumor-associated self-antigen WT1 drives the development of fully functional memory T cells in the absence of vaccination" Blood. Jun. 23, 2011;117(25):6813-24.
Rammensee eet al. "MHC ligands and peptide motifs: first listing" Immunogenetics. Feb. 1, 1995;41(4):178-228.
Rezvani et al. "Leukemia-associated antigen-specific T-cell responses following combined PR1 and WT1 peptide vaccination in patients with myeloid malignancies" Blood. Jan. 1, 2008;111(1):236-42.
Rezvani et al.Repeated PR1 and WT1 peptide vaccination in Montanide-adjuvant fails to induce sustained high-avidity, epitope-specific CD8+ T cells in myeloid malignancies. Haematologica. Mar. 1, 2011;96(3):432-40.
Rezvani et al. "T-cell responses directed against multiple HLA-A* 0201-restricted epitopes derived from Wilms' tumor 1 protein in patients with leukemia and healthy donors: identification, quantification, and characterization" Clinical Cancer Research. Dec. 15, 2005;11(24):8799-807.
Rosenberg et al. "Immunologic and therapeutic evaluation of a synthetic peptide vaccine for the treatment of patients with metastatic melanoma". Nature medicine. Mar. 1998;4(3):321.
Scardino et al. "HER-2/neu and hTERT cryptic epitopes as novel targets for broad spectrum tumor immunotherapy". The Journal of Immunology. Jun. 1, 2002;168(11):5900-6.
Scharnhorst et al. "WT1 proteins: functions in growth and differentiation" Gene. Aug. 8, 2001;273(2):141-61.
Scheibenbogen et al. "CD8 T-cell responses to Wilms tumor gene product WT1 and proteinase 3 in patients with acute myeloid leukemia" Blood. Sep. 15, 2002;100(6):2132-7.
Slansky et al. "Enhanced antigen-specific antitumor immunity with altered peptide ligands that stabilize the MHC-peptide-TCR complex". Immunity. Oct. 1, 2000;13(4):529-38.
Sloand et al. "T-cell immune responses to Wilms tumor 1 protein in myelodysplasia responsive to immunosuppressive therapy" Blood. Mar. 3, 2011;117(9):2691-9.
Smithgall et al. "Identification of a novel WT1 HLA A* 0201-restricted CTL epitope using whole gene in vitro priming" In Blood Nov. 16, 2001 (vol. 98, No. 11, pp. 121A-121A).
Sugiyama H. "WT1 (Wilms' tumor gene 1): biology and cancer immunotherapy" Japanese journal of clinical oncology. Apr. 15, 2010:hyp194.
Supplementary European Search Report for European Application No. 14741142.5 dated Oct. 7, 2016.
Tamaki et al. "The Wilms' tumor gene WT1 is a good marker for diagnosis of disease progression of myelodyspinstic syndromes" Leukemia. Mar. 1, 1999;13:393-9.
Tatsumi et al. "Wilms' tumor gene WT1-shRNA as a potent apoptosis-inducing agent for solid tumors" International journal of oncology. Mar. 1, 2008;32(3):701-12.
Ten Bosch et al. "A BCR-ABL oncoprotein p210b2a2 fusion region sequence is recognized by HLA-DR2a restricted cytotoxic T lymphocytes and presented by HLA-DR matched cells transfected with an II(b2a2) construct" Blood, 1999. 94(3): p. 1038-1045.
The MGC project Team: UniProt Accession Q6PI38; Dec. 14, 2011; [online]; available on the internet: http://www.uniprot.org/uniprot/Q6PI38.txt?version=42; downloaded on May 7, 2013.
Tourdot et al. "A general strategy to enhance immunogenicity of low-affinity HLA-A2. 1-associated peptides: implication in the identification of cryptic tumor epitopes" European journal of immunology. Dec. 1, 2000;30(12):3411-21.
Trojan et al. "Generation of cytotoxic T lymphocytes against native and altered peptides of human leukocyte antigen-A* 0201 restricted epitopes from the human epithelial cell adhesion molecule" Cancer research. Jun. 15, 2001;61(12):4761-5.
Tsuboi et al. "Cytotoxic T-lymphocyte responses elicited to Wilms' tumor gene WT1 product by DNA vaccination" Journal of clinical immunology. May 1, 2000;20(3):195-202.
Tyler et al. "WT1-specific immune responses in patients with high-risk multiple myeloma undergoing allogeneic T cell-depleted hematopoietic stem cell transplantation followed by donor lymphocyte infusions" Blood. Nov. 18, 2011;118(21):1993-.
Valmori et al. "Optimal activation of tumor-reactive T cells by selected antigenic peptide analogues" International immunology. Dec. 1, 1999;11(12):1971-80.

(56) References Cited

OTHER PUBLICATIONS

Watson et al. "A prophylactic vaccine for breast cancer?" Breast Cancer Research. Aug. 31, 2010;12(4):310.
Weber et al. "WT1 peptide-specific T cells generated from peripheral blood of healthy donors: possible implications for adoptive immunotherapy after allogeneic stem cell transplantation" Leukemia. Sep. 1, 2009;23(9):1634-42.
Xue et al. "Elimination of human leukemia cells in NOD/SCID mice by WT1-TCR gene-transduced human T cells" Blood. Nov. 1, 2005;106(9):3062-7.
Yang et al. "A tumor suppressor and oncogene: the WT1 story" Leukemia. May 1, 2007;21(5):868-76.
Yotnda et al. "Cytotoxic T cell response against the chimeric p210 BCR-ABL protein in patients with chronic myelogenous leukemia" Journal of Clinical Investigation. May 15, 1998;101(10):2290.
Yu et al. "Methods for prediction of peptide binding to MHC molecules: a comparative study" Molecular Medicine. Mar. 2002;8(3):137.
Zhang et al. "Advances in dendritic cell-based vaccine of cancer" Cancer Biotherapy and Radiopharmaceuticals. Dec. 1, 2002;17(6):601-19.
Zügel et al. "Termination of peripheral tolerance to a T cell epitope by heteroclitic antigen analogues". The Journal of Immunology. Aug. 15, 1998;161(4):1705-9.
Doubrovina Ekaterina et al. "Mapping of Novel Peptides of WT-1 and Presenting HLA Alleles That Induce Epitope-Specific HLA-Restricted T Cells With Cytotoxic Activity Against WT-1 (+) Leukemias.", Blood Aug. 23, 2012, vol. 120, No. 8, Aug. 23, 2012, pp. 1633-1646.
European Search Report dated Jan. 14, 2021 for Corresponding EP Application 20193303.3.
Office Action dated Jan. 12, 2022 for Corresponding Canadian Application No. 2,898,099.

SEQUENCE LISTING

<160> NUMBER OF SEQ ID NOS: 62

<210> SEQ ID NO 1
<211> LENGTH: 9
<212> TYPE: PRT
<213> ORGANISM: Human

<400> SEQUENCE: 1

```
Thr Tyr Ser Val Ser Phe Asp Ser Leu
1               5


<210> SEQ ID NO 2
<211> LENGTH: 9
<212> TYPE: PRT
<213> ORGANISM: Human

<400> SEQUENCE: 2

Gln Leu Gln Asn Pro Ser Tyr Asp Lys
1               5


<210> SEQ ID NO 3
<211> LENGTH: 15
<212> TYPE: PRT
<213> ORGANISM: Human

<400> SEQUENCE: 3

Gly Val Cys Val Cys Gly Asp Glu Asn Ile Leu Val Gln Glu Phe
1               5                   10                  15


<210> SEQ ID NO 4
<211> LENGTH: 9
<212> TYPE: PRT
<213> ORGANISM: Human

<400> SEQUENCE: 4

Asn Gln Met Asn Leu Gly Ala Thr Leu
1               5


<210> SEQ ID NO 5
<211> LENGTH: 9
<212> TYPE: PRT
<213> ORGANISM: Human

<400> SEQUENCE: 5

Asn Gln Met Asn Leu Gly Ala Thr Leu
1               5


<210> SEQ ID NO 6
<211> LENGTH: 9
<212> TYPE: PRT
<213> ORGANISM: Human

<400> SEQUENCE: 6

Asn Leu Met Asn Leu Gly Ala Thr Leu
1               5


<210> SEQ ID NO 7
<211> LENGTH: 9
<212> TYPE: PRT
<213> ORGANISM: Human

<400> SEQUENCE: 7

Asn Tyr Met Asn Leu Gly Ala Thr Leu
1               5


<210> SEQ ID NO 8
<211> LENGTH: 15
<212> TYPE: PRT
<213> ORGANISM: Human

<400> SEQUENCE: 8

Cys Met Thr Trp Asn Gln Met Asn Leu Gly Ala Thr Leu Lys Gly
1               5                   10                  15
```

<210> SEQ ID NO 9
<211> LENGTH: 15
<212> TYPE: PRT
<213> ORGANISM: Human

<400> SEQUENCE: 9

```
Trp Asn Gln Met Asn Leu Gly Ala Thr Leu Lys Gly Val Ala Ala
1               5                   10                  15
```

<210> SEQ ID NO 10
<211> LENGTH: 15
<212> TYPE: PRT
<213> ORGANISM: Human

<400> SEQUENCE: 10

```
Cys Met Thr Trp Asn Tyr Met Asn Leu Gly Ala Thr Leu Lys Gly
1               5                   10                  15
```

<210> SEQ ID NO 11
<211> LENGTH: 15
<212> TYPE: PRT
<213> ORGANISM: Human

<400> SEQUENCE: 11

```
Trp Asn Tyr Met Asn Leu Gly Ala Thr Leu Lys Gly Val Ala Ala
1               5                   10                  15
```

<210> SEQ ID NO 12
<211> LENGTH: 15
<212> TYPE: PRT
<213> ORGANISM: Human

<400> SEQUENCE: 12

```
Met Thr Trp Asn Gln Met Asn Leu Gly Ala Thr Leu Lys Gly Val
1               5                   10                  15
```

<210> SEQ ID NO 13
<211> LENGTH: 15
<212> TYPE: PRT
<213> ORGANISM: Human

<400> SEQUENCE: 13

```
Thr Trp Asn Gln Met Asn Leu Gly Ala Thr Leu Lys Gly Val Ala
1               5                   10                  15
```

<210> SEQ ID NO 14
<211> LENGTH: 15
<212> TYPE: PRT
<213> ORGANISM: Human

<400> SEQUENCE: 14

```
Cys Met Thr Trp Asn Leu Met Asn Leu Gly Ala Thr Leu Lys Gly
1               5                   10                  15
```

<210> SEQ ID NO 15
<211> LENGTH: 15
<212> TYPE: PRT
<213> ORGANISM: Human

<400> SEQUENCE: 15

```
Met Thr Trp Asn Leu Met Asn Leu Gly Ala Thr Leu Lys Gly Val
1               5                   10                  15
```

<210> SEQ ID NO 16
<211> LENGTH: 15
<212> TYPE: PRT
<213> ORGANISM: Human

<400> SEQUENCE: 16

Thr Trp Asn Leu Met Asn Leu Gly Ala Thr Leu Lys Gly Val Ala
1 5 10 15

<210> SEQ ID NO 17
<211> LENGTH: 15
<212> TYPE: PRT
<213> ORGANISM: Human

<400> SEQUENCE: 17

Trp Asn Leu Met Asn Leu Gly Ala Thr Leu Lys Gly Val Ala Ala
1 5 10 15

<210> SEQ ID NO 18
<211> LENGTH: 9
<212> TYPE: PRT
<213> ORGANISM: Human

<400> SEQUENCE: 18

Met Asn Leu Gly Ala Thr Leu Lys Gly
1 5

<210> SEQ ID NO 19
<211> LENGTH: 15
<212> TYPE: PRT
<213> ORGANISM: Human

<400> SEQUENCE: 19

Met Thr Trp Asn Tyr Met Asn Leu Gly Ala Thr Leu Lys Gly Val
1 5 10 15

<210> SEQ ID NO 20
<211> LENGTH: 15
<212> TYPE: PRT
<213> ORGANISM: Human

<400> SEQUENCE: 20

Thr Trp Asn Tyr Met Asn Leu Gly Ala Thr Leu Lys Gly Val Ala
1 5 10 15

<210> SEQ ID NO 21
<211> LENGTH: 17
<212> TYPE: PRT
<213> ORGANISM: Human

<400> SEQUENCE: 21

Cys Met Thr Trp Asn Gln Met Asn Leu Gly Ala Thr Leu Lys Gly Val
1 5 10 15

Ala

<210> SEQ ID NO 22
<211> LENGTH: 17
<212> TYPE: PRT
<213> ORGANISM: Human

<400> SEQUENCE: 22

Cys Met Thr Trp Asn Leu Met Asn Leu Gly Ala Thr Leu Lys Gly Val
1 5 10 15

Ala

<210> SEQ ID NO 23
<211> LENGTH: 17
<212> TYPE: PRT
<213> ORGANISM: Human

<400> SEQUENCE: 23

```
Cys Met Thr Trp Asn Tyr Met Asn Leu Gly Ala Thr Leu Lys Gly Val
1               5                   10                  15

Ala
```

<210> SEQ ID NO 24
<211> LENGTH: 9
<212> TYPE: PRT
<213> ORGANISM: Human

<400> SEQUENCE: 24

```
Trp Asn Gln Met Asn Leu Gly Ala Thr
1               5
```

<210> SEQ ID NO 25
<211> LENGTH: 9
<212> TYPE: PRT
<213> ORGANISM: Human

<400> SEQUENCE: 25

```
Trp Asn Gln Met Asn Leu Gly Ala Thr
1               5
```

<210> SEQ ID NO 26
<211> LENGTH: 9
<212> TYPE: PRT
<213> ORGANISM: Human

<400> SEQUENCE: 26

```
Thr Trp Asn Gln Met Asn Leu Gly Ala
1               5
```

<210> SEQ ID NO 27
<211> LENGTH: 9
<212> TYPE: PRT
<213> ORGANISM: Human

<400> SEQUENCE: 27

```
Met Asn Leu Gly Ala Thr Leu Lys Gly
1               5
```

<210> SEQ ID NO 28
<211> LENGTH: 9
<212> TYPE: PRT
<213> ORGANISM: Human

<400> SEQUENCE: 28

```
Met Thr Trp Asn Gln Met Asn Leu Gly
1               5
```

<210> SEQ ID NO 29
<211> LENGTH: 9
<212> TYPE: PRT
<213> ORGANISM: Human

<400> SEQUENCE: 29

```
Gly Ala Leu Arg Asn Pro Thr Ala Cys
1               5
```

<210> SEQ ID NO 30
<211> LENGTH: 9
<212> TYPE: PRT
<213> ORGANISM: Human

<400> SEQUENCE: 30

Gly Tyr Leu Arg Asn Pro Thr Ala Cys
1 5

<210> SEQ ID NO 31
<211> LENGTH: 9
<212> TYPE: PRT
<213> ORGANISM: Human

<400> SEQUENCE: 31

Gly Ala Leu Arg Asn Pro Thr Ala Leu
1 5

<210> SEQ ID NO 32
<211> LENGTH: 9
<212> TYPE: PRT
<213> ORGANISM: Human

<400> SEQUENCE: 32

Tyr Ala Leu Arg Asn Pro Thr Ala Cys
1 5

<210> SEQ ID NO 33
<211> LENGTH: 9
<212> TYPE: PRT
<213> ORGANISM: Human

<400> SEQUENCE: 33

Gly Leu Leu Arg Asn Pro Thr Ala Cys
1 5

<210> SEQ ID NO 34
<211> LENGTH: 9
<212> TYPE: PRT
<213> ORGANISM: Human

<400> SEQUENCE: 34

Arg Gln Arg Pro His Pro Gly Ala Leu
1 5

<210> SEQ ID NO 35
<211> LENGTH: 9
<212> TYPE: PRT
<213> ORGANISM: Human

<400> SEQUENCE: 35

Arg Tyr Arg Pro His Pro Gly Ala Leu
1 5

<210> SEQ ID NO 36
<211> LENGTH: 9
<212> TYPE: PRT
<213> ORGANISM: Human

<400> SEQUENCE: 36

Tyr Gln Arg Pro His Pro Gly Ala Leu
1 5

<210> SEQ ID NO 37
<211> LENGTH: 9
<212> TYPE: PRT
<213> ORGANISM: Human

<400> SEQUENCE: 37

Arg Leu Arg Pro His Pro Gly Ala Leu
1               5

<210> SEQ ID NO 38
<211> LENGTH: 9
<212> TYPE: PRT
<213> ORGANISM: Human

<400> SEQUENCE: 38

Arg Ile Arg Pro His Pro Gly Ala Leu
1               5

<210> SEQ ID NO 39
<211> LENGTH: 15
<212> TYPE: PRT
<213> ORGANISM: Human

<400> SEQUENCE: 39

Gln Phe Pro Asn His Ser Phe Lys His Glu Asp Pro Met Gly Gln
1               5                   10                  15

<210> SEQ ID NO 40
<211> LENGTH: 9
<212> TYPE: PRT
<213> ORGANISM: Human

<400> SEQUENCE: 40

His Ser Phe Lys His Glu Asp Pro Met
1               5

<210> SEQ ID NO 41
<211> LENGTH: 9
<212> TYPE: PRT
<213> ORGANISM: Human

<400> SEQUENCE: 41

His Ser Phe Lys His Glu Asp Pro Tyr
1               5

<210> SEQ ID NO 42
<211> LENGTH: 13
<212> TYPE: PRT
<213> ORGANISM: Human

<400> SEQUENCE: 42

Gln Phe Pro Asn His Ser Phe Lys His Glu Asp Pro Met
1               5                   10

<210> SEQ ID NO 43
<211> LENGTH: 13
<212> TYPE: PRT
<213> ORGANISM: Human

<400> SEQUENCE: 43

Gln Phe Pro Asn His Ser Phe Lys His Glu Asp Pro Tyr
1               5                   10

<210> SEQ ID NO 44
<211> LENGTH: 13

<212> TYPE: PRT
<213> ORGANISM: Human

<400> SEQUENCE: 44

Lys Arg Pro Phe Met Cys Ala Tyr Pro Gly Cys Asn Lys
1 5 10

<210> SEQ ID NO 45
<211> LENGTH: 9
<212> TYPE: PRT
<213> ORGANISM: Human

<400> SEQUENCE: 45

Phe Met Cys Ala Tyr Pro Gly Cys Asn
1 5

<210> SEQ ID NO 46
<211> LENGTH: 13
<212> TYPE: PRT
<213> ORGANISM: Human

<400> SEQUENCE: 46

Lys Arg Pro Phe Met Cys Ala Tyr Pro Gly Cys Tyr Lys
1 5 10

<210> SEQ ID NO 47
<211> LENGTH: 9
<212> TYPE: PRT
<213> ORGANISM: Human

<400> SEQUENCE: 47

Phe Met Cys Ala Tyr Pro Gly Cys Tyr
1 5

<210> SEQ ID NO 48
<211> LENGTH: 9
<212> TYPE: PRT
<213> ORGANISM: Human

<400> SEQUENCE: 48

Phe Met Cys Ala Tyr Pro Gly Cys Lys
1 5

<210> SEQ ID NO 49
<211> LENGTH: 15
<212> TYPE: PRT
<213> ORGANISM: Human

<400> SEQUENCE: 49

Lys Arg Pro Phe Met Cys Ala Tyr Pro Gly Cys Asn Lys Arg Tyr
1 5 10 15

<210> SEQ ID NO 50
<211> LENGTH: 15
<212> TYPE: PRT
<213> ORGANISM: Human

<400> SEQUENCE: 50

Ser Glu Lys Arg Pro Phe Met Cys Ala Tyr Pro Gly Cys Asn Lys
1 5 10 15

<210> SEQ ID NO 51
<211> LENGTH: 575
<212> TYPE: PRT
<213> ORGANISM: Human

<400> SEQUENCE: 51

```
Ser Arg Gln Arg Pro His Pro Gly Ala Leu Arg Asn Pro Thr Ala Cys
1               5                   10                  15

Pro Leu Pro His Phe Pro Pro Ser Leu Pro Pro Thr His Ser Pro Thr
            20                  25                  30

His Pro Pro Arg Ala Gly Thr Ala Ala Gln Ala Pro Gly Pro Arg Arg
        35                  40                  45

Leu Leu Ala Ala Ile Leu Asp Phe Leu Leu Leu Gln Asp Pro Ala Ser
    50                  55                  60

Thr Cys Val Pro Glu Pro Ala Ser Gln His Thr Leu Arg Ser Gly Pro
65                  70                  75                  80

Gly Cys Leu Gln Gln Pro Glu Gln Gln Gly Val Arg Asp Pro Gly Gly
                85                  90                  95

Ile Trp Ala Lys Leu Gly Ala Ala Glu Ala Ser Ala Glu Arg Leu Gln
            100                 105                 110

Gly Arg Arg Ser Arg Gly Ala Ser Gly Ser Glu Pro Gln Gln Met Gly
        115                 120                 125

Ser Asp Val Arg Asp Leu Asn Ala Leu Leu Pro Ala Val Pro Ser Leu
    130                 135                 140

Gly Gly Gly Gly Gly Cys Ala Leu Pro Val Ser Gly Ala Ala Gln Trp
145                 150                 155                 160

Ala Pro Val Leu Asp Phe Ala Pro Pro Gly Ala Ser Ala Tyr Gly Ser
                165                 170                 175

Leu Gly Gly Pro Ala Pro Pro Pro Ala Pro Pro Pro Pro Pro Pro Pro
            180                 185                 190

Pro Pro His Ser Phe Ile Lys Gln Glu Pro Ser Trp Gly Gly Ala Glu
        195                 200                 205

Pro His Glu Glu Gln Cys Leu Ser Ala Phe Thr Val His Phe Ser Gly
    210                 215                 220

Gln Phe Thr Gly Thr Ala Gly Ala Cys Arg Tyr Gly Pro Phe Gly Pro
225                 230                 235                 240

Pro Pro Pro Ser Gln Ala Ser Ser Gly Gln Ala Arg Met Phe Pro Asn
                245                 250                 255

Ala Pro Tyr Leu Pro Ser Cys Leu Glu Ser Gln Pro Ala Ile Arg Asn
            260                 265                 270

Gln Gly Tyr Ser Thr Val Thr Phe Asp Gly Thr Pro Ser Tyr Gly His
        275                 280                 285

Thr Pro Ser His His Ala Ala Gln Phe Pro Asn His Ser Phe Lys His
    290                 295                 300

Glu Asp Pro Met Gly Gln Gln Gly Ser Leu Gly Glu Gln Gln Tyr Ser
305                 310                 315                 320

Val Pro Pro Pro Val Tyr Gly Cys His Thr Pro Thr Asp Ser Cys Thr
                325                 330                 335

Gly Ser Gln Ala Leu Leu Leu Arg Thr Pro Tyr Ser Ser Asp Asn Leu
            340                 345                 350

Tyr Gln Met Thr Ser Gln Leu Glu Cys Met Thr Trp Asn Gln Met Asn
        355                 360                 365

Leu Gly Ala Thr Leu Lys Gly Val Ala Ala Gly Ser Ser Ser Ser Val
    370                 375                 380

Lys Trp Thr Glu Gly Gln Ser Asn His Ser Thr Gly Tyr Glu Ser Asp
385                 390                 395                 400

Asn His Thr Thr Pro Ile Leu Cys Gly Ala Gln Tyr Arg Ile His Thr
```

```
                405                 410                 415

His Gly Val Phe Arg Gly Ile Gln Asp Val Arg Arg Val Pro Gly Val
            420                 425                 430

Ala Pro Thr Leu Val Arg Ser Ala Ser Glu Thr Ser Glu Lys Arg Pro
        435                 440                 445

Phe Met Cys Ala Tyr Pro Gly Cys Asn Lys Arg Tyr Phe Lys Leu Ser
    450                 455                 460

His Leu Gln Met His Ser Arg Lys His Thr Gly Glu Lys Pro Tyr Gln
465                 470                 475                 480

Cys Asp Phe Lys Asp Cys Glu Arg Arg Phe Ser Arg Ser Asp Gln Leu
                485                 490                 495

Lys Arg His Gln Arg Arg His Thr Gly Val Lys Pro Phe Gln Cys Lys
            500                 505                 510

Thr Cys Gln Arg Lys Phe Ser Arg Ser Asp His Leu Lys Thr His Thr
        515                 520                 525

Arg Thr His Thr Gly Lys Thr Ser Glu Lys Pro Phe Ser Cys Arg Trp
    530                 535                 540

Pro Ser Cys Gln Lys Lys Phe Ala Arg Ser Asp Glu Leu Val Arg His
545                 550                 555                 560

His Asn Met His Gln Arg Asn Met Thr Lys Leu Gln Leu Ala Leu
                565                 570                 575


<210> SEQ ID NO 52
<211> LENGTH: 449
<212> TYPE: PRT
<213> ORGANISM: Human

<400> SEQUENCE: 52

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205
```

```
Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu


<210> SEQ ID NO 53
<211> LENGTH: 453
<212> TYPE: PRT
<213> ORGANISM: Human

<400> SEQUENCE: 53

Ala Ala Glu Ala Ser Ala Glu Arg Leu Gln Gly Arg Arg Ser Arg Gly
1               5                   10                  15

Ala Ser Gly Ser Glu Pro Gln Gln Met Gly Ser Asp Val Arg Asp Leu
            20                  25                  30

Asn Ala Leu Leu Pro Ala Val Pro Ser Leu Gly Gly Gly Gly Gly Cys
        35                  40                  45

Ala Leu Pro Val Ser Gly Ala Ala Gln Trp Ala Pro Val Leu Asp Phe
    50                  55                  60

Ala Pro Pro Gly Ala Ser Ala Tyr Gly Ser Leu Gly Gly Pro Ala Pro
65                  70                  75                  80

Pro Pro Ala Pro Pro Pro Pro Pro Pro Pro Pro Pro His Ser Phe Ile
                85                  90                  95

Lys Gln Glu Pro Ser Trp Gly Gly Ala Glu Pro His Glu Glu Gln Cys
            100                 105                 110

Leu Ser Ala Phe Thr Val His Phe Ser Gly Gln Phe Thr Gly Thr Ala
        115                 120                 125
```

```
Gly Ala Cys Arg Tyr Gly Pro Phe Gly Pro Pro Pro Pro Ser Gln Ala
    130                 135                 140

Ser Ser Gly Gln Ala Arg Met Phe Pro Asn Ala Pro Tyr Leu Pro Ser
145                 150                 155                 160

Cys Leu Glu Ser Gln Pro Ala Ile Arg Asn Gln Gly Tyr Ser Thr Val
                165                 170                 175

Thr Phe Asp Gly Thr Pro Ser Tyr Gly His Thr Pro Ser His His Ala
            180                 185                 190

Ala Gln Phe Pro Asn His Ser Phe Lys His Glu Asp Pro Met Gly Gln
        195                 200                 205

Gln Gly Ser Leu Gly Glu Gln Gln Tyr Ser Val Pro Pro Pro Val Tyr
    210                 215                 220

Gly Cys His Thr Pro Thr Asp Ser Cys Thr Gly Ser Gln Ala Leu Leu
225                 230                 235                 240

Leu Arg Thr Pro Tyr Ser Ser Asp Asn Leu Tyr Gln Met Thr Ser Gln
                245                 250                 255

Leu Glu Cys Met Thr Trp Asn Gln Met Asn Leu Gly Ala Thr Leu Lys
            260                 265                 270

Gly His Ser Thr Gly Tyr Glu Ser Asp Asn His Thr Thr Pro Ile Leu
        275                 280                 285

Cys Gly Ala Gln Tyr Arg Ile His Thr His Gly Val Phe Arg Gly Ile
    290                 295                 300

Gln Asp Val Arg Arg Val Pro Gly Val Ala Pro Thr Leu Val Arg Ser
305                 310                 315                 320

Ala Ser Glu Thr Ser Glu Lys Arg Pro Phe Met Cys Ala Tyr Pro Gly
                325                 330                 335

Cys Asn Lys Arg Tyr Phe Lys Leu Ser His Leu Gln Met His Ser Arg
            340                 345                 350

Lys His Thr Gly Glu Lys Pro Tyr Gln Cys Asp Phe Lys Asp Cys Glu
        355                 360                 365

Arg Arg Phe Ser Arg Ser Asp Gln Leu Lys Arg His Gln Arg Arg His
    370                 375                 380

Thr Gly Val Lys Pro Phe Gln Cys Lys Thr Cys Gln Arg Lys Phe Ser
385                 390                 395                 400

Arg Ser Asp His Leu Lys Thr His Thr Arg Thr His Thr Gly Glu Lys
                405                 410                 415

Pro Phe Ser Cys Arg Trp Pro Ser Cys Gln Lys Lys Phe Ala Arg Ser
            420                 425                 430

Asp Glu Leu Val Arg His His Asn Met His Gln Arg Asn Met Thr Lys
        435                 440                 445

Leu Gln Leu Ala Leu
    450
```

<210> SEQ ID NO 54
<211> LENGTH: 514
<212> TYPE: PRT
<213> ORGANISM: Human

<400> SEQUENCE: 54

```
Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45
```

-continued

```
Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Pro Ala Pro
        115                 120                 125

Pro Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly Val Ala Ala
305                 310                 315                 320

Gly Ser Ser Ser Ser Val Lys Trp Thr Glu Gly Gln Ser Asn His Ser
                325                 330                 335

Thr Gly Tyr Glu Ser Asp Asn His Thr Thr Pro Ile Leu Cys Gly Ala
            340                 345                 350

Gln Tyr Arg Ile His Thr His Gly Val Phe Arg Gly Ile Gln Asp Val
        355                 360                 365

Arg Arg Val Pro Gly Val Ala Pro Thr Leu Val Arg Ser Ala Ser Glu
    370                 375                 380

Thr Ser Glu Lys Arg Pro Phe Met Cys Ala Tyr Pro Gly Cys Asn Lys
385                 390                 395                 400

Arg Tyr Phe Lys Leu Ser His Leu Gln Met His Ser Arg Lys His Thr
                405                 410                 415

Gly Glu Lys Pro Tyr Gln Cys Asp Phe Lys Asp Cys Glu Arg Arg Phe
            420                 425                 430

Ser Arg Ser Asp Gln Leu Lys Arg His Gln Arg Arg His Thr Gly Val
        435                 440                 445

Lys Pro Phe Gln Cys Lys Thr Cys Gln Arg Lys Phe Ser Arg Ser Asp
    450                 455                 460
```

```
His Leu Lys Thr His Thr Arg Thr His Thr Gly Glu Lys Pro Phe Ser
465                 470                 475                 480

Cys Arg Trp Pro Ser Cys Gln Lys Lys Phe Ala Arg Ser Asp Glu Leu
                485                 490                 495

Val Arg His His Asn Met His Gln Arg Asn Met Thr Lys Leu Gln Leu
            500                 505                 510

Ala Leu


<210> SEQ ID NO 55
<211> LENGTH: 15
<212> TYPE: PRT
<213> ORGANISM: Human

<400> SEQUENCE: 55

Lys Arg Pro Phe Met Cys Ala Tyr Pro Gly Cys Tyr Lys Arg Tyr
1               5                   10                  15


<210> SEQ ID NO 56
<211> LENGTH: 9
<212> TYPE: PRT
<213> ORGANISM: Human

<400> SEQUENCE: 56

Arg Met Phe Pro Asn Ala Pro Tyr Leu
1               5


<210> SEQ ID NO 57
<211> LENGTH: 9
<212> TYPE: PRT
<213> ORGANISM: Human

<400> SEQUENCE: 57

Cys Met Thr Trp Asn Gln Met Asn Leu
1               5


<210> SEQ ID NO 58
<211> LENGTH: 9
<212> TYPE: PRT
<213> ORGANISM: Human

<400> SEQUENCE: 58

Tyr Met Phe Pro Asn Ala Pro Tyr Leu
1               5


<210> SEQ ID NO 59
<211> LENGTH: 15
<212> TYPE: PRT
<213> ORGANISM: Human

<400> SEQUENCE: 59

Gly Val Cys Val Cys Gly Asp Glu Asn Ile Leu Val Gln Glu Phe
1               5                   10                  15


<210> SEQ ID NO 60
<211> LENGTH: 25
<212> TYPE: PRT
<213> ORGANISM: Human

<400> SEQUENCE: 60

Ile Val His Ser Ala Thr Gly Phe Lys Gln Ser Ser Lys Ala Leu Gln
1               5                   10                  15

Arg Pro Val Ala Ser Asp Phe Glu Pro
            20                  25
```

```
<210> SEQ ID NO 61
<211> LENGTH: 9
<212> TYPE: PRT
<213> ORGANISM: Human

<400> SEQUENCE: 61

Gln Leu Gln Asn Pro Ser Tyr Asp Lys
1               5


<210> SEQ ID NO 62
<211> LENGTH: 9
<212> TYPE: PRT
<213> ORGANISM: Human

<400> SEQUENCE: 62

Thr Tyr Ser Val Ser Phe Asp Ser Leu
1               5
```

IMMUNOGENIC WT-1 PEPTIDES AND METHODS OF USE THEREOF

CROSS-REFERENCE TO RELATED APPLICATIONS

This application is a divisional of U.S. patent application Ser. No. 15/920,335, filed Mar. 13, 2018, claiming priority of U.S. patent application Ser. No. 14/760,997, filed Jul. 14, 2015, claiming priority of International Application No. PCT/US14/11711, international filing date Jan. 15, 2014, claiming priority of Provisional Patent Application, 61/752,799, filed Jan. 15, 2013, which is hereby incorporated by reference.

GOVERNMENT INTEREST STATEMENT

This invention was made with government support under CA023766 awarded by the National Institutes of Health. The government has certain rights in the invention.

FIELD OF INVENTION

This invention provides peptides, compositions and vaccines comprising same, and methods of treating, reducing the incidence of, and inducing immune responses to a WT1-expressing cancer, comprising administering same.

BACKGROUND OF THE INVENTION

Wilms tumor (WT), a pediatric nephroblastoma that occurs with a frequency of 1 in 10,000 births, has been the subject of intense clinical and basic research for several years. The tumor is embryonic in origin, it is detected in children usually during the first 5 years of life and can occur unilaterally or bilaterally. A WT arises when condensed metanephric mesenchymal cells of the developing kidney fail to properly differentiate. The implication of the Wilms tumor 1 (WT1) tumor suppressor gene in the etiology of WT illustrated the impact that genetic alterations can have on both development and tumorigenesis.

Wilms tumor protein I (WT1) is a zinc finger transcription factor expressed during normal ontogenesis such as in fetal kidney, testis and ovary. In adults, WTI expression is limited to low levels on hematopoietic stem cells, myoepithelial progenitor cells, renal podocytes and some cells in testis and ovary. Recent demonstration that WTI is over expressed in several types of leukemia suggested that WTI would be an attractive target for immunotherapy for various cancers.

The Wilms' tumor oncogene protein (WT1) is an attractive target for immunotherapy for leukemias and a wide range of cancers. Peptides derived from the WT1 protein have been identified that induce HLA-A0201-restricted cytotoxic CD8 T cells, capable of killing tumor cells. Two peptides that bind to HLA-A0201 (RMFPNAPYL; SEQ ID NO:56) or HLA-A2402 (CMTWNQMNL; SEQ ID NO:57) have been extensively studied worldwide and have been in clinical trials in patients with leukemia and other solid tumors (Oka et al., Scientific World Journal 2007; 7: 649-665; Mundlos et al. Development 1993; 119:1329-41; Keilholz et al. Leukemia 2005; 19: 1318-1323). These results are encouraging and have provided strong evidence and a rational for therapeutic targeting of the WT1-derived T cell epitopes for leukemias and a wide range of human cancers.

The therapeutic application of the above two WT1-derived peptides is limited to the people who are HLA-A0201, an HLA haplotype found in about 40% of Caucasians and HLA-A2402, a found haplotype in about 40% of Japanese and other Asian populations. Therefore, there is an unmet need for WT1-derived peptides that might be used for most of the world's populations. To extend the therapeutic application in a broader range of population, novel peptides derived from WT1 protein that bind to multiple HLA haplotypes are desired. Such peptides would therefore be capable of stimulating T cells from a larger percentage of the target population, allowing a vaccine strategy that would address a large segment of the population, with durable cytotoxic memory cells.

SUMMARY OF THE INVENTION

This invention provides peptides, compositions, and immunogenic compositions such as vaccines comprising immunogenic peptides, and methods of treating, reducing the incidence of, and inducing immune responses to a WT1-expressing cancer, comprising administering immunogenic peptides, or stimulating T cells outside of a human patient that can then be infused into the patient for treatment.

In one embodiment, the present invention provides an isolated peptide having an amino acid (AA) sequence consisting of any one of the sequences SEQ ID NO:6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55. In one embodiment, the present invention provides an isolated HLA class I binding peptide having an amino acid (AA) sequence consisting of any one of the sequences SEQ ID NO:6, 7, 30, 31, 32, 33, 34, 35, 36, 37, 38, 41, 42, 47 and 48. In one embodiment, the present invention provides an isolated HLA class II binding WT1 peptide having an amino acid (AA) sequence consisting of any one of the sequences SEQ ID NO: 8, 9, 10, 11, 12, 13, 14, 15, 16, 17, 18, 19, 20, 21, 22, 23, 39, 43, 44, 46, 49, 50 and 55.

In one embodiment, the present invention provides an isolated peptide having an amino acid (AA) sequence consisting of any one of the sequences SEQ ID NO:6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55, or a fragment of any one of the foregoing. In one embodiment, the present invention provides an isolated HLA class I binding peptide having an amino acid (AA) sequence consisting of any one of the sequences SEQ ID NO:6, 7, 30, 31, 32, 33, 34, 35, 36, 37, 38, 41, 42, 47 and 48 or a fragment of any one of the foregoing. In one embodiment, the present invention provides an isolated HLA class II binding WT1 peptide having an amino acid (AA) sequence consisting of any one of the sequences SEQ ID NO: 8, 9, 10, 11, 12, 13, 14, 15, 16, 17, 18, 19, 20, 21, 22, 23, 39, 43, 44, 46, 49, 50 and 55 or a fragment of any one of the foregoing.

In another embodiment, the present invention provides a composition comprising (a) an antigen-presenting cell and (b) a peptide selected from SEQ ID NO:6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55. In another embodiment, the present invention provides a composition comprising (a) an antigen-presenting cell and (b) an HLA class I binding peptide selected from SEQ ID NO: 6, 7, 30, 31, 32, 33, 34, 35, 36, 37, 38, 41, 42, 47 and 48. In another embodiment, the present invention provides a composition comprising (a) an antigen-presenting cell and (b) an HLA class II binding peptide selected from SEQ ID NO: 8, 9, 10, 11, 12, 13, 14, 15, 16, 17, 18, 19, 20, 21, 22, 23, 39, 43, 44, 46, 49, 50 and 55.

In another embodiment, the present invention provides a vaccine comprising one or more peptides of SEQ ID NO: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55. In another embodiment, the present invention provides a vaccine comprising one or more HLA class I binding peptides selected from SEQ ID NO: 6, 7, 30, 31, 32, 33, 34, 35, 36, 37, 38, 41, 42, 47 and 48. In another embodiment, the present invention provides a vaccine comprising one or more HLA class II binding peptides selected from SEQ ID NO 8, 9, 10, 11, 12, 13, 14, 15, 16, 17, 18, 19, 20, 21, 22, 23, 39, 43, 44, 46, 49, 50 and 55. In another embodiment, the present invention provides a vaccine comprising one or more HLA class I binding peptides selected from SEQ ID NO: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55, and one or more HLA class II binding peptides selected from SEQ ID NO: 8, 9, 10, 11, 12, 13, 14, 15, 16, 17, 18, 19, 20, 21, 22, 23, 39, 43, 44, 46, 49, 50 and 55.

In another embodiment, the present invention provides a method of treating a subject with a WT1-expressing cancer, the method comprising administering to the subject a peptide or vaccine of the present invention, thereby treating a subject with a WT1-expressing cancer.

In another embodiment, the present invention provides a method of reducing the incidence of a WT1-expressing cancer, or its relapse, in a subject, the method comprising administering to the subject a peptide or vaccine of the present invention, thereby reducing the incidence of a WT1-expressing cancer, or its relapse, in a subject.

In another embodiment, the present invention provides a method of inducing an anticancer immune response in a subject, the method comprising the step of contacting the subject with an immunogenic composition comprising (a) a WT1 protein; (b) a modified fragment of a WT protein; (c) a nucleotide molecule encoding a WT1 protein; or (d) a nucleotide molecule encoding a modified fragment of a WT1 protein, thereby inducing an anti-mesothelioma immune response in a subject. In one embodiment, the modified fragment of a WT1 protein consists of a peptide or comprises a peptide from among SEQ ID NO: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55.

In another embodiment, the present invention provides a method of treating a subject with a cancer, the method comprising the step of administering to the subject an immunogenic composition comprising (a) a WT1 protein; (b) a modified fragment of a WT protein; (c) a nucleotide molecule encoding a WT1 protein; or (d) a nucleotide molecule encoding a modified fragment of a WT1 protein, thereby treating a subject with a mesothelioma. In one embodiment, the modified fragment of a WT1 protein is a peptide from among SEQ ID NO: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55.

In another embodiment, the present invention provides a method of reducing an incidence of a cancer, or its relapse, in a subject, the method comprising the step of administering to the subject an immunogenic composition comprising (a) a WT1 protein; (b) a modified fragment of a WT protein; (c) a nucleotide molecule encoding a WT1 protein; or (d) a nucleotide molecule encoding a modified fragment of a WT1 protein, thereby reducing an incidence of a mesothelioma, or its relapse, in a subject. In one embodiment, the fragment of a WT1 protein is a peptide from among SEQ ID NO: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55.

In another embodiment, the cancer is a WT1-expressing cancer. In one embodiment, the WT1-expressing cancer is an acute myelogenous leukemia (AML). In another embodiment, the WT1-expressing cancer is associated with a myelodysplastic syndrome (MDS). In another embodiment, the WT1-expressing cancer is an MDS. In another embodiment, the WT1-expressing cancer is a non-small cell lung cancer (NSCLC). In another embodiment, the WT1-expressing cancer is a Wilms' tumor. In another embodiment, the WT1-expressing cancer is a leukemia. In another embodiment, the WT1-expressing cancer is a hematological cancer. In another embodiment, the WT1-expressing cancer is a lymphoma. In another embodiment, the WT1-expressing cancer is a desmoplastic small round cell tumor. In another embodiment, the WT1-expressing cancer is a mesothelioma. In another embodiment, the WT1-expressing cancer is a malignant mesothelioma. In another embodiment, the WT1-expressing cancer is a gastric cancer. In another embodiment, the WT1-expressing cancer is a colon cancer. In another embodiment, the WT1-expressing cancer is a lung cancer. In another embodiment, the WT1-expressing cancer is a breast cancer. In another embodiment, the WT1-expressing cancer is a germ cell tumor. In another embodiment, the WT1-expressing cancer is an ovarian cancer. In another embodiment, the WT1-expressing cancer is a uterine cancer. In another embodiment, the WT1-expressing cancer is a thyroid cancer. In another embodiment, the WT1-expressing cancer is a hepatocellular carcinoma. In another embodiment, the WT1-expressing cancer is a thyroid cancer. In another embodiment, the WT1-expressing cancer is a liver cancer. In another embodiment, the WT1-expressing cancer is a renal cancer. In another embodiment, the WT1-expressing cancer is a Kaposi's sarcoma. In another embodiment, the WT1-expressing cancer is a sarcoma. In another embodiment, the WT1-expressing cancer is any other carcinoma or sarcoma.

In another embodiment, the WT1-expressing cancer is a solid tumor. In another embodiment, the solid tumor is associated with a WT1-expressing cancer. In another embodiment, the solid tumor is associated with a myelodysplastic syndrome (MDS). In another embodiment, the solid tumor is associated with a non-small cell lung cancer (NSCLC). In another embodiment, the solid tumor is associated with a lung cancer. In another embodiment, the solid tumor is associated with a breast cancer. In another embodiment, the solid tumor is associated with a colorectal cancer. In another embodiment, the solid tumor is associated with a prostate cancer. In another embodiment, the solid tumor is associated with an ovarian cancer. In another embodiment, the solid tumor is associated with a renal cancer. In another embodiment, the solid tumor is associated with a pancreatic cancer. In another embodiment, the solid tumor is associated with a brain cancer. In another embodiment, the solid tumor is associated with a gastrointestinal cancer. In another embodiment, the solid tumor is associated with a skin cancer. In another embodiment, the solid tumor is associated with a melanoma.

In another embodiment, the present invention provides a composition comprising an isolated peptide of the invention in combination with at least 1 additional peptide. In certain embodiments, a composition comprising at least 2 different isolated peptides of the present invention is provided. In certain embodiments, a composition comprising at least 3 or at least 4 different isolated peptides of the present invention is provided. Each possibility represents a separate embodiment of the present invention. In certain embodiments, the composition of the present invention is a vaccine.

In another embodiment, the present invention provides a method of treating a subject with a WT1-expressing cancer, the method comprising administering to the subject a peptide or composition of the present invention, thereby treating a subject with a WT1-expressing cancer.

In another embodiment, the present invention provides a method of reducing the incidence of a WT1-expressing cancer, or its relapse, in a subject, the method comprising administering to the subject a peptide or composition of the present invention, thereby reducing the incidence of a WT1-expressing cancer, or its relapse, in a subject.

In another embodiment, the present invention provides a method of inducing formation and proliferation of a WT1 protein-specific CTL, the method comprising contacting a lymphocyte population with a peptide or composition of the present invention, thereby inducing formation and proliferation of a WT1 protein-specific CTL. This method can be conducted in vitro, ex vivo or in vivo. When conducted in vitro or ex vivo, these CTL can then be infused into a patient for therapeutic effect.

In another embodiment, the present invention provides a method of inducing formation and proliferation of (a) a WT1 protein-specific $CD8^+$ lymphocyte; or (b) a $CD4^+$ lymphocyte specific for the WT1 protein, or the combination thereof, the method f contacting a lymphocyte population with a peptide or composition of the present invention, thereby inducing formation and proliferation of (a) a WT1 protein-specific $CD8^+$ lymphocyte; or (b) a $CD4^+$ lymphocyte specific for the WT1 protein; or a combination thereof. This method can be conducted in vitro, ex vivo or in vivo. When conducted in vitro or ex vivo, these CTL can then be infused into a patient for therapeutic effect.

BRIEF DESCRIPTION OF THE FIGURES

So that the matter in which the above-recited features, advantages and objects of the invention, as well as others which will become clear, are attained and can be understood in detail, more particular descriptions of the invention are briefly summarized. Details of the above may be had by reference to certain embodiments thereof, which are illustrated in the appended drawings. These drawings form a part of the specification. It is to be noted; however, that the appended drawings illustrate preferred embodiments of the invention and therefore are not to be considered limiting in their scope. In the figures herein, the set of clustered data bars in the graphs for each peptide are presented in the same order from left to right as in shown the figure legend from top to bottom.

DETAILED DESCRIPTION OF THE INVENTION

Figure 1:
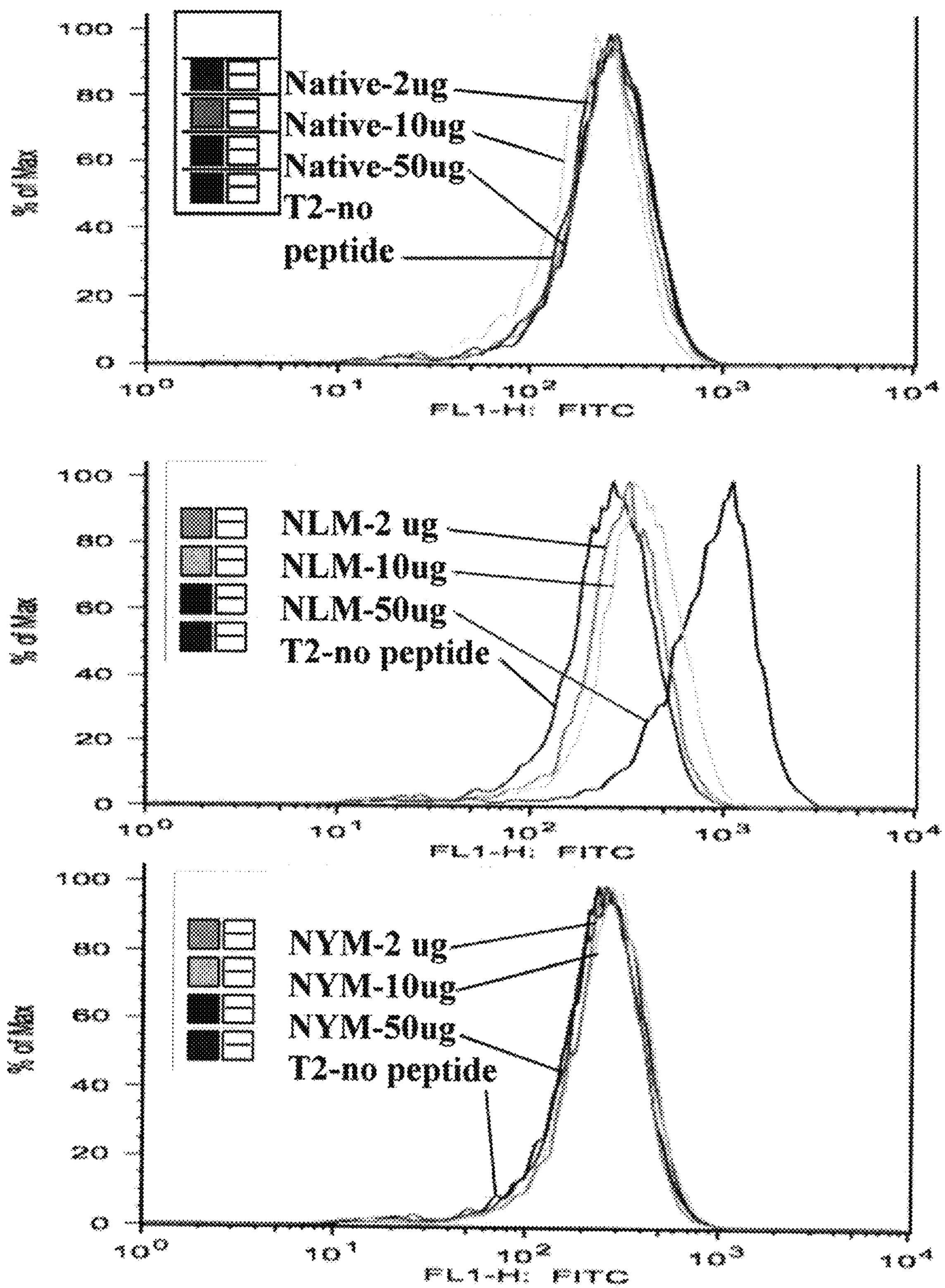
FIG. 1 shows the results of a T2 stabilization assay showing that binding of NLMNLGATL peptide to HLA-A2 molecule is stronger than NQMNLGATL and NYMNLGATL peptides. Native NQMNLGATL, heteroclitic NLMNLGATL or NYMNLGATL was pulsed onto T2 cells at the indicated concentrations as described in the Materials and methods. The stabilization of the HLA-A2 molecule by the peptides was measured by the expression of HLA-A2 molecule.

This invention provides immunogenic peptides, and compositions and vaccines comprising immunogenic peptides, and methods of treating, reducing the incidence of, and inducing immune responses to a WT1-expressing cancer, comprising administering one or more immunogenic peptides.

This invention provides synthetic peptides and methods of treating, reducing the incidence of, and inducing immune responses against a WT1-expressing cancer, comprising immunogenic peptides.

The WT1 molecule from which the peptides of the present invention are derived has, in another embodiment, the sequence:

```
                                          (SEQ ID NO: 51)
  1 SRQRPHPGAL RNPTACPLPH FPPSLPPTHS PTHPPRAGTA AQAPGPRRLL

 51 AAILDFLLLQ DPASTCVPEP ASQHTLRSGP GCLQQPEQQG VRDPGGIWAK

101 LGAAEASAER LQGRRSRGAS GSEPQQMGSD VRDLNALLPA VPSLGGGGGC

151 ALPVSGAAQW APVLDFAPPG ASAYGSLGGP APPPAPPPPP PPPPHSFIKQ

201 EPSWGGAEPH EEQCLSAFTV HFSGQFTGTA GACRYGPFGP PPPSQASSGQ

251 ARMFPNAPYL PSCLESQPAI RNQGYSTVTF DGTPSYGHTP SHHAAQFPNH

301 SFKHEDPMGQ QGSLGEQQYS VPPPVYGCHT PTDSCTGSQA LLLRTPYSSD

351 NLYQMTSQLE CMTWNQMNLG ATLKGVAAGS SSSVKWTEGQ SNHSTGYESD

401 NHTTPILCGA QYRIHTHGVF RGIQDVRRVP GVAPTLVRSA SETSEKRPFM

451 CAYPGCNKRY FKLSHLQMHS RKHTGEKPYQ CDFKDCERRF SRSDQLKRHQ

501 RRHTGVKPFQ CKTCQRKFSR SDHLKTHTRT HTGKTSEKPF SCRWPSCQKK

551 FARSDELVRH HNMHQRNMTK LQLAL.
```

The foregoing sequence of the WT-1 protein is that published by Gessler et al. (Gessler M, Poustka A, Cavenee W, Neve R L, Orkin S H, Bruns G A. Homozygous deletion in Wilms tumours of a zinc-finger gene identified by chromosome jumping. *Nature*. 1990; 343(6260):774-778. Prepublished on 1990 Feb. 22 as DOI 10.1038/343774a0.) which comprises 575 amino acids and includes the first 126 amino acids in the N-terminus missing in the (Exon 5+, KTS+) isoform of WT-116.

In another embodiment, the WT1 sequence is

```
   (GenBank Accession number AY245105; SEQ ID NO: 52)
MGSDVRDLNALLPAVPSLGGGGGCALPVSGAAQWAPVLDFAPPGASAYGS

LGGPAPPPAPPPPPPPPPHSFIKQEPSWGGAEPHEEQCLSAFTVHFSGQF

TGTAGACRYGPFGPPPPSQASSGQARMFPNAPYLPSCLESQPAIRNGYST

VTFDGTPSYGHTPSHHAAQFPNHSFKHEDPMQGQQGSLGEQQYSVPPPVY

GCHTPTDSCTGSQALLLRTPYSSDNLYQMTSQLECMTWNQMNLGATLKGV

AAGSSSSVKWTEGQSNHSTGYESDNHTTPILCGAQYRIHTHGVFRGIQDV

RRVPGVAPTLVRSASETSEKRPFMCAYPGCNKRYFKLSHLQMHSRKHTGE

KPYQCDFKDCERRFSRSDQLKRHQRRHTGVKPFQCKTCQRKFSRSDHLKT

HTRTHTGKTSEKPFSCRWPSCQKKFARSDELVRHHNMHQRNMTKLQLAL.
```

In another embodiment, the WT1 molecule has the sequence:

```
                        (GenBank Accession number NM_000378;
                                              SEQ ID NO: 53)
AAEASAERLQGRRSRGASGSEPQQMGSDVRDLNALLPAVPSLGGGGGCA

LPVSGAAQWAPVLDFAPPGASAYGSLGGPAPPPAPPPPPPPPPHSFIKQ

EPSWGGAEPHEEQCLSAFTVHFSGQFTGTAGACRYGPFGPPPPSQASSG
```

-continued

```
QARMFPNAPYLPSCLESQPAIRNQGYSTVTFDGTPSYGHTPSHHAAQFP

NHSFKHEDPMGQQGSLGEQQYSVPPPVYGCHTPTDSCTGSQALLLRTPY

SSDNLYQMTSQLECMTWNQMNLGATLKGHSTGYESDNHTTPILCGAQYR
```

-continued

```
IHTHGVFRGIQDVRRVPGVAPTLVRSASETSEKRPFMCAYPGCNKRYFK

LSHLQMHSRKHTGEKPYQCDFKDCERRFSRSDQLKRHQRRHTGVKPFQC

KTCQRKFSRSDHLKTHTRTHTGEKPFSCRWPSCQKKFARSDELVRHHNM

HQRNMTKLQLAL.
```

In another embodiment, the WT1 molecule has the sequence:

```
                        (GenBank Accession number NP_077742;
                                              SEQ ID No: 54)
MQDPASTCVPEPASQHTLRSGPGCLQQPEQQGVRDPGGIWAKLGAAEA

SAERLQGRRSRGASGSEPQQMGSDVRDLNALLPAVPSLGGGGGCALPV

SGAAQWAPVLDFAPPGASAYGSLGGPAPPPAPPPPPPPPPHSFIKQEP

SWGGAEPHEEQCLSAFTVHFSGQFTGTAGACRYGPFGPPPPSQASSGQ

ARMFPNAPYLPSCLESQPAIRNQGYSTVTFDGTPSYGHTPSHHAAQFP

NHSFKHEDPMGQQGSLGEQQYSVPPPVYGCHTPTDSCTGSQALLLRTP

YSSDNLYQMTSQLECMTWNQMNLGATLKGVAAGSSSSVKWTEGQSNHS

TGYESDNHTTPILCGAQYRIHTHGVFRGIQDVRRVPGVAPTLVRSASE

TSEKRPFMCAYPGCNKRYFKLSHLQMHSRKHTGEKPYQCDFKDCERRF

SRSDQLKRHQRRHTGVKPFQCKTCQRKFSRSDHLKTHTRTHTGEKPFS

CRWPSCQKKFARSDELVRHHNMHQRNMTKLQLAL.
```

In another embodiment, the WT1 protein has the sequence set forth in GenBank Accession #NM_024426. In other embodiments, the WT1 protein has or comprises one of the sequences set forth in one of the following sequence entries: NM_024425, NM_024424, NM_000378, 595530, D13624, D12496, D 12497, or X77549. In another embodiment, the WT1 protein has any other WT1 sequence known in the art.

This invention provides peptides, compositions, and immunogenic compositions such as vaccines comprising immunogenic peptides, and methods of treating, reducing the incidence of, and inducing immune responses to a WT1-expressing cancer, comprising administering immunogenic peptides. In some cases, the peptides described herein are derived from peptides that are native sequences of WT1, and may be referred to herein as WT1-derived peptides or as a WT1 peptide.

In one embodiment, the present invention provides an isolated WT1 peptide having an amino acid (AA) sequence consisting of any one of the sequences SEQ ID NO:6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55. In one embodiment, the present invention provides an isolated HLA class I binding WT1 peptide having an amino acid (AA) sequence consisting of any one of the sequences SEQ ID NO:6, 7, 30, 31, 32, 33, 34, 35, 36, 37, 38, 41, 42, 47 and 48. In one embodiment, the present invention provides an isolated HLA class II binding WT1 peptide having an amino acid (AA) sequence consisting of any one of the sequences SEQ ID NO:8, 9, 10, 11, 12, 13, 14, 15, 16, 17, 18, 19, 20, 21, 22, 23, 39, 43, 44, 46, 49, 50 and 55. In another embodiment the HLA class I peptides consist of or comprise SEQ ID NO:6, 7, 30, 31, 32, 33, 34, 35, 36, 37, 38, 41, 42, 47 and 48, and the HLA class II peptide consists of or comprises SEQ ID NO:8, 9, 10, 11, 12, 13, 14, 15, 16, 17, 18, 19, 20, 21, 22, 23, 39, 43, 44, 46, 49, 50 and 55.

In one embodiment, the present invention provides an isolated WT1 peptide having an amino acid (AA) sequence comprising any one of the sequences SEQ ID NO:6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55, or a fragment thereof. In one embodiment, the present invention provides an isolated HLA class I binding WT1-derived peptide having an amino acid (AA) sequence comprising of any one of the sequences SEQ ID NO:6, 7, 30, 31, 32, 33, 34, 35, 36, 37, 38, 41, 42, 47 and 48. In one embodiment, the present invention provides an isolated HLA class II binding WT1 peptide having an amino acid (AA) sequence comprising of any one of the sequences SEQ ID NO:8, 9, 10, 11, 12, 13, 14, 15, 16, 17, 18, 19, 20, 21, 22, 23, 39, 43, 44, 46, 49, 50 and 55. In another embodiment the HLA class I peptides consist of or comprise SEQ ID NO:6, 7, 30, 31, 32, 33, 34, 35, 36, 37, 38, 41, 42, 47 and 48, and the HLA class II peptide consists of or comprises SEQ ID NO:8, 9, 10, 11, 12, 13, 14, 15, 16, 17, 18, 19, 20, 21, 22, 23, 39, 43, 44, 46, 49, 50 and 55.

In another embodiment, the present invention provides a composition comprising (a) an antigen-presenting cell and (b) a peptide selected from SEQ ID NO: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55. In another embodiment, the present invention provides a composition comprising (a) an antigen-presenting cell and (b) an HLA class I binding peptide selected from SEQ ID NO:6, 7, 30, 31, 32, 33, 34, 35, 36, 37, 38, 41, 42, 47 and 48. In another embodiment, the present invention provides a composition comprising (a) an antigen-presenting cell and (b) an HLA class II binding peptide selected from SEQ ID NO: 8, 9, 10, 11, 12, 13, 14, 15, 16, 17, 18, 19, 20, 21, 22, 23, 39, 43, 44, 46, 49, 50 and 55. In another embodiment the HLA class I peptides consist of or comprise SEQ ID NO:6, 7, 30, 31, 32, 33, 34, 35, 36, 37, 38, 41, 42, 47 and 48, and the HLA class II peptide consists of or comprises SEQ ID NO:8, 9, 10, 11, 12, 13, 14, 15, 16, 17, 18, 19, 20, 21, 22, 23, 39, 43, 44, 46, 49, 50 and 55.

In another embodiment, the present invention provides a vaccine comprising one or more peptides of SEQ ID NO:6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55. In another embodiment, the present invention provides a vaccine comprising one or more HLA class I binding peptides selected from SEQ ID NO:6, 7, 30, 31, 32, 33, 34, 35, 36, 37, 38, 41, 42, 47 and 48. In another embodiment, the present invention provides a vaccine comprising one or more HLA class II binding peptides selected from SEQ ID NO: 8, 9, 10, 11, 12, 13, 14, 15, 16, 17, 18, 19, 20, 21, 22, 23, 39, 43, 44, 46, 49, 50 and 55. In another embodiment, the present invention provides a vaccine comprising one or more HLA class I binding peptides selected from SEQ ID NO:6, 7, 30, 31, 32, 33, 34, 35, 36, 37, 38, 41, 42, 47 and 48, and one or more HLA class II binding peptides selected from SEQ ID NO: 8, 9, 10, 11, 12, 13, 14, 15, 16, 17, 18, 19, 20, 21, 22, 23, 39, 43, 44, 46, 49, 50 and 55. In another embodiment the HLA class I peptides consist of or comprise SEQ ID NO:6, 7, 30, 31, 32, 33, 34, 35, 36, 37, 38, 41, 42, 47 and 48, and the HLA class II peptide consists of or comprises SEQ ID NO:8, 9, 10, 11, 12, 13, 14, 15, 16, 17, 18, 19, 20, 21, 22, 23, 39, 43, 44, 46, 49, 50 and 55.

In another embodiment, the present invention provides a method of treating a subject with a WT1-expressing cancer, the method comprising administering to the subject a WT1 peptide or vaccine of the present invention, thereby treating a subject with a WT1-expressing cancer.

In another embodiment, the present invention provides a method of reducing the incidence of a WT1-expressing cancer, or its relapse, in a subject, the method comprising administering to the subject a WT1 peptide or vaccine of the present invention, thereby reducing the incidence of a WT1-expressing cancer, or its relapse, in a subject.

In another embodiment, the present invention provides a method of inducing an anticancer immune response in a subject, the method comprising the step of contacting the subject with an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby inducing an anti-mesothelioma immune response in a subject. In one embodiment, the fragment of a WT1 protein consists of a peptide or comprises a peptide from among SEQ ID NO:6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55. In another embodiment the fragment consists of a peptide or comprises a peptide from among SEQ ID NO:6, 7, 30, 31, 32, 33, 34, 35, 36, 37, 38, 41, 42, 47 and 48, or SEQ ID NO: 8, 9, 10, 11, 12, 13, 14, 15, 16, 17, 18, 19, 20, 21, 22, 23, 39, 43, 44, 46, 49, 50 and 55.

In another embodiment, the present invention provides a method of treating a subject with a cancer, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby treating a subject with a mesothelioma. In one embodiment, the fragment of a WT1 protein is a peptide from among SEQ ID NO:6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55. In another embodiment the fragment consists of a peptide or comprises a peptide from among SEQ ID NO:6, 7, 30, 31, 32, 33, 34, 35, 36, 37, 38, 41, 42, 47 and 48, or SEQ ID NO: 8, 9, 10, 11, 12, 13, 14, 15, 16, 17, 18, 19, 20, 21, 22, 23, 39, 43, 44, 46, 49, 50 and 55. In another embodiment the HLA class I peptides consist of or comprise SEQ ID NO:6, 7, 30, 31, 32, 33, 34, 35, 36, 37, 38, 41, 42, 47 and 48, and the HLA class II peptide consists of or comprises SEQ ID NO:8, 9, 10, 11, 12, 13, 14, 15, 16, 17, 18, 19, 20, 21, 22, 23, 39, 43, 44, 46, 49, 50 and 55.

In another embodiment, the present invention provides a method of reducing an incidence of a cancer, or its relapse, in a subject, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby reducing an incidence of a mesothelioma, or its relapse, in a subject. In one embodiment, the fragment of a WT1 protein is a peptide from among SEQ ID NO:6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55. In another embodiment the fragment consists of a peptide or comprises a peptide from among SEQ ID NO:6, 7, 30, 31, 32, 33, 34, 35, 36, 37, 38, 41, 42, 47 and 48, or SEQ ID NO: 8, 9, 10, 11, 12, 13, 14, 15, 16, 17, 18, 19, 20, 21, 22, 23, 39, 43, 44, 46, 49, 50 and 55. In another embodiment the HLA class I peptides consist of or comprise SEQ ID NO:6, 7, 30, 31, 32, 33, 34, 35, 36, 37, 38, 41, 42, 47 and 48, and the HLA class II peptide consists of or comprises SEQ ID NO:8, 9, 10, 11, 12, 13, 14, 15, 16, 17, 18, 19, 20, 21, 22, 23, 39, 43, 44, 46, 49, 50 and 55.

In another embodiment, the present invention provides a method of treating a subject with a WT1-expressing cancer, the method comprising administering to the subject a WT1 peptide or vaccine of the present invention, thereby treating a subject with a WT1-expressing cancer.

In another embodiment, the present invention provides a method of reducing the incidence of a WT1-expressing cancer, or its relapse, in a subject, the method comprising administering to the subject a WT1 peptide or vaccine of the present invention, thereby reducing the incidence of a WT1-expressing cancer, or its relapse, in a subject.

In another embodiment, the present invention provides a method of inducing an anticancer immune response in a subject, the method comprising the step of contacting the subject with an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby inducing an anti-mesothelioma immune response in a subject. In one embodiment, the fragment of a WT1 protein is a peptide from among SEQ ID NO:6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55. In another embodiment the fragment consists of a peptide or comprises a peptide from among SEQ ID NO:6, 7, 30, 31, 32, 33, 34, 35, 36, 37, 38, 41, 42, 47 and 48, or SEQ ID NO: 8, 9, 10, 11, 12, 13, 14, 15, 16, 17, 18, 19, 20, 21, 22, 23, 39, 43, 44, 46, 49, 50 and 55. In another embodiment the HLA class I peptides consist of or comprise SEQ ID NO:6, 7, 30, 31, 32, 33, 34, 35, 36, 37, 38, 41, 42, 47 and 48, and the HLA class II peptide consists of or comprises SEQ ID NO:8, 9, 10, 11, 12, 13, 14, 15, 16, 17, 18, 19, 20, 21, 22, 23, 39, 43, 44, 46, 49, 50 and 55.

In another embodiment, the present invention provides a method of treating a subject with a cancer, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby treating a subject with a mesothelioma. In one embodiment, the fragment of a WT1 protein is a peptide from among SEQ ID NO:6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55.

In another embodiment, the present invention provides a method of reducing an incidence of a cancer, or its relapse, in a subject, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby reducing an incidence of a mesothelioma, or its relapse, in a subject. In one embodiment, the fragment of a WT1 protein is a peptide from among SEQ ID NO:6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55.

In another embodiment, the cancer is a WT1-expressing cancer. In one embodiment, the WT1-expressing cancer is an acute myelogenous leukemia (AML). In another embodiment, the WT1-expressing cancer is associated with a myelodysplastic syndrome (MDS). In another embodiment, the WT1-expressing cancer is an MDS. In another embodiment, the WT1-expressing cancer is a non-small cell lung cancer (NSCLC). In another embodiment, the WT1-expressing cancer is a Wilms' tumor. In another embodiment, the WT1-expressing cancer is a leukemia. In another embodiment, the WT1-expressing cancer is a hematological cancer. In another embodiment, the WT1-expressing cancer is a lymphoma. In another embodiment, the WT1-expressing cancer is a desmoplastic small round cell tumor. In another embodiment, the WT1-expressing cancer is a mesothelioma. In another embodiment, the WT1-expressing cancer is a malignant mesothelioma. In another embodiment, the WT1-expressing cancer is a gastric cancer. In another embodiment, the WT1-expressing cancer is a colon cancer. In another embodiment, the WT1-expressing cancer is a lung cancer. In another embodiment, the WT1-expressing cancer is a breast cancer. In another embodiment, the WT1-expressing cancer is a germ cell tumor. In another embodiment, the WT1-expressing cancer is an ovarian cancer. In another embodiment, the WT1-expressing cancer is a uterine cancer. In another embodiment, the WT1-expressing cancer is a thyroid cancer. In another embodiment, the WT1-expressing cancer is a hepatocellular carcinoma. In another embodiment, the WT1-expressing cancer is a thyroid cancer. In another embodiment, the WT1-expressing cancer is a liver cancer. In another embodiment, the WT1-expressing cancer is a renal cancer. In another embodiment, the WT1-expressing cancer is a Kaposi's sarcoma. In another embodiment, the WT1-expressing cancer is a sarcoma. In another embodiment, the WT1-expressing cancer is any other carcinoma or sarcoma.

In another embodiment, the WT1-expressing cancer is a solid tumor. In another embodiment, the solid tumor is associated with a WT1-expressing cancer. In another embodiment, the solid tumor is associated with a myelodysplastic syndrome (MDS). In another embodiment, the solid tumor is associated with a non-small cell lung cancer (NSCLC). In another embodiment, the solid tumor is associated with a lung cancer. In another embodiment, the solid tumor is associated with a breast cancer. In another embodiment, the solid tumor is associated with a colorectal cancer. In another embodiment, the solid tumor is associated with a prostate cancer. In another embodiment, the solid tumor is associated with an ovarian cancer. In another embodiment, the solid tumor is associated with a renal cancer. In another embodiment, the solid tumor is associated with a pancreatic cancer. In another embodiment, the solid tumor is associated with a brain cancer. In another embodiment, the solid tumor is associated with a gastrointestinal cancer. In another embodiment, the solid tumor is associated with a skin cancer. In another embodiment, the solid tumor is associated with a melanoma.

In another embodiment, the present invention provides a composition comprising an isolated peptide of the invention in combination with at least 1 additional WT1-derived peptide. In certain embodiments, a composition comprising at least 2 different isolated peptides of the present invention is provided. In certain embodiments, a composition comprising at least 3 or at least 4 different isolated peptides of the present invention is provided. Each possibility represents a separate embodiment of the present invention. In certain embodiments, the composition of the present invention is a vaccine.

In another embodiment, the present invention provides a method of treating a subject with a WT1-expressing cancer, the method comprising administering to the subject a peptide or composition of the present invention, thereby treating a subject with a WT1-expressing cancer.

In another embodiment, the present invention provides a method of reducing the incidence of a WT1-expressing cancer, or its relapse, in a subject, the method comprising administering to the subject a peptide or composition of the present invention, thereby reducing the incidence of a WT1-expressing cancer, or its relapse, in a subject.

In another embodiment, the present invention provides a method of inducing formation and proliferation of a WT1 protein-specific CTL, the method comprising contacting a lymphocyte population with a peptide or composition of the present invention, thereby inducing formation and proliferation of a WT1 protein-specific CTL. This method can be conducted in vitro, ex vivo or in vivo. When conducted in vitro or ex vivo, these CTL can then be infused into a patient for therapeutic effect.

In another embodiment, the present invention provides a method of inducing formation and proliferation of (a) a WT1 protein-specific $CD8^+$ lymphocyte; or (b) a $CD4^+$ lymphocyte specific for the WT1 protein, or the combination thereof, the method comprising contacting a lymphocyte population with a peptide or composition of the present invention, thereby inducing formation and proliferation of (a) a WT1 protein-specific $CD8^+$ lymphocyte; or (b) a $CD4^+$ lymphocyte specific for the WT1 protein; or a combination thereof. This method can be conducted in vitro, ex vivo or in vivo. When conducted in vitro or ex vivo, these CTL can then be infused into a patient for therapeutic effect.

"Peptide," in another embodiment of methods and compositions of the present invention, refers to a compound of subunit AA connected by peptide bonds. In another embodiment, the peptide comprises an AA analogue. In another embodiment, the peptide comprises a peptidomimetic. The different AA analogues and peptidomimetics that can be included in the peptides of methods and compositions of the present invention are enumerated hereinbelow. The subunits are, in another embodiment, linked by peptide bonds. In another embodiment, the subunit is linked by another type of bond, e.g. ester, ether, etc. Each possibility represents a separate embodiment of the present invention.

The unaltered peptides of the present invention (as described both above and below) are referred to collectively herein as "WT1 peptides." Each of the embodiments enumerated below for "WT1 peptides" applies to unaltered WT1 peptides and HLA class I and class II heteroclitic peptides of the present invention. Each possibility represents a separate embodiment of the present invention.

In another embodiment, a WT1 peptide of the present invention binds to an HLA class I molecule or a class II molecule. In another embodiment the peptide binds to both a class I and a class II molecule. In another embodiment, the HLA class II molecule is an HLA-DRB molecule. In another embodiment, the HLA class II-molecule is an HLA-DRA molecule. In another embodiment, the HLA molecule is an HLA-DQA1 molecule. In another embodiment, the HLA molecule is an HLA-DQB1 molecule. In another embodiment, the HLA molecule is an HLA-DPA1 molecule. In another embodiment, the HLA molecule is an HLA-DPB 1 molecule. In another embodiment, the HLA molecule is an HLA-DMA molecule. In another embodiment, the HLA molecule is an HLA-DMB molecule. In another embodiment, the HLA molecule is an HLA-DOA molecule. In another embodiment, the HLA molecule is an HLA-DOB molecule. In another embodiment, the HLA molecule is any other HLA class II-molecule known in the art. Each possibility represents a separate embodiment of the present invention.

In another embodiment, the HLA class I molecule whose binding motif is contained in or comprising a peptide of the present invention is, in another embodiment, an HLA-A molecule. In another embodiment, the HLA class I molecule is an HLA-B molecule. In another embodiment, the HLA class I molecule is an HLA-C molecule. In another embodiment, the HLA class I molecule is an HLA-A0201 molecule. In another embodiment, the molecule is HLA A1. In another embodiment, the HLA class I molecule is HLA A2. In another embodiment, the HLA class I molecule is HLA A2.1. In another embodiment, the HLA class I molecule is HLA A3. In another embodiment, the HLA class I molecule is HLA A3.2. In another embodiment, the HLA class I molecule is HLA A11. In another embodiment, the HLA class I molecule is HLA A24. In another embodiment, the HLA class I molecule is HLA B7. In another embodiment, the HLA class I molecule is HLA B27. In another embodiment, the HLA class I molecule is HLA B8. Each possibility represents a separate embodiment of the present invention.

In another embodiment, the HLA class I molecule-binding WT1-derived peptide of methods and compositions of the present invention binds to a superfamily of HLA class I molecules. In another embodiment, the superfamily is the A2 superfamily. In another embodiment, the superfamily is the A3 superfamily. In another embodiment, the superfamily is the A24 superfamily. In another embodiment, the superfamily is the B7 superfamily. In another embodiment, the superfamily is the B27 superfamily. In another embodiment, the superfamily is the B44 superfamily. In another embodiment, the superfamily is the C1 superfamily. In another embodiment, the superfamily is the C4 superfamily. In another embodiment, the superfamily is any other superfamily known in the art. Each possibility represents a separate embodiment of the present invention.

In another embodiment, the HLA molecule is a A0101, A0201, A0203, A2402, A6901, B0702, A3101, B3501, B3503, B3508, B3802, B3801, B3901, B4001, B4402, B4701, B5701, C0401, C1701, $DRB_1$0101, $DRB_1$0402, $DRB_1$0402, $DRB_1$0401 or $DRB_1$1104 molecule. In another embodiment, the peptides of SEQ ID NO:6, 7, 30, 31, 32, 33, 34, 35, 36, 37, 38, 41, 42, 47 and 48, and SEQ ID NO: 8, 9, 10, 11, 12, 13, 14, 15, 16, 17, 18, 19, 20, 21, 22, 23, 39, 43, 44, 46, 49, 50 and 55, bind to the HLA class I or class II molecules described for each peptide in the Tables below. In another embodiment the HLA class I peptides consist of or comprise SEQ ID NO:6, 7, 30, 31, 32, 33, 34, 35, 36, 37, 38, 41, 42, 47 and 48, and the HLA class II peptide consists of or comprises SEQ ID NO:8, 9, 10, 11, 12, 13, 14, 15, 16, 17, 18, 19, 20, 21, 22, 23, 39, 43, 44, 46, 49, 50 and 55, and bind to the corresponding HLA molecule or molecules indicated for each peptide in the tables below. In one embodiment, certain peptides can bind to more than one HLA allele.

In another embodiment, a modification of a peptide of the invention is provided. In one embodiment the modification comprises at least one heteroclitic amino acid change, also referred to as a mutation or mutated, or an anchor residue mutation (see below). An HLA class I molecule binding motif of a modified peptide of the present invention exhibits an increased affinity for the HLA class I molecule, relative to the unmutated counterpart of the peptide. In another embodiment, the point mutation increases the affinity of the isolated, mutated WT1-derived peptide for the HLA class I molecule. In another embodiment, the increase in affinity is relative to the affinity (for the same HLA class I molecule) of the isolated, unmutated WT1-derived peptide wherefrom the isolated, mutated WT1-derived peptide was derived. Each possibility represents a separate embodiment of the present invention.

In another embodiment, a WT1 peptide of methods and compositions of the present invention is so designed as to exhibit affinity for an HLA molecule. In another embodiment, the affinity is a high affinity, as described herein.

HLA molecules, known in another embodiment as major histocompatibility complex (MHC) molecules, bind peptides and present them to immune cells. Thus, in another embodiment, the immunogenicity of a peptide is partially determined by its affinity for HLA molecules. HLA class I molecules interact with CD8 molecules, which are generally present on cytotoxic T lymphocytes (CTL). HLA class II molecules interact with CD4 molecules, which are generally present on helper T lymphocytes.

In another embodiment, a peptide of the present invention is immunogenic. In another embodiment, "immunogenic" refers to an ability to stimulate, elicit or participate in an immune response. In another embodiment, the immune response elicited is a cell-mediated immune response. In another embodiment, the immune response is a combination of cell-mediated and humoral responses.

In another embodiment, T cells that bind to the MHC molecule-peptide complex become activated and induced to proliferate and lyse cells expressing a protein comprising the peptide. T cells are typically initially activated by "professional" antigen presenting cells ("APC"; e.g. dendritic cells, monocytes, and macrophages), which present costimulatory molecules that encourage T cell activation as opposed to anergy or apoptosis. In another embodiment, the response is heteroclitic, as described herein, such that the CTL lyses a neoplastic cell expressing a protein which has an AA sequence homologous to a peptide of this invention, or a different peptide than that used to first stimulate the T cell.

In another embodiment, an encounter of a T cell with a peptide of this invention induces its differentiation into an effector and/or memory T cell. Subsequent encounters between the effector or memory T cell and the same peptide, or, in another embodiment, with a related peptide of this invention, leads to a faster and more intense immune response. Such responses are gauged, in another embodiment, by measuring the degree of proliferation of the T cell population exposed to the peptide. In another embodiment, such responses are gauged by any of the methods enumerated hereinbelow.

In another embodiment, the peptides of methods and compositions of the present invention bind an HLA class II molecule with high affinity. In other embodiments, the HLA class II molecule is any HLA class II molecule enumerated herein. Each possibility represents a separate embodiment of the present invention.

In another embodiment, derivatives of peptides of methods and compositions of the present invention bind an HLA class I molecule with high affinity. In other embodiments, the MHC class I molecule is any MHC class I molecule enumerated herein. Each possibility represents a separate embodiment of the present invention.

In another embodiment, a peptide of methods and compositions of the present invention binds an HLA class II molecule with significant affinity, while a peptide derived from the original peptide binds an HLA class I molecule with significant affinity.

In another embodiment, "affinity" refers to the concentration of peptide necessary for inhibiting binding of a standard peptide to the indicated MHC molecule by 50%. In another embodiment, "high affinity" refers to an affinity is such that a concentration of about 500 nanomolar (nM) or less of the peptide is required for 50% inhibition of binding of a standard peptide. In another embodiment, a concentration of about 400 nM or less of the peptide is required. In another embodiment, the binding affinity is 300 nM. In another embodiment, the binding affinity is 200 nM. In another embodiment, the binding affinity is 150 nM. In another embodiment, the binding affinity is 100 nM. In another embodiment, the binding affinity is 80 nM. In another embodiment, the binding affinity is 60 nM. In another embodiment, the binding affinity is 40 nM. In another embodiment, the binding affinity is 30 nM. In another embodiment, the binding affinity is 20 nM. In another embodiment, the binding affinity is 15 nM. In another embodiment, the binding affinity is 10 nM. In another embodiment, the binding affinity is 8 nM. In another embodiment, the binding affinity is 6 nM. In another embodiment, the binding affinity is 4 nM. In another embodiment, the binding affinity is 3 nM. In another embodiment, the binding affinity is 2 nM. In another embodiment, the binding affinity is 1.5 nM. In another embodiment, the binding affinity is 1 nM. In another embodiment, the binding affinity is 0.8 nM. In another embodiment, the binding affinity is 0.6 nM. In another embodiment, the binding affinity is 0.5 nM. In another embodiment, the binding affinity is 0.4 nM. In another embodiment, the binding affinity is 0.3 nM. In another embodiment, the binding affinity is less than 0.3 nM.

In another embodiment, "affinity" refers to a measure of binding strength to the MHC molecule. In another embodiment, affinity is measured using a method known in the art to measure competitive binding affinities. In another embodiment, affinity is measured using a method known in the art to measure relative binding affinities. In another embodiment, the method is a competitive binding assay. In another embodiment, the method is radioimmunoassay or RIA. In another embodiment, the method is BiaCore analyses. In another embodiment, the method is any other method known in the art. In another embodiment, the method yields an IC50 in relation to an IC50 of a reference peptide of known affinity.

Each type of affinity and method of measuring affinity represents a separate embodiment of the present invention.

In another embodiment, "high affinity" refers to an IC50 of 0.5-500 nM. In another embodiment, the IC50 is 1-300 nM. In another embodiment, the IC50 is 1.5-200 nM. In another embodiment, the IC50 is 2-100 nM. In another embodiment, the IC50 is 3-100 nM. In another embodiment, the IC50 is 4-100 nM. In another embodiment, the IC50 is 6-100 nM. In another embodiment, the IC50 is 10-100 nM. In another embodiment, the IC50 is 30-100 nM. In another embodiment, the IC50 is 3-80 nM. In another embodiment, the IC50 is 4-60 nM. In another embodiment, the IC50 is 5-50 nM. In another embodiment, the IC50 is 6-50 nM. In another embodiment, the IC50 is 8-50 nM. In another embodiment, the IC50 is 10-50 nM. In another embodiment, the IC50 is 20-50 nM. In another embodiment, the IC50 is 6-40 nM. In another embodiment, the IC50 is 8-30 nM. In another embodiment, the IC50 is 10-25 nM. In another embodiment, the IC50 is 15-25 nM. Each affinity and range of affinities represents a separate embodiment of the present invention.

In another embodiment, a peptide of methods and compositions of the present invention binds to a superfamily of HLA molecules. Superfamilies of HLA molecules share very similar or identical binding motifs. In another embodiment, the superfamily is a HLA class I superfamily. In another embodiment, the superfamily is a HLA class II superfamily. Each possibility represents a separate embodiment of the present invention.

The terms "HLA-binding peptide," "HLA class I molecule-binding peptide," and "HLA class II molecule-binding peptide" refer, in another embodiment, to a peptide that binds an HLA molecule with measurable affinity. In another embodiment, the terms refer to a peptide that binds an HLA molecule with high affinity. In another embodiment, the terms refer to a peptide that binds an HLA molecule with sufficient affinity to activate a T cell precursor. In another embodiment, the terms refer to a peptide that binds an HLA molecule with sufficient affinity to mediate recognition by a T cell. The HLA molecule is, in other embodiments, any of the HLA molecules enumerated herein. Each possibility represents a separate embodiment of the present invention.

"Heteroclitic" refers, in another embodiment, to a peptide that generates an immune response that recognizes the original peptide from which the heteroclitic peptide was derived (e.g. the peptide not containing the anchor residue or other residue mutations). In another embodiment, "original peptide" refers to a peptide of the present invention. In another embodiment, "heteroclitic" refers to a peptide that generates an immune response that recognizes the original peptide from which the heteroclitic peptide was derived, wherein the immune response generated by vaccination with the heteroclitic peptide is greater than the immune response generated by vaccination with the original peptide. In another embodiment, a "heteroclitic" immune response refers to an immune response that recognizes the original peptide from which the improved peptide was derived (e.g. the peptide not containing the anchor residue mutations). In another embodiment, a "heteroclitic" immune response refers to an immune response that recognizes the original peptide from which the heteroclitic peptide was derived, wherein the magnitude of the immune response generated by vaccination with the heteroclitic peptide is greater than the immune response generated by vaccination with the original peptide. In another embodiment, the magnitude of the immune response generated by vaccination with the heteroclitic peptide is greater than the immune response substantially equal to the response to vaccination with the original peptide. In another embodiment, the magnitude of the immune response generated by vaccination with the heteroclitic peptide is greater than the immune response less than the response to vaccination with the original peptide. In another embodiment, a heteroclitic peptide of the present invention is an HLA class I heteroclitic peptide. Methods for identifying HLA class I and class II residues, and for improving HLA binding by mutating the residues, are well known in the art, as described below. Each possibility represents a separate embodiment of the present invention.

In another embodiment, a heteroclitic peptide of the present invention induces an immune response that is increased at least 2-fold relative to the WT1 peptide from which the heteroclitic peptide was derived ("native peptide"). In another embodiment, the increase is 3-fold relative to the native peptide. In another embodiment, the increase is 5-fold relative to the native peptide. In another embodiment, the increase is 7-fold relative to the native peptide. In another embodiment, the increase is 10-fold relative to the native peptide. In another embodiment, the increase is 15-fold relative to the native peptide. In another embodiment, the increase is 20-fold relative to the native peptide. In another embodiment, the increase is 30-fold relative to the native peptide. In another embodiment, the increase is 50-fold relative to the native peptide. In another embodiment, the increase is 100-fold relative to the native peptide. In another embodiment, the increase is 150-fold relative to the native peptide. In another embodiment, the increase is 200-fold relative to the native peptide. In another embodiment, the increase is 300-fold relative to the native peptide. In another embodiment, the increase is 500-fold relative to the native peptide. In another embodiment, the increase is 1000-fold relative to the native peptide. In another embodiment, the increase is more than 1000-fold relative to the native peptide. Each possibility represents a separate embodiment of the present invention.

In another embodiment, the present invention provides a HLA class II heteroclitic peptide derived from an isolated WT1 peptide of the present invention. In another embodiment, the process of deriving comprises introducing a mutation that enhances a binding of the peptide to an HLA class II molecule. In another embodiment, the process of deriving consists of introducing a mutation that enhances a binding of the peptide to an HLA class I molecule. In another embodiment, the mutation is in an HLA class II anchor residue. In another embodiment, a heteroclitic class II peptide of the present invention is identified and tested in a manner analogous to identification and testing of HLA class I heteroclitic peptides, as exemplified herein. Each possibility represents a separate embodiment of the present invention.

In another embodiment, the HLA class II binding site in a peptide of the present invention is created or improved by mutation of an HLA class II motif anchor residue. In another embodiment, the anchor residue that is modified is in the P1 position. In another embodiment, the anchor residue is at the P2 position. In another embodiment, the anchor residue is at the P6 position. In another embodiment, the anchor residue is at the P9 position. In another embodiment, the anchor residue is selected from the P1, P2, P6, and P9 positions. In another embodiment, the anchor residue is at the P3 position. In another embodiment, the anchor residue is at the P4 position. In another embodiment, the anchor residue is at the P5 position. In another embodiment, the anchor residue is at the P6 position. In another embodiment, the anchor residue is at the P8 position. In another embodiment, the anchor residue is at the P10 position. In another embodiment, the anchor residue is at the P11 position. In another embodiment, the anchor residue is at the P12 position. In another embodiment, the anchor residue is at the P13 position. In another embodiment, the anchor residue is at any other anchor residue of an HLA class II molecule that is known in the art. In another embodiment, residues other than P1, P2, P6, and P9 serve as secondary anchor residues; therefore, mutating them can improve HLA class II binding. Each possibility represents a separate embodiment of the present invention.

In another embodiment, a heteroclitic peptide is generated by introduction of a mutation that creates an anchor motif. "Anchor motifs" or "anchor residues" refers, in another embodiment, to 1 or a set of preferred residues at particular positions in an HLA-binding sequence. In another embodiment, the HLA-binding sequence is an HLA class II-binding sequence. In another embodiment, the HLA-binding sequence is an HLA class I-binding sequence. In another embodiment, the positions corresponding to the anchor motifs are those that play a significant role in binding the HLA molecule. In another embodiment, the anchor residue is a primary anchor motif. In another embodiment, the anchor residue is a secondary anchor motif. Each possibility represents a separate embodiment of the present invention.

Methods for predicting MHC class I and II epitopes are well known in the art. In one embodiment, the software of the Bioinformatics & Molecular Analysis Section (National Institutes of Health, Washington, DC) available at http://bimas.dcrt.nih.gov/cgi-bin/molbio/ken parker comboform is useful. This software ranks 9-mer or 10-mer peptides on a predicted half-time dissociation coefficient from HLA class I molecules (Pinilla, et al. Curr Opin Immunol, 11 (2): p. 193-202 (1999)). In another embodiment, MHC class II epitope is predicted using TEPITOPE (Meister G E, Roberts C G et al, Vaccine 1995 13: 581-91). In another embodiment, the MHC class II epitope is predicted using EpiMatrix (De Groot A S, Jesdale B M et al, AIDS Res Hum Retroviruses 1997 13: 529-31). In another embodiment, the MHC class II epitope is predicted using the Predict Method (Yu K, Petrovsky N et al, Mol Med. 2002 8: 137-48). In another embodiment, the MHC class II epitope is predicted using the SYFPEITHI epitope prediction algorithm (Examples). In another embodiment, the MHC class II epitope is predicted using Rankpep. In another embodiment, the MHC class II epitope is predicted using any other method known in the art. Each possibility represents a separate embodiment of the present invention.

In another embodiment, in the case of HLA class II-binding peptides (e.g. HLA-DR-binding peptides), the anchor residue that is modified is in the P1 position. In another embodiment, the anchor residue is in the P2 position. In another embodiment, the anchor residue is in the P6 position. In another embodiment, the anchor residue is in the P9 position. In other embodiments, the anchor residue is the P3, P4, P5, P6, P8, P10, P11, P12, or P13 position. In another embodiment, the anchor residue is any other anchor residue of an HLA class II molecule that is known in the art. In another embodiment, residues other than P1, P2, P6, and P9 serve as secondary anchor residues; therefore, mutating them can improve HLA class II binding. In another embodiment, any combination of the above residues is mutated. Each possibility represents a separate embodiment of the present invention.

In another embodiment, a WT1 peptide of the present invention binds to 2 distinct HLA class II molecules. In another embodiment, the peptide binds to three distinct HLA class II molecules. In another embodiment, the peptide binds to four distinct HLA class II molecules. In another embodiment, the peptide binds to five distinct HLA class II molecules. In another embodiment, the peptide binds to six distinct HLA class II molecules. In another embodiment, the peptide binds to more than six distinct HLA class II molecules.

In another embodiment, the HLA class II molecules that are bound by a WT1 peptide of the present invention are encoded by two or more distinct alleles at a given HLA class II locus. In another embodiment, the HLA class II molecules are encoded by 3 distinct alleles at a locus. In another embodiment, the HLA class II molecules are encoded by 4 distinct alleles at a locus. In another embodiment, the HLA class II molecules are encoded by 5 distinct alleles at a locus. In another embodiment, the HLA class II molecules are encoded by 6 distinct alleles at a locus. In another embodiment, the HLA class II molecules are encoded by more than six distinct alleles at a locus.

In another embodiment, the HLA class II molecules bound by the WT1 peptide are encoded by HLA class II genes at 2 distinct loci. In another embodiment, the HLA molecules bound are encoded by HLA class II genes at 2 or more distinct loci. In another embodiment, the HLA molecules bound are encoded by HLA class II genes at 3 distinct loci. In another embodiment, the HLA molecules bound are encoded by HLA class II genes at 3 or more distinct loci. In another embodiment, the HLA molecules bound are encoded by HLA class II genes at 4 distinct loci. In another embodiment, the HLA molecules bound are encoded by HLA class II genes at 4 or more distinct loci. In another embodiment, the HLA molecules bound are encoded by HLA class II genes at more than 4 distinct loci. In other embodiments, the loci are selected from HLA-DRB loci. In another embodiment, the HLA class II-binding peptide is an HLA-DRA binding peptide. In another embodiment, the peptide is an HLA-DQA1 binding peptide. In another embodiment, the peptide is an HLA-DQB 1 binding peptide. In another embodiment, the peptide is an HLA-DPA1 binding peptide. In another embodiment, the peptide is an HLA-DPB 1 binding peptide. In another embodiment, the peptide is an HLA-DMA binding peptide. In another embodiment, the peptide is an HLA-DMB binding peptide. In another embodiment, the peptide is an HLA-DOA binding peptide. In another embodiment, the peptide is an HLA-DOB binding peptide. In another embodiment, the peptide binds to any other HLA class II molecule known in the art. Each possibility represents a separate embodiment of the present invention.

In another embodiment, a WT1 peptide of the present invention binds to 2 distinct HLA-DRB molecules. In another embodiment, the peptide binds to 3 distinct HLA-DRB molecules. In another embodiment, the peptide binds to 4 distinct HLA-DRB molecules. In another embodiment, the peptide binds to 5 distinct HLA-DRB molecules. In another embodiment, the peptide binds to 6 distinct HLA-DRB molecules. In another embodiment, the peptide binds to more than 6 distinct HLA-DRB molecules.

In another embodiment, a WT1 peptide of the present invention binds to HLA-DRB molecules that are encoded by 2 distinct HLA-DRB alleles. In another embodiment, the HLA-DRB molecules are encoded by 3 distinct HLA-DRB alleles. In another embodiment, the HLA-DRB molecules are encoded by 4 distinct HLA-DRB alleles. In another embodiment, the HLA-DRB molecules are encoded by 5 distinct HLA-DRB alleles. In another embodiment, the HLA-DRB molecules are encoded by 6 distinct HLA-DRB alleles. In another embodiment, the HLA-DRB molecules are encoded by more than 6 distinct HLA-DRB alleles. Each possibility represents a separate embodiment of the present invention.

In another embodiment, a WT1 peptide of the present invention binds to HLA-DRB molecules that are encoded by 2 distinct HLA-DRB alleles selected from DRB 101, DRB 301, DRB 401, DRB 701, DRB 1101, and DRB 1501. In another embodiment, the WT1 peptide binds to HLA-DRB molecules encoded by 3 distinct HLA-DRB alleles selected from DRB 101, DRB 301, DRB 401, DRB 701, DRB 1101, and DRB 1501. In another embodiment, the WT1 peptide binds to HLA-DRB molecules encoded by 4 distinct HLA-DRB alleles selected from DRB 101, DRB 301, DRB 401, DRB 701, DRB 1101, and DRB 1501. In another embodiment, the WT1 peptide binds to HLA-DRB molecules encoded by 5 distinct HLA-DRB alleles selected from DRB 101, DRB 301, DRB 401, DRB 701, DRB 1101, DRB 1104 and DRB 1501. In another embodiment, the WT1 peptide binds to HLA-DRB molecules encoded by each of the following HLA-DRB alleles: DRB 101, DRB 301, DRB 401, DRB 701, DRB 1101, and DRB 1501. Each possibility represents a separate embodiment of the present invention.

In another embodiment, the present invention provides a composition comprising 2 distinct WT1 peptides of the present invention. In another embodiment, the 2 distinct WT1 peptides are both unaltered. In another embodiment, 1 of the WT1 peptides is unaltered, while the other is heteroclitic. In another embodiment, both of the WT1 peptides are heteroclitic.

In another embodiment, the composition comprises 3 distinct WT1 peptides of the present invention. In another embodiment, the composition comprises 4 distinct WT1 peptides of the present invention. In another embodiment, the composition comprises 5 distinct WT1 peptides of the present invention. In another embodiment, the composition comprises more than 5 distinct isolated WT1 peptides of the present invention.

In another embodiment, 2 of the WT1 peptides in the composition are unaltered. In another embodiment, 2 of the WT1 peptides in the composition are heteroclitic. In another embodiment, 2 of the WT1 peptides in the composition are unaltered, and 2 are heteroclitic. In another embodiment, more than 2 of the WT1 peptides in the composition are unaltered. In another embodiment, more than 2 of the WT1 peptides in the composition are heteroclitic. In another embodiment, more than 2 of the WT1 peptides in the composition are unaltered, and more than 2 are heteroclitic. Each possibility represents a separate embodiment of the present invention.

In another embodiment, 1 of the additional WT1 peptides in a composition of the present invention has a sequence selected from the sequences set forth in SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55. In another embodiment, 2 of the additional WT1 peptides have a sequence selected from the sequences set forth in SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55. In another embodiment, 3 of the additional WT1 peptides have a sequence selected from the sequences set forth in SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55.

In another embodiment, any other immunogenic WT1 peptide known in the art is utilized as an additional WT1 peptide. In another embodiment, any combination of immunogenic WT1 peptides known in the art is utilized. Non-limiting sources of other WT1 peptides include WO2005053618, WO2007047764 and WO2007120673.

Each additional WT1 peptide, and each combination thereof, represents a separate embodiment of the present invention.

In another embodiment, a composition of the present invention contains 2 HLA class II heteroclitic peptides that are derived from the same isolated WT1 peptide of the present invention. In another embodiment, the 2 HLA class II heteroclitic peptides contain mutations in different HLA class II molecule anchor residues. In another embodiment, the 2 HLA class II heteroclitic peptides contain different mutations in the same anchor residues. In another embodiment, 2 of the HLA class II heteroclitic peptides are derived from different isolated WT1 peptides of the present invention. Each possibility represents a separate embodiment of the present invention.

In another embodiment, 2 WT1 peptides of the present invention, or the WT1 peptides that correspond to two HLA class II heteroclitic peptides of the present invention, overlap with one another. In another embodiment, the overlap between the peptides is at least 7 amino acids (AA). In another embodiment, the overlap is at least 8 AA. In another embodiment, the overlap is at least 9 AA. In another embodiment, the overlap is 7 AA. In another embodiment, the overlap is 8 AA. In another embodiment, the overlap is 9 AA. In another embodiment, the overlap is 10 AA. In another embodiment, the overlap is 11 AA. In another embodiment, the overlap is 12 AA. In another embodiment, the overlap is 13 AA. In another embodiment, the overlap is 14 AA. In another embodiment, the overlap is 15 AA. In another embodiment, the overlap is 16 AA. In another embodiment, the overlap is more than 16 AA. Each possibility represents a separate embodiment of the present invention.

In another embodiment, the peptides in a composition of the present invention bind to 2 distinct HLA class II molecules. In another embodiment, the peptides bind to 3 distinct HLA class II molecules. In another embodiment, the peptides bind to 4 distinct HLA class II molecules. In another embodiment, the peptides bind to 5 distinct HLA class II molecules. In another embodiment, the peptides bind to more than 5 distinct HLA class II molecules. In another embodiment, the peptides in the composition bind to the same HLA class II molecules.

In another embodiment, each of the WT 1 peptides in a composition of the present invention binds to a set of HLA class II molecules. In another embodiment, each of the WT1 peptides binds to a distinct set of HLA class II molecules. In another embodiment, the WT1 peptides in the composition bind to the same set of HLA class II molecules. In another embodiment, 2 of the WT1 peptides bind to a distinct but overlapping set of HLA class II molecules. In another embodiment, 2 or more of the WT1 peptides bind to the same set of HLA class II molecules, while another of the WT1 peptides binds to a distinct set. In another embodiment, 2 or more of the WT1 peptides bind to an overlapping set of HLA class II molecules, while another of the WT1 peptides binds to a distinct set.

In another embodiment, 2 or more of the WT1 peptides in a composition of the present invention each binds to more than 1 HLA-DRB molecule. In another embodiment, the 4 or more HLA-DRB molecules bound by the peptides in the composition are distinct from one another. In another embodiment, the HLA-DRB molecules are encoded by different HLA-DRB alleles. Each possibility represents a separate embodiment of the present invention.

In another embodiment, 2 or more of the HLA class II molecules bound by WT1 peptides in a composition of the present invention are HLA-DRB molecules. In another embodiment, 3 or more of the HLA class II molecules that are bound are HLA-DRB molecules. In other embodiments, the HLA class II molecules that are bound can be any of the HLA class II molecules enumerated herein. In another embodiment, the HLA class II molecules that are bound are encoded by 2 or more distinct HLA class II alleles at a given locus. In another embodiment, the HLA class II molecules that are bound are encoded by HLA class II genes at 2 or more distinct loci.

Each of the above compositions represents a separate embodiment of the present invention.

In another embodiment, a "set of HLA class II molecules" refers to the HLA class II molecules encoded by different alleles at a particular locus. In another embodiment, the term refers to HLA class II molecules with a particular binding specificity. In another embodiment, the term refers to HLA class II molecules with a particular peptide consensus sequence. In another embodiment, the term refers to a superfamily of HLA class II molecules. Each possibility represents a separate embodiment of the present invention.

In another embodiment, the present invention provides a composition comprising an unaltered HLA class II molecule-binding WT1 peptide of the present invention and a second, HLA class I molecule-binding WT1 peptide. In another embodiment, the composition comprises more than 1 HLA class II molecule-binding WT1 peptide of the present invention, in addition to the HLA class I molecule-binding WT1 peptide. In another embodiment, the composition comprises more than 1 HLA class I molecule-binding WT1 peptide, in addition to the HLA class II molecule-binding WT1 peptide. Each possibility represents a separate embodiment of the present invention.

In another embodiment, the AA sequence of the HLA class I molecule-binding WT1 peptide comprises a sequence selected from SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55. In another embodiment, the AA sequence of the HLA class I molecule-binding WT1 peptide is selected from the sequences set forth in SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55. Each possibility represents a separate embodiment of the present invention.

In another embodiment, the HLA class I molecule-binding WT1 peptide is an HLA class I heteroclitic peptide. In another embodiment, the HLA class I molecule-binding WT1 peptide contains a mutation in an HLA class I molecule anchor residue thereof, as described further herein. As provided herein, WT1-derived peptides were modified in HLA anchor residues to generate heteroclitic peptides with increased predicted binding to HLA-A0201 and HLA-A0301. Peptides with increased predicted binding also exhibited enhanced ability to bind HLA class I molecules and increased immunogenicity.

In another embodiment, the mutation that enhances MHC binding is in the residue at position 1 of the HLA class I heteroclitic peptide. In another embodiment, the residue is changed to tyrosine. In another embodiment, the residue is changed to glycine. In another embodiment, the residue is changed to threonine. In another embodiment, the residue is changed to phenylalanine. In another embodiment, the residue is changed to any other residue known in the art. In another embodiment, a substitution in position 1 (e.g. to tyrosine) stabilizes the binding of the position 2 anchor residue.

In another embodiment, the mutation is in position 2 of the HLA class I heteroclitic peptide. In another embodiment, the residue is changed to leucine. In another embodiment, the residue is changed to valine. In another embodiment, the residue is changed to isoleucine. In another embodiment, the residue is changed to methionine. In another embodiment, the residue is changed to any other residue known in the art.

In another embodiment, the mutation is in position 6 of the HLA class I heteroclitic peptide. In another embodiment, the residue is changed to valine. In another embodiment, the residue is changed to cysteine. In another embodiment, the residue is changed to glutamine. In another embodiment, the residue is changed to histidine. In another embodiment, the residue is changed to any other residue known in the art.

In another embodiment, the mutation is in position 9 of the HLA class I heteroclitic peptide. In another embodiment, the mutation changes the residue at the C-terminal position thereof. In another embodiment, the residue is changed to valine. In another embodiment, the residue is changed to threonine. In another embodiment, the residue is changed to isoleucine. In another embodiment, the residue is changed to leucine. In another embodiment, the residue is changed to alanine. In another embodiment, the residue is changed to cysteine. In another embodiment, the residue is changed to any other residue known in the art.

In another embodiment, the point mutation is in a primary anchor residue. In another embodiment, the HLA class I primary anchor residues are positions 2 and 9. In another embodiment, the point mutation is in a secondary anchor residue. In another embodiment, the HLA class I secondary anchor residues are positions 1 and 8. In another embodiment, the HLA class I secondary anchor residues are positions 1, 3, 6, 7, and 8. In another embodiment, the point mutation is in a position selected from positions 4, 5, and 8. Each possibility represents a separate embodiment of the present invention.

In another embodiment, the point mutation is in 1 or more residues in positions selected from positions 1, 2, 8, and 9 of the HLA class I binding motif. In another embodiment, the point mutation is in 1 or more residues in positions selected from positions 1, 3, 6, and 9. In another embodiment, the point mutation is in 1 or more residues in positions selected from positions 1, 2, 6, and 9. In another embodiment, the point mutation is in 1 or more residues in positions selected from positions 1, 6, and 9. In another embodiment, the point mutation is in 1 or more residues in positions selected from positions 1, 2, and 9. In another embodiment, the point mutation is in 1 or more residues in positions selected from positions 1, 3, and 9. In another embodiment, the point mutation is in 1 or more residues in positions selected from positions 2 and 9. In another embodiment, the point mutation is in 1 or more residues in positions selected from positions 6 and 9. Each possibility represents a separate embodiment of the present invention.

Each of the above anchor residues and substitutions represents a separate embodiment of the present invention.

In another embodiment, the HLA class I molecule-binding WT peptide has length of 9 AA. In another embodiment, the peptide has length of 10 AA. As provided herein, native and heteroclitic peptides of 9-10 AA exhibited substantial binding to HLA class I molecules and ability to elicit cytokine secretion and cytolysis by CTL.

In another embodiment, the HLA class I molecule that is bound by the HLA class I molecule-binding WT1 peptide is an HLA-A molecule. In another embodiment, the HLA class I-molecule is an HLA-A2 molecule. In another embodiment, the HLA class I-molecule is an HLA-A3 molecule. In another embodiment, the HLA class I-molecule is an HLA-A11 molecule. In another embodiment, the HLA class I-molecule is an HLA-B 8 molecule. In another embodiment, the HLA class I-molecule is an HLA-0201 molecule. In another embodiment, the HLA class I-molecule binds any other HLA class I molecule known in the art. Each possibility represents a separate embodiment of the present invention.

In another embodiment, a WT1 peptide of methods and compositions of the present invention has a length of 8-30 amino acids. In another embodiment, the peptide has a length of 9-11 AA. In another embodiment, the peptide ranges in size from 7-25 AA, or in another embodiment, 8-11, or in another embodiment, 8-15, or in another embodiment, 9-20, or in another embodiment, 9-18, or in another embodiment, 9-15, or in another embodiment, 8-12, or in another embodiment, 9-11 AA in length. In another embodiment, the peptide is 8 AA in length, or in another embodiment, 9 AA or in another embodiment, 10 AA or in another embodiment, 12 AA or in another embodiment, 25 AA in length, or in another embodiment, any length therebetween. In another embodiment, the peptide is of greater length, for example 50, or 100, or more. In this embodiment, the cell processes the peptide to a length of 7 and 25 AA in length. In this embodiment, the cell processes the peptide to a length of 9-11 AA Each possibility represents a separate embodiment of the present invention.

In another embodiment, the peptide is 15-23 AA in length. In another embodiment, the length is 15-24 AA. In another embodiment, the length is 15-25 AA. In another embodiment, the length is 15-26 AA. In another embodiment, the length is 15-27 AA. In another embodiment, the length is 15-28 AA. In another embodiment, the length is 14-30 AA. In another embodiment, the length is 14-29 AA. In another embodiment, the length is 14-28 AA. In another embodiment, the length is 14-26 AA. In another embodiment, the length is 14-24 AA. In another embodiment, the length is 14-22 AA. In another embodiment, the length is 14-20 AA. In another embodiment, the length is 16-30 AA. In another embodiment, the length is 16-28 AA. In another embodiment, the length is 16-26 AA. In another embodiment, the length is 16-24 AA. In another embodiment, the length is 16-22 AA. In another embodiment, the length is 18-30 AA. In another embodiment, the length is 18-28 AA. In another embodiment, the length is 18-26 AA. In another embodiment, the length is 18-24 AA. In another embodiment, the length is 18-22 AA. In another embodiment, the length is 18-20 AA. In another embodiment, the length is 20-30 AA. In another embodiment, the length is 20-28 AA. In another embodiment, the length is 20-26 AA. In another embodiment, the length is 20-24 AA. In another embodiment, the length is 22-30 AA. In another embodiment, the length is 22-28 AA. In another embodiment, the length is 22-26 AA. In another embodiment, the length is 24-30 AA. In another embodiment, the length is 24-28 AA. In another embodiment, the length is 24-26 AA.

Each of the above peptides, peptide lengths, and types of peptides represents a separate embodiment of the present invention.

In another embodiment, minor modifications are made to peptides of the present invention without decreasing their affinity for HLA molecules or changing their TCR specificity, utilizing principles well known in the art. In the case of HLA class I-binding peptides, "minor modifications" refers, in another embodiment, to e.g. insertion, deletion, or substitution of one AA, inclusive, or deletion or addition of 1-3 AA outside of the residues between 2 and 9, inclusive. While the computer algorithms described herein are useful for predicting the MHC class I-binding potential of peptides, they have 60-80% predictive accuracy; and thus, the peptides should be evaluated empirically before a final determination of MHC class I-binding affinity is made. Thus, peptides of the present invention are not limited to peptides predicated by the algorithms to exhibit strong MHC class I-binding affinity. The types are modifications that can be made are listed below. Each modification represents a separate embodiment of the present invention.

In another embodiment, a peptide enumerated in the Examples of the present invention is further modified by mutating an anchor residue to an MHC class I preferred anchor residue, which can be, in other embodiments, any of the anchor residues enumerated herein. In another embodiment, a peptide of the present invention containing an MHC class I preferred anchor residue is further modified by mutating the anchor residue to a different MHC class I preferred residue for that location. The different preferred residue can be, in other embodiments, any of the preferred residues enumerated herein.

In another embodiment, the anchor residue that is further modified is in the 1 position. In another embodiment, the anchor residue is in the 2 position. In another embodiment, the anchor residue is in the 3 position. In another embodiment, the anchor residue is in the 4 position. In another embodiment, the anchor residue is in the 5 position. In another embodiment, the anchor residue is in the 6 position. In another embodiment, the anchor residue is in the 7 position. In another embodiment, the anchor residue is in the 8 position. In another embodiment, the anchor residue is in the 9 position. In the case of HLA class I-binding peptides, residues other than 2 and 9 can serve as secondary anchor residues; therefore, mutating them can improve MHC class I binding. Each possibility represents a separate embodiment of the present invention.

In another embodiment, a peptide of methods and compositions of the present invention is a length variant of a peptide enumerated in the Examples. In another embodiment, the length variant is one amino acid (AA) shorter than the peptide from the Examples. In another embodiment, the length variant is two AA shorter than the peptide from the Examples. In another embodiment, the length variant is more than two AA shorter than the peptide from the Examples. In another embodiment, the shorter peptide is truncated on the N-terminal end. In another embodiment, the shorter peptide is truncated on the C-terminal end. In another embodiment, the truncated peptide is truncated on both the N-terminal and C-terminal ends. Peptides are, in another embodiment, amenable to truncation without changing affinity for HLA molecules, as is well known in the art.

Each of the above truncated peptides represents a separate embodiment of the present invention.

In another embodiment, the length variant is longer than a peptide enumerated in the Examples of the present invention. In another embodiment, the longer peptide is extended on the N-terminal end in accordance with the surrounding WT1 sequence. Peptides are, in another embodiment, amenable to extension on the N-terminal end without changing affinity for HLA molecules, as is well known in the art. Such peptides are thus equivalents of the peptides enumerated in the Examples. In another embodiment, the N-terminal extended peptide is extended by one residue. In another embodiment, the N-terminal extended peptide is extended by two residues. In another embodiment, the N-terminal extended peptide is extended by three residues. In another embodiment, the N-terminal extended peptide is extended by more than three residues.

In another embodiment, the longer peptide is extended on the C terminal end in accordance with the surrounding WT1 sequence. Peptides are, in another embodiment, amenable to extension on the C-terminal end without changing affinity for HLA molecules, as is well known in the art. Such peptides are thus equivalents of the peptides enumerated in the Examples of the present invention. In another embodiment, the C-terminal extended peptide is extended by one residue. In another embodiment, the C-terminal extended peptide is extended by two residues. In another embodiment, the C-terminal extended peptide is extended by three residues. In another embodiment, the C-terminal extended peptide is extended by more than three residues.

In another embodiment, the extended peptide is extended on both the N-terminal and C-terminal ends in accordance with the surrounding WT1 sequence.

Each of the above extended peptides represents a separate embodiment of the present invention.

In another embodiment, a truncated peptide of the present invention retains the HLA anchor residues (e.g. the HLA class I anchor residues) on the second residue and the C-terminal residue, with a smaller number of intervening residues (e.g., 5) than a peptide enumerated in the Examples of the present invention. Peptides are, in another embodiment, amenable to such mutation without changing affinity for HLA molecules. In another embodiment, such a truncated peptide is designed by removing one of the intervening residues of one of the above sequences. In another embodiment, the HLA anchor residues are retained on the second and eighth residues. In another embodiment, the HLA anchor residues are retained on the first and eighth residues. Each possibility represents a separate embodiment of the present invention.

In another embodiment, an extended peptide of the present invention retains the HLA anchor residues (e.g. the HLA class I anchor residues) on the second residue and the C-terminal residue, with a larger number of intervening residues (e.g. 7 or 8) than a peptide enumerated in the Examples of the present invention. In another embodiment, such an extended peptide is designed by adding one or more residues between two of the intervening residues of one of the above sequences. It is well known in the art that residues can be removed from or added between the intervening sequences of HLA-binding peptides without changing affinity for HLA. Such peptides are thus equivalents of the peptides enumerated in the Examples of the present invention. In another embodiment, the HLA anchor residues are retained on the second and ninth residues. In another embodiment, the HLA anchor residues are retained on the first and eighth residues. In another embodiment, the HLA anchor residues are retained on the two residues separated by six intervening residues. Each possibility represents a separate embodiment of the present invention.

"Fragment," in another embodiment, refers to a peptide of 11 or more AA in length. In another embodiment, a peptide fragment of the present invention is 16 or more AA long. In another embodiment, the fragment is 12 or more AA long. In another embodiment, the fragment is 13 or more AA. In another embodiment, the fragment is 14 or more AA. In another embodiment, the fragment is 15 or more AA. In another embodiment, the fragment is 17 or more AA. In another embodiment, the fragment is 18 or more AA. In another embodiment, the fragment is 19 or more AA. In another embodiment, the fragment is 22 or more AA. In another embodiment, the fragment is 8-12 AA. In another embodiment, the fragment is about 8-12 AA. In another embodiment, the fragment is 16-19 AA. In another embodiment, the fragment is about 16-19 AA. In another embodiment, the fragment 10-25 AA. In another embodiment, the fragment is about 10-25 AA. In another embodiment, the fragment has any other length. Each possibility represents a separate embodiment of the present invention.

"Fragment of a WT1 protein," in another embodiment, refers to any of the definitions of "fragment" found herein. Each definition represents a separate embodiment of the present invention.

In another embodiment, a peptide of the present invention is homologous to a peptide enumerated in the Examples. The terms "homology," "homologous," etc., when in reference to any protein or peptide, refer, in another embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

Homology is, in another embodiment, determined by computer algorithm for sequence alignment, by methods well described in the art. In other embodiments, computer algorithm analysis of nucleic acid sequence homology includes the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 70%. In another embodiment, "homology" refers to identity to a sequence selected from SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 72%. In another embodiment, "homology" refers to identity to one of SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 75%. In another embodiment, "homology" refers to identity to a sequence selected from SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 78%. In another embodiment, "homology" refers to identity to one of SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 80%. In another embodiment, "homology" refers to identity to one of SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 82%. In another embodiment, "homology" refers to identity to a sequence selected from SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 83%. In another embodiment, "homology" refers to identity to one of SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 85%. In another embodiment, "homology" refers to identity to one of SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 87%. In another embodiment, "homology" refers to identity to a sequence selected from SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than [0128] 88%. In another embodiment, "homology" refers to identity to one of SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 90%. In another embodiment, "homology" refers to identity to one of SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 92%. In another embodiment, "homology" refers to identity to a sequence selected from SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 93%. In another embodiment, "homology" refers to identity to one of SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 95%. In another embodiment, "homology" refers to identity to a sequence selected from SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 96%. In another embodiment, "homology" refers to identity to one of SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 97%. In another embodiment, "homology" refers to identity to one of SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 98%. In another embodiment, "homology" refers to identity to one of SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of greater than 99%. In another embodiment, "homology" refers to identity to one of SEQ ID No: 6, 7, 8, 9, 10, 11, 12, 13, 14, 15, 16, 17, 18, 19, 20, 21, 22, 23, 30, 31, 32, 33, 35, 36, 37, 38, 39, 41, 42, 43, 44, 46, 47, 48, 49, 50 and 55 of 100%. Each possibility represents a separate embodiment of the present invention. [00114] In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N. Y.; and Ausubel et al., 1989, Current Protocols in Molecular Biology, Green Publishing Associates and Wiley Interscience, N. Y). In another embodiments, methods of hybridization are carried out under moderate to stringent conditions, to the complement of a DNA encoding a native caspase peptide. Hybridization conditions being, for example, overnight incubation at 42<0>C in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 [mu]g/ml denatured, sheared salmon sperm DNA.

Each of the above homologues and variants of peptides enumerated in the Examples represents a separate embodiment of the present invention.

In another embodiment, the present invention provides a composition comprising a peptide of this invention. In another embodiment, the composition further comprises a pharmaceutically acceptable carrier. In another embodiment, the composition further comprises an adjuvant. In another embodiment, the composition comprises 2 or more peptides of the present invention. In another embodiment, the composition further comprises any of the additives, compounds, or excipients set forth hereinbelow. In another embodiment, the adjuvant is KLH, QS21, Freund's complete or incomplete adjuvant, aluminum phosphate, aluminum hydroxide, BCG or alum. In other embodiments, the carrier is any carrier enumerated herein. In other embodiments, the adjuvant is any adjuvant enumerated herein. Each possibility represents a separate embodiment of the present invention.

In another embodiment, this invention provides a vaccine comprising a peptide of this invention. In another embodiment, this invention provides a vaccine comprising an antigen-presenting cell (APC) and a peptide of this invention. In another embodiment, the vaccine further comprises a carrier. In another embodiment, the vaccine further comprises an adjuvant. In another embodiment, the vaccine further comprises an APC. In another embodiment, the vaccine further comprises a combination of more than 1 of an antigen, carrier, and/or APC. In another embodiment, the vaccine is a cell-based composition. Each possibility represents a separate embodiment of the present invention.

In another embodiment, the term "vaccine" refers to a material or composition that, when introduced into a subject, provides a prophylactic or therapeutic response for a particular disease, condition, or symptom of same. In another embodiment, this invention comprises peptide-based vaccines, wherein the peptide comprises any embodiment listed herein, including immunomodulating compounds such as cytokines, adjuvants, etc.

In another embodiment, a vaccine of methods and compositions of the present invention further comprises an adjuvant. In another embodiment, the adjuvant is Montanide ISA 51. Montanide ISA 51 contains a natural metabolizable oil and a refined emulsifier. In another embodiment, the adjuvant is GM-CSF. Recombinant GM-CSF is a human protein grown, in another embodiment, in a yeast (*S. cerevisiae*) vector. GM-CSF promotes clonal expansion and differentiation of hematopoietic progenitor cells, APC, and dendritic cells and T cells.

In another embodiment, the adjuvant is a cytokine. In another embodiment, the adjuvant is a growth factor. In another embodiment, the adjuvant is a cell population. In another embodiment, the adjuvant is QS21. In another embodiment, the adjuvant is Freund's incomplete adjuvant. In another embodiment, the adjuvant is aluminum phosphate. In another embodiment, the adjuvant is aluminum hydroxide. In another embodiment, the adjuvant is BCG. In another embodiment, the adjuvant is alum.

In another embodiment, the adjuvant is an interleukin. In another embodiment, the adjuvant is a chemokine. In another embodiment, the adjuvant is any other type of adjuvant known in the art. In another embodiment, the WT1 vaccine comprises two the above adjuvants. In another embodiment, the WT1 vaccine comprises more than two the above adjuvants. Each possibility represents a separate embodiment of the present invention.

In other embodiments, a vaccine or composition of the present invention can comprise any of the embodiments of WT1 peptides of the present invention and combinations thereof. Each possibility represents a separate embodiment of the present invention.

It is to be understood that any embodiments described herein, regarding peptides, vaccines and compositions of this invention can be employed in any of the methods of this invention. Each combination of peptide, vaccine, or composition with a method represents an embodiment thereof.

In another embodiment, the present invention provides a method of treating a subject with a WT1-expressing cancer, the method comprising administering to the subject a WT1 vaccine of the present invention, thereby treating a subject with a WT1-expressing cancer.

In another embodiment, the present invention provides a method of treating a subject with an MDS, the method comprising administering to the subject a WT1 vaccine of the present invention, thereby treating a subject with an MDS.

In another embodiment, the present invention provides a method of suppressing or halting the progression of a WT1-expressing cancer in a subject, the method comprising administering to the subject a WT1 vaccine of the present invention, thereby suppressing or halting the progression of a WT1-expressing cancer.

In another embodiment, the present invention provides a method of reducing the incidence of a WT1-expressing cancer in a subject, the method comprising administering to the subject a WT1 vaccine of the present invention, thereby reducing the incidence of a WT1-expressing cancer in a subject.

In another embodiment, the present invention provides a method of reducing the incidence of an AML in a subject, the method comprising administering to the subject a WT1 vaccine of the present invention, thereby reducing the incidence of an AML.

In another embodiment, the present invention provides a method of reducing the incidence of relapse of a WT1-expressing cancer in a subject, the method comprising administering to the subject a WT1 vaccine of the present invention, thereby reducing the incidence of relapse of a WT1-expressing cancer in a subject.

In another embodiment, the present invention provides a method of reducing the incidence of relapse of an AML in a subject, the method comprising administering to the subject a WT1 vaccine of the present invention, thereby reducing the incidence of relapse of an AML in a subject.

In another embodiment, the present invention provides a method of breaking a T cell tolerance of a subject to a WT1-expressing cancer, the method comprising administering to the subject a WT1 vaccine of the present invention, thereby breaking a T cell tolerance to a WT1-expressing cancer.

In another embodiment, the present invention provides a method of treating a subject having a WT1-expressing cancer, comprising (a) inducing in a donor formation and proliferation of human cytotoxic T lymphocytes (CTL) that recognize a malignant cell of the cancer by a method of the present invention; and (b) infusing the human CTL into the subject, thereby treating a subject having a cancer.

In another embodiment, the present invention provides a method of treating a subject having a WT 1-expressing cancer, comprising (a) inducing ex vivo formation and proliferation of human CTL that recognize a malignant cell of the cancer by a method of the present invention, wherein the human immune cells are obtained from a donor; and (b) infusing the human CTL into the subject, thereby treating a subject having a cancer.

Methods for ex vivo immunotherapy are well known in the art and are described, for example, in United States Patent Application Serial Numbers 2006/0057130, 2005/0221481, 2005/0214268, 2003/0175272, 2002/0127718, and U.S. Pat. No. 5,229,115, which are incorporated herein by reference. Additional methods are well known in the art and are described, for example, in Davis I D et al (Blood dendritic cells generated with Flt3 ligand and CD40 ligand prime CD8+ T cells efficiently in cancer patients. J Immunother. 2006 September-October; 29(5):499-511) and Mitchell M S et al (The cytotoxic T cell response to peptide analogs of the HLA-A*0201-restricted MUC1 signal sequence epitope, M1.2. Cancer Immunol Immunother. 2006 Jul. 28). Each method represents a separate embodiment of the present invention.

In another embodiment, the present invention provides a method of inducing the formation and proliferation of CTL specific for cells of a WT1-expressing cancer, the method comprising contacting a lymphocyte population with a vaccine of the present invention. In another embodiment, the vaccine is an APC associated with a peptide of the present invention. In another embodiment, the vaccine is an APC associated with a mixture of peptides of the present invention. Each possibility represents a separate embodiment of the present invention.

In another embodiment, this invention provides a method of generating a heteroclitic immune response in a subject, wherein the heteroclitic immune response is directed against a WT1-expressing cancer, the method comprising administering to the subject a vaccine of the present invention, thereby generating a heteroclitic immune response.

In another embodiment, the present invention provides a method of inducing an anti-mesothelioma immune response in a subject, the method comprising the step of contacting the subject with an immunogenic composition comprising (a) a WT1 protein; or (b) a fragment of a WT protein, thereby inducing an anti-mesothelioma immune response in a subject. In another embodiment, the mesothelioma is a malignant mesothelioma. Each possibility represents a separate embodiment of the present invention.

In another embodiment, the present invention provides a method of inducing an anti-mesothelioma immune response in a subject, the method comprising the step of contacting the subject with an immunogenic composition comprising a nucleotide molecule encoding (a) a WT1 protein; or (b) a fragment of a WT1 protein, thereby inducing an anti-mesothelioma immune response in a subject. In another embodiment, the mesothelioma is a malignant mesothelioma. Each possibility represents a separate embodiment of the present invention.

In another embodiment, the present invention provides a method of treating a subject with a mesothelioma, the method comprising the step of administering to the subject an immunogenic composition comprising (a) a WT1 protein; or (b) a fragment of a WT protein, thereby treating a subject with a mesothelioma. In another embodiment, the mesothelioma is a malignant mesothelioma. Each possibility represents a separate embodiment of the present invention.

In another embodiment, the present invention provides a method of treating a subject with a mesothelioma, the method comprising the step of administering to the subject an immunogenic composition comprising a nucleotide molecule encoding (a) a WT1 protein; or (b) a fragment of a WT1 protein, thereby treating a subject with a mesothelioma. In another embodiment, the mesothelioma is a malignant mesothelioma. Each possibility represents a separate embodiment of the present invention.

In another embodiment, the present invention provides a method of reducing an incidence of a mesothelioma, or its relapse, in a subject, the method comprising the step of administering to the subject an immunogenic composition comprising (a) a WT1 protein; or (b) a fragment of a WT protein, thereby reducing an incidence of a mesothelioma, or its relapse, in a subject. In another embodiment, the mesothelioma is a malignant mesothelioma. Each possibility represents a separate embodiment of the present invention.

In another embodiment, the present invention provides a method of reducing an incidence of a mesothelioma, or its relapse, in a subject, the method comprising the step of administering to the subject an immunogenic composition comprising a nucleotide molecule encoding (a) a WT1 protein; or (b) a fragment of a WT1 protein, thereby reducing an incidence of a mesothelioma, or its relapse, in a subject. In another embodiment, the mesothelioma is a malignant mesothelioma. Each possibility represents a separate embodiment of the present invention.

In another embodiment, a target cell of an immune response elicited by a method of the present invention presents the WT1 peptide of the present invention, or a corresponding WT1 fragment, on an HLA molecule. In another embodiment, the HLA molecule is an HLA class I molecule. In other embodiments, the HLA molecule is any HLA class I subtype or HLA class I molecule known in the art. In another embodiment, the immune response against the WT1 peptide or fragment is a heteroclitic immune response. Each possibility represents a separate embodiment of the present invention.

In another embodiment, the WT1-expressing cancer is an acute myelogenous leukemia (AML). In another embodiment, the WT1-expressing cancer is associated with a myelodysplastic syndrome (MDS). In another embodiment, the WT1-expressing cancer is an MDS. In another embodiment, the WT1-expressing cancer is a non-small cell lung cancer (NSCLC). In another embodiment, the WT1-expressing cancer is a Wilms' tumor. In another embodiment, the WT1-expressing cancer is a leukemia. In another embodiment, the WT1-expressing cancer is a hematological cancer. In another embodiment, the WT1-expressing cancer is a lymphoma. In another embodiment, the WT1-expressing cancer is a desmoplastic small round cell tumor. In another embodiment, the WT1-expressing cancer is a mesothelioma. In another embodiment, the WT1-expressing cancer is a malignant mesothelioma. In another embodiment, the WT1-expressing cancer is a gastric cancer. In another embodiment, the WT1-expressing cancer is a colon cancer. In another embodiment, the WT1-expressing cancer is a lung cancer. In another embodiment, the WT1-expressing cancer is a breast cancer. In another embodiment, the WT1-expressing cancer is a germ cell tumor. In another embodiment, the WT1-expressing cancer is an ovarian cancer. In another embodiment, the WT 1-expressing cancer is a uterine cancer. In another embodiment, the WT 1-expressing cancer is a thyroid cancer. In another embodiment, the WT1-expressing cancer is a hepatocellular carcinoma. In another embodiment, the WT1-expressing cancer is a thyroid cancer. In another embodiment, the WT1-expressing cancer is a liver cancer. In another embodiment, the WT1-expressing cancer is a renal cancer. In another embodiment, the WT1-expressing cancer is a Kaposi's sarcoma. In another embodiment, the WT1-expressing cancer is a sarcoma. In another embodiment, the WT1-expressing cancer is any other carcinoma or sarcoma.

In another embodiment, the WT1-expressing cancer is a solid tumor. In another embodiment, the solid tumor is associated with a WT1-expressing cancer. In another embodiment, the solid tumor is associated with a myelodysplastic syndrome (MDS). In another embodiment, the solid tumor is associated with a non-small cell lung cancer (NSCLC). In another embodiment, the solid tumor is associated with a lung cancer. In another embodiment, the solid tumor is associated with a breast cancer. In another embodiment, the solid tumor is associated with a colorectal cancer. In another embodiment, the solid tumor is associated with a prostate cancer. In another embodiment, the solid tumor is associated with an ovarian cancer. In another embodiment, the solid tumor is associated with a renal cancer. In another embodiment, the solid tumor is associated with a pancreatic cancer. In another embodiment, the solid tumor is associated with a brain cancer. In another embodiment, the solid tumor is associated with a gastrointestinal cancer. In another embodiment, the solid tumor is associated with a skin cancer. In another embodiment, the solid tumor is associated with a melanoma.

In another embodiment, a cancer or tumor treated by a method of the present invention is suspected to express WT1. In another embodiment, WT1 expression has not been verified by testing of the actual tumor sample. In another embodiment, the cancer or tumor is of a type known to express WT1 in many cases. In another embodiment, the type expresses WT1 in the majority of cases.

Each type of WT1-expressing cancer or tumor, and cancer or tumor suspected to express WT1, represents a separate embodiment of the present invention.

Any embodiments enumerated herein, regarding peptides, vaccines and compositions of this invention can be employed in any of the methods of this invention, and each represents an embodiment thereof.

In another embodiment, multiple peptides of this invention are used to stimulate an immune response in methods of the present invention.

The methods disclosed herein will be understood by those in the art to enable design of other WT1-derived peptides. The methods further enable design of peptides binding to other HLA molecules. The methods further enable design of vaccines combining WT1-derived peptides of the present invention. Each possibility represents a separate embodiment of the present invention.

In another embodiment, vaccines of the present invention have the advantage of activating or eliciting WT1-specific CD4<+> T cells containing a variety of different HLA class II alleles. In another embodiment, the vaccines have the advantage of activating or eliciting WT1-specific CD4<+> T cells in a substantial proportion of the population (e.g. in different embodiments, 50%, 55%, 60%, 65%, 70%, 75%, 80%. 85%, 90%, 95%, or greater than 95%). In another embodiment, the vaccines activate or elicit WT1-specific CD4<+> T cells in a substantial proportion of a particular population (e.g. American Caucasians). Each possibility represents a separate embodiment of the present invention.

In another embodiment, methods of the present invention provide for an improvement in an immune response that has already been mounted by a subject. In another embodiment, methods of the present invention comprise administering the peptide, composition, or vaccine 2 or more times. In another embodiment, the peptides are varied in their composition, concentration, or a combination thereof. In another embodiment, the peptides provide for the initiation of an immune response against an antigen of interest in a subject who has not yet initiated an immune response against the antigen. In another embodiment, the CTL that are induced proliferate in response to presentation of the peptide on the APC or cancer cell. In other embodiments, reference to modulation of the immune response involves, either or both the humoral and cell-mediated arms of the immune system, which is accompanied by the presence of Th2 and ThI T helper cells, respectively, or in another embodiment, each arm individually.

In other embodiments, the methods affecting the growth of a tumor result in (1) the direct inhibition of tumor cell division, or (2) immune cell mediated tumor cell lysis, or both, which leads to a suppression in the net expansion of tumor cells.

Inhibition of tumor growth by either of these two mechanisms can be readily determined by one of ordinary skill in the art based upon a number of well-known methods. In another embodiment, tumor inhibition is determined by measuring the actual tumor size over a period of time. In another embodiment, tumor inhibition can be determined by estimating the size of a tumor (over a period of time) utilizing methods well known to those of skill in the art. More specifically, a variety of radiologic imaging methods (e.g., single photon and positron emission computerized tomography; see generally, "Nuclear Medicine in Clinical Oncology," Winkler, C. (ed.) Springer-Verlag, New York, 1986), can be utilized to estimate tumor size. Such methods can also utilize a variety of imaging agents, including for example, conventional imaging agents (e.g., Gallium-67 citrate), as well as specialized reagents for metabolite imaging, receptor imaging, or immunologic imaging (e.g., radiolabeled monoclonal antibody specific tumor markers). In addition, non-radioactive methods such as ultrasound (see, "Ultrasonic Differential Diagnosis of Tumors", Kossoff and Fukuda, (eds.), Igaku-Shoin, New York, 1984), can also be utilized to estimate the size of a tumor.

In addition to the in vivo methods for determining tumor inhibition discussed above, a variety of in vitro methods can be utilized in order to predict in vivo tumor inhibition. Representative examples include lymphocyte mediated antitumor cytolytic activity determined for example, by a <51>Cr release assay (Examples), tumor dependent lymphocyte proliferation (Ioannides, et al., J. Immunol. 146(5): 1700-1707, 1991), in vitro generation of tumor specific antibodies (Herlyn, et al., J. Immunol. Meth. 73:157-167, 1984), cell (e.g., CTL, helper T-cell) or humoral (e.g., antibody) mediated inhibition of cell growth in vitro (Gazit, et al., Cancer Immunol Immunother 35:135-144, 1992), and, for any of these assays, determination of cell precursor frequency (Vose, Int. J. Cancer 30:135-142 (1982), and others.

In another embodiment, methods of suppressing tumor growth indicate a growth state that is curtailed compared to growth without contact with, or exposure to a peptide of this invention. Tumor cell growth can be assessed by any means known in the art, including, but not limited to, measuring tumor size, determining whether tumor cells are proliferating using a <3>H-thymidine incorporation assay, or counting tumor cells. "Suppressing" tumor cell growth refers, in other embodiments, to slowing, delaying, or stopping tumor growth, or to tumor shrinkage. Each possibility represents a separate embodiment of the present invention.

In another embodiment of methods and compositions of the present invention, WT1 expression is measured. In another embodiment, WT1 transcript expression is measured. In another embodiment, WT1 protein levels in the tumor are measured. Each possibility represents a separate embodiment of the present invention.

Methods of determining the presence and magnitude of an immune response are well known in the art. In another embodiment, lymphocyte proliferation assays, wherein T cell uptake of a radioactive substance, e.g. <3>H-thymidine is measured as a function of cell proliferation. In other embodiments, detection of T cell proliferation is accomplished by measuring increases in interleukin-2 (IL-2) production, Ca<2+> flux, or dye uptake, such as 3-(4,5-dimethylthiazol-2-yl)-2,5-diphenyl-tetrazolium. Each possibility represents a separate embodiment of the present invention.

In another embodiment, CTL stimulation is determined by means known to those skilled in the art, including, detection of cell proliferation, cytokine production and others. Analysis of the types and quantities of cytokines secreted by T cells upon contacting ligand-pulsed targets can be a measure of functional activity. Cytokines can be measured by ELISA or ELISPOT assays to determine the rate and total amount of cytokine production. (Fujihashi K. et al. (1993) J. Immunol. Meth. 160: 181; Tanguay S. and Killion J. J. (1994) Lymphokine Cytokine Res. 13:259).

In another embodiment, CTL activity is determined by <51>Cr-release lysis assay. Lysis of peptide-pulsed <51>Cr-labeled targets by antigen-specific T cells can be compared for target cells pulsed with control peptide. In another embodiment, T cells are stimulated with a peptide of this invention, and lysis of target cells expressing the native peptide in the context of MHC can be determined. The kinetics of lysis as well as overall target lysis at a fixed timepoint (e.g., 4 hours) are used, in another embodiment, to evaluate ligand performance. (Ware C. F. et al. (1983) J Immunol 131: 1312).

Methods of determining affinity of a peptide for an HLA molecule are well known in the art. In another embodiment, affinity is determined by TAP stabilization assays.

In another embodiment, affinity is determined by competition radioimmunoassay. In another embodiment, the following protocol is utilized: Target cells are washed two times in PBS with 1% bovine serum albumin (BSA; Fisher Chemicals, Fairlawn, NJ). Cells are resuspended at 10<7>/ml on ice, and the native cell surface bound peptides are stripped for 2 minutes at 0 [deg.] C using citrate-phosphate buffer in the presence of 3 mg/ml beta2 microglobulin. The pellet is resuspended at 5×10<6>cells/ml in PBS/1% BSA in the presence of 3 mg/ml beta2 microglobulin and 30 mg/ml deoxyribonuclease, and 200 ml aliquots are incubated in the presence or absence of HLA-specific peptides for 10 min at 20<0>C, then with <125>I-labeled peptide for 30 min at 20<0>C. Total bound <125>I is determined after two washes with PBS/2% BSA and one wash with PBS. Relative affinities are determined by comparison of escalating concentrations of the test peptide versus a known binding peptide.

In another embodiment, a specificity analysis of the binding of peptide to HLA on surface of live cells (e.g. SKLY-16 cells) is conducted to confirm that the binding is to the appropriate HLA molecule and to characterize its restriction. This includes, in another embodiment, competition with excess unlabeled peptides known to bind to the same or disparate HLA molecules and use of target cells which express the same or disparate HLA types. This assay is performed, in another embodiment, on live fresh or 0.25% paraformaldehyde-fixed human PBMC, leukemia cell lines and EBV-transformed T-cell lines of specific HLA types. The relative avidity of the peptides found to bind MHC molecules on the specific cells are assayed by competition assays as described above against <125>I-labeled peptides of known high affinity for the relevant HLA molecule, e.g., tyrosinase or HBV peptide sequence. [00165] In another embodiment, an HLA class II-binding peptide of methods and compositions of the present invention is longer than the minimum length for binding to an HLA class II molecule, which is, in another embodiment, about 12 AA. In another embodiment, increasing the length of the HLA class II-binding peptide enables binding to more than one HLA class II molecule. In another embodiment, increasing the length enables binding to an HLA class II molecule whose binding motif is not known. In another embodiment, increasing the length enables binding to an HLA class I molecule. In another embodiment, the binding motif of the HLA class I molecule is known. In another embodiment, the binding motif of the HLA class I molecule is not known. Each possibility represents a separate embodiment of the present invention.

In another embodiment, the peptides utilized in methods and compositions of the present invention comprise a non-classical amino acid such as: 1,2,3,4-tetrahydroisoquinoline-3-carboxylate (Kazmierski et al. (1991) J. Am Chem. Soc. 113:2275-2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby (1991) Tetrahedron Lett. 32(41): 5769-5772); 2-aminotetrahydronaphthalene-2-carboxylic acid (Landis (1989) Ph.D. Thesis, University of Arizona); hydroxy-1,2,3, 4-tetrahydroisoquinoline-3-carboxylate (Miyake et al. (1984) J. Takeda Res. Labs. 43:53-76) histidine isoquinoline carboxylic acid (Zechel et al. (1991) Int. J. Pep. Protein Res. 38(2):131-138); and HIC (histidine cyclic urea), (Dharanipragada et al. (1993) Int. J. Pep. Protein Res. 42(1):68-77) and ((1992) Acta. Crst., Crystal Struc. Comm 48(IV): 1239-124).

In another embodiment, a peptide of this invention comprises an AA analog or peptidomimetic, which, in other embodiments, induces or favors specific secondary structures. Such peptides comprise, in other embodiments, the following: LL-Acp (LL-3-amino-2-propenidone-6-carboxylic acid), a [beta]-turn inducing dipeptide analog (Kemp et al. (1985) J. Org. Chem. 50:5834-5838); [beta]-sheet inducing analogs (Kemp et al. (1988) Tetrahedron Lett. 29:5081-5082); [beta]-turn inducing analogs (Kemp et al. (1988) Tetrahedron Lett. 29:5057-5060); alpha-helix inducing analogs (Kemp et al. (1988) Tetrahedron Lett. 29:4935-4938); gamma-turn inducing analogs (Kemp et al. (1989) J. Org. Chem. 54:109:115); analogs provided by the following references: Nagai and Sato (1985) Tetrahedron Lett. 26:647-650; and DiMaio et al. (1989) J. Chem. Soc. Perkin Trans, p. 1687; a Gly-Ala turn analog (Kahn et al. (1989) Tetrahedron Lett. 30:2317); amide bond isostere (Jones et al. (1988) Tetrahedron Lett. 29(31):3853-3856); tretrazol (Zabrocki et al. (1988) J. Am. Chem. Soc. 110:5875-5880); DTC (Samanen et al. (1990) Int. J. Protein Pep. Res. 35:501:509); and analogs taught in Olson et al. (1990) J. Am. Chem. Sci. 112:323-333 and Garvey et al. (1990) J. Org. Chem. 55(3):936-940. Conformationally restricted mimetics of beta turns and beta bulges, and peptides containing them, are described in U.S. Pat. No. 5,440,013, issued Aug. 8, 1995 to Kahn.

In other embodiments, a peptide of this invention is conjugated to one of various other molecules, as described hereinbelow, which can be via covalent or non-covalent linkage (complexed), the nature of which varies, in another embodiment, depending on the particular purpose. In another embodiment, the peptide is covalently or non-covalently complexed to a macromolecular carrier, (e.g. an immunogenic carrier), including, but not limited to, natural and synthetic polymers, proteins, polysaccharides, polypeptides (amino acids), polyvinyl alcohol, polyvinyl pyrrolidone, and lipids. In another embodiment, a peptide of this invention is linked to a substrate. In another embodiment, the peptide is conjugated to a fatty acid, for introduction into a liposome (U.S. Pat. No. 5,837,249). In another embodiment, a peptide of the invention is complexed covalently or non-covalently with a solid support, a variety of which are known in the art. In another embodiment, linkage of the peptide to the carrier, substrate, fatty acid, or solid support serves to increase an elicited an immune response.

In other embodiments, the carrier is thyroglobulin, an albumin (e.g. human serum albumin), tetanus toxoid, polyamino acids such as poly (lysine: glutamic acid), an influenza protein, hepatitis B virus core protein, keyhole limpet hemocyanin, an albumin, or another carrier protein or carrier peptide; hepatitis B virus recombinant vaccine, or an APC. Each possibility represents a separate embodiment of the present invention.

In another embodiment, the term "amino acid" (AA) refers to a natural or, in another embodiment, an unnatural or synthetic AA, and can include, in other embodiments, glycine, D- or L optical isomers, AA analogs, peptidomimetics, or combinations thereof.

In another embodiment, the terms "cancer," "neoplasm," "neoplastic" or "tumor," are used interchangeably and refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. In another embodiment, a tumor is detectable on the basis of tumor mass; e.g., by such procedures as CAT scan, magnetic resonance imaging (MRI), X-ray, ultrasound or palpation, and in another embodiment, is identified by biochemical or immunologic findings, the latter which is used to identify cancerous cells, as well, in other embodiments.

Methods for synthesizing peptides are well known in the art. In another embodiment, the peptides of this invention are synthesized using an appropriate solid-state synthetic procedure (see for example, Steward and Young, Solid Phase Peptide Synthesis, Freemantle, San Francisco, Calif. (1968); Merrifield (1967) Recent Progress in Hormone Res 23: 451). The activity of these peptides is tested, in other embodiments, using assays as described herein.

In another embodiment, the peptides of this invention are purified by standard methods including chromatography (e.g., ion exchange, affinity, and sizing column chromatography), centrifugation, differential solubility, or by any other standard technique for protein purification. In another embodiment, immuno-affinity chromatography is used, whereby an epitope is isolated by binding it to an affinity column comprising antibodies that were raised against that peptide, or a related peptide of the invention, and were affixed to a stationary support.

In another embodiment, affinity tags such as hexa-His (Invitrogen), Maltose binding domain (New England Biolabs), influenza coat sequence (Kolodziej et al. (1991) Meth. Enzymol. 194:508-509), glutathione-S-transferase, or others, are attached to the peptides of this invention to allow easy purification by passage over an appropriate affinity column. Isolated peptides can also be physically characterized, in other embodiments, using such techniques as proteolysis, nuclear magnetic resonance, and x-ray crystallography.

In another embodiment, the peptides of this invention are produced by in vitro translation, through known techniques, as will be evident to one skilled in the art. In another embodiment, the peptides are differentially modified during or after translation, e.g., by phosphorylation, glycosylation, cross-linking, acylation, proteolytic cleavage, linkage to an antibody molecule, membrane molecule or other ligand, (Ferguson et al. (1988) Ann. Rev. Biochem. 57:285-320).

In another embodiment, the peptides of this invention further comprise a detectable label, which in another embodiment, is fluorescent, or in another embodiment, luminescent, or in another embodiment, radioactive, or in another embodiment, electron dense. In other embodiments, the detectable label comprises, for example, green fluorescent protein (GFP), DS-Red (red fluorescent protein), secreted alkaline phosphatase (SEAP), beta-galactosidase, luciferase, <32>P, <125>I, <3>H and <14>C, fluorescein and its derivatives, rhodamine and its derivatives, dansyl and umbelliferone, luciferin or any number of other such labels known to one skilled in the art. The particular label used will depend upon the type of immunoassay used.

In another embodiment, a peptide of this invention is linked to a substrate, which, in another embodiment, serves as a carrier. In another embodiment, linkage of the peptide to a substrate serves to increase an elicited an immune response.

In another embodiment, peptides of this invention are linked to other molecules, as described herein, using conventional cross-linking agents such as carbodiimides. Examples of carbodiimides are 1-cyclohexyl-3-(2-morpholinyl-(4-ethyl) carbodiimide (CMC), 1-ethyl-3-(3-dimethyaminopropyl) carbodiimide (EDC) and 1-ethyl-3-(4-azonia-44-dimethylpentyl) carbodiimide.

In other embodiments, the cross-linking agents comprise cyanogen bromide, glutaraldehyde and succinic anhydride. In general, any of a number of homo-bifunctional agents including a homo-bifunctional aldehyde, a homo-bifunctional epoxide, a homo-bifunctional imido-ester, a homo-bifunctional N-hydroxysuccinimide ester, a homo-bifunctional maleimide, a homo-bifunctional alkyl halide, a homo-bifunctional pyridyl disulfide, a homo-bifunctional aryl halide, a homo-bifunctional hydrazide, a homo-bifunctional diazonium derivative and a homo-bifunctional photoreactive compound can be used. Also envisioned, in other embodiments, are hetero-bifunctional compounds, for example, compounds having an amine-reactive and a sulfhydryl-reactive group, compounds with an amine-reactive and a photoreactive group and compounds with a carbonyl-reactive and a sulfhydryl-reactive group.

In other embodiments, the homo-bifunctional cross-linking agents include the bifunctional N-hydroxysuccinimide esters dithiobis(succinimidylpropionate), disuccinimidyl suberate, and disuccinimidyl tartarate; the bifunctional imido-esters dimethyl adipimidate, dimethyl pimelimidate, and dimethyl suberimidate; the bifunctional sulfhydryl-reactive crosslinkers 1,4-di-[3'-(2'-pyridyldithio)propionamido]butane, bismaleimidohexane, and bis-N-maleimido-1, 8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamido)ethyl] di sulfide; the bifunctional aldehydes formaldehyde, malondialdehyde, succinaldehyde, glutaraldehyde, and adipaldehyde; a bifunctional epoxide such as 1,4-butaneodiol diglycidyl ether; the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N1N'-ethylene-bis(iodoacetamide), N1N'-hexamethylene-bis(iodoacetamide), N1N'-undecamethylene-bis(iodoacetamide), as well as benzylhalides and halomustards, such as ala'-diiodo-p-xylene sulfonic acid and tri(2-chloroethyl)amine, respectively, In other embodiments, hetero-bifunctional cross-linking agents used to link the peptides to other molecules, as described herein, include, but are not limited to, SMCC (succinimidyl-4-(N-rnaleimidomethyl)cyclohexane-1-carboxylate), MB S (m-maleimidobenzoyl-N-hydroxysuccinimide ester), SIAB (N-succinimidyl(4-iodoacteyl)aminobenzoate), SMPB (succinimidyl-4-(p-maleimidophenyl) butyrate), GMBS (N-(.gamma.-maleimidobutyryloxy) succmimide ester), MPBH (4-(4-N-maleimidopohenyl) butyric acid hydrazide), M2C2H (4-(N-maleimidomethyl) cyclohexane-1-carboxyl-hydrazide), SMPT (succinimidyloxycarbonyl-a-methyl-a-(2-pyridyldithio)toluene), and SPDP (N-succinimidyl 3-(2-pyridyldithio)propionate).

In another embodiment, the peptides of the invention are formulated as non-covalent attachment of monomers through ionic, adsorptive, or biospecific interactions. Complexes of peptides with highly positively or negatively charged molecules can be accomplished, in another embodiment, through salt bridge formation under low ionic strength environments, such as in deionized water. Large complexes can be created, in another embodiment, using charged polymers such as poly-(L-glutamic acid) or poly-(L-lysine), which contain numerous negative and positive charges, respectively. In another embodiment, peptides are adsorbed to surfaces such as microparticle latex beads or to other hydrophobic polymers, forming non-covalently associated peptide-superantigen complexes effectively mimicking cross-linked or chemically polymerized protein, in other embodiments. In another embodiment, peptides are non-covalently linked through the use of biospecific interactions between other molecules. For instance, utilization of the strong affinity of biotin for proteins such as avidin or streptavidin or their derivatives could be used to form peptide complexes. The peptides, according to this aspect, and in another embodiment, can be modified to possess biotin groups using common biotinylation reagents such as the N-hydroxysuccinimidyl ester of D-biotin (NHS-biotin), which reacts with available amine groups.

In another embodiment, a peptide of the present invention is linked to a carrier. In another embodiment, the carrier is KLH. In other embodiments, the carrier is any other carrier known in the art, including, for example, thyroglobulin, albumins such as human serum albumin, tetanus toxoid, polyamino acids such as poly (lysine:glutamic acid), influenza, hepatitis B virus core protein, hepatitis B virus recombinant vaccine and the like. Each possibility represents a separate embodiment of the present invention.

In another embodiment, the peptides of this invention are conjugated to a lipid, such as P3 CSS. In another embodiment, the peptides of this invention are conjugated to a bead.

In another embodiment, the compositions of this invention further comprise immunomodulating compounds. In other embodiments, the immunomodulating compound is a cytokine, chemokine, or complement component that enhances expression of immune system accessory or adhesion molecules, their receptors, or combinations thereof. In some embodiments, the immunomodulating compound include interleukins, for example interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-Ia and MIP-Ib, complement components, or combinations thereof. In other embodiments, the immunomodulating compound stimulate expression, or enhanced expression of OX40, OX40L (gp34), lymphotactin, CD40, CD40L, B7.1, B7.2, TRAP, ICAM-1, 2 or 3, cytokine receptors, or combination thereof.

In another embodiment, the immunomodulatory compound induces or enhances expression of co-stimulatory molecules that participate in the immune response, which include, in some embodiments, CD40 or its ligand, CD28, CTLA-4 or a B7 molecule. In another embodiment, the immunomodulatory compound induces or enhances expression of a heat stable antigen (HSA) (Liu Y. et al. (1992) J. Exp. Med. 175:437-445), chondroitin sulfate-modified MHC invariant chain (Ii-CS) (Naujokas M. F. et al (1993) Cell 74:257-268), or an intracellular adhesion molecule 1 (ICAM-I) (Van R. H. (1992) Cell 71: 1065-1068), which assists, in another embodiment, co-stimulation by interacting with their cognate ligands on the T cells.

In another embodiment, the composition comprises a solvent, including water, dispersion media, cell culture media, isotonic agents and the like. In another embodiment, the solvent is an aqueous isotonic buffered solution with a pH of around 7.0. In another embodiment, the composition comprises a diluent such as water, phosphate buffered saline, or saline. In another embodiment, the composition comprises a solvent, which is non-aqueous, such as propyl ethylene glycol, polyethylene glycol and vegetable oils.

In another embodiment, the composition is formulated for administration by any of the many techniques known to those of skill in the art. For example, this invention provides for administration of the pharmaceutical composition parenterally, intravenously, subcutaneously, intradermally, intramucosally, topically, orally, or by inhalation.

In another embodiment, the vaccine comprising a peptide of this invention further comprises a cell population, which, in another embodiment, comprises lymphocytes, monocytes, macrophages, dendritic cells, endothelial cells, stem cells or combinations thereof, which, in another embodiment are autologous, syngeneic or allogeneic, with respect to each other. In another embodiment, the cell population comprises a peptide of the present invention. In another embodiment, the cell population takes up the peptide. Each possibility represents a separate embodiment of the present invention.

In another embodiment, the cell populations of this invention are obtained from in vivo sources, such as, for example, peripheral blood, leukopheresis blood product, apheresis blood product, peripheral lymph nodes, gut associated lymphoid tissue, spleen, thymus, cord blood, mesenteric lymph nodes, liver, sites of immunologic lesions, e.g. synovial fluid, pancreas, cerebrospinal fluid, tumor samples, granulomatous tissue, or any other source where such cells can be obtained. In another embodiment, the cell populations are obtained from human sources, which are, in other embodiments, from human fetal, neonatal, child, or adult sources. In another embodiment, the cell populations of this invention are obtained from animal sources, such as, for example, porcine or simian, or any other animal of interest. In another embodiment, the cell populations of this invention are obtained from subjects that are normal, or in another embodiment, diseased, or in another embodiment, susceptible to a disease of interest.

In another embodiment, the cell populations of this invention are separated via affinity-based separation methods. Techniques for affinity separation include, in other embodiments, magnetic separation, using antibody-coated magnetic beads, affinity chromatography, cytotoxic agents joined to a monoclonal antibody or use in conjunction with a monoclonal antibody, for example, complement and cytotoxins, and “panning” with an antibody attached to a solid matrix, such as a plate, or any other convenient technique. In other embodiment, separation techniques include the use of fluorescence activated cell sorters, which can have varying degrees of sophistication, such as multiple color channels, low angle and obtuse light scattering detecting channels, impedance channels, etc. In other embodiments, any technique that enables separation of the cell populations of this invention can be employed, and is to be considered as part of this invention.

In another embodiment, the dendritic cells are from the diverse population of morphologically similar cell types found in a variety of lymphoid and non-lymphoid tissues, qualified as such (Steinman (1991) Ann. Rev. Immunol. 9:271-296). In another embodiment, the dendritic cells used in this invention are isolated from bone marrow, or in another embodiment, derived from bone marrow progenitor cells, or, in another embodiment, from isolated from/derived from peripheral blood, or in another embodiment, derived from, or are a cell line.

In another embodiment, the cell populations described herein are isolated from the white blood cell fraction of a mammal, such as a murine, simian or a human (See, e.g., WO 96/23060). The white blood cell fraction can be, in another embodiment, isolated from the peripheral blood of the mammal.

Methods of isolating dendritic cells are well known in the art. In another embodiment, the DC are isolated via a method which includes the following steps: (a) providing a white blood cell fraction obtained from a mammalian source by methods known in the art such as leukophoresis; (b) separating the white blood cell fraction of step (a) into four or more subfractions by countercurrent centrifugal elutriation; (c) stimulating conversion of monocytes in one or more fractions from step (b) to dendritic cells by contacting the cells with calcium ionophore, GM-CSF and IL-13 or GM-CSF and IL-4, (d) identifying the dendritic cell-enriched fraction from step (c); and (e) collecting the enriched fraction of step (d), preferably at about 4[deg.] C.

In another embodiment, the dendritic cell-enriched fraction is identified by fluorescence-activated cell sorting, which identifies at least one of the following markers: HLA-DR, HLA-DQ, or B7.2, and the simultaneous absence of the following markers: CD3, CD14, CD16, 56, 57, and CD 19, 20.

In another embodiment, the cell population comprises lymphocytes, which are, in another embodiment, T cells, or in another embodiment, B cells. The T cells are, in other embodiments, characterized as NK cells, helper T cells, cytotoxic T lymphocytes (CTL), TBLs, naive T cells, or combinations thereof. It is to be understood that T cells which are primary, or cell lines, clones, etc. are to be considered as part of this invention. In another embodiment, the T cells are CTL, or CTL lines, CTL clones, or CTLs isolated from tumor, inflammatory, or other infiltrates.

In another embodiment, hematopoietic stem or early progenitor cells comprise the cell populations used in this invention. In another embodiment, such populations are isolated or derived, by leukaphoresis. In another embodiment, the leukapheresis follows cytokine administration, from bone marrow, peripheral blood (PB) or neonatal umbilical cord blood. In another embodiment, the stem or progenitor cells are characterized by their surface expression of the surface antigen marker known as CD34<+>, and exclusion of expression of the surface lineage antigen markers, Lin−.

In another embodiment, the subject is administered a peptide, composition or vaccine of this invention, in conjunction with bone marrow cells. In another embodiment, the administration together with bone marrow cells embodiment follows previous irradiation of the subject, as part of the course of therapy, in order to suppress, inhibit or treat cancer in the subject.

In another embodiment, the phrase "contacting a cell" or "contacting a population" refers to a method of exposure, which can be, in other embodiments, direct or indirect. In another embodiment, such contact comprises direct injection of the cell through any means well known in the art, such as microinjection. It is also envisaged, in another embodiment, that supply to the cell is indirect, such as via provision in a culture medium that surrounds the cell, or administration to a subject, via any route well known in the art, and as described herein.

In another embodiment, CTL generation of methods of the present invention is accomplished in vivo, and is effected by introducing into a subject an antigen presenting cell contacted in vitro with a peptide of this invention (See for example Paglia et al. (1996) J. Exp. Med. 183:317-322).

In another embodiment, the peptides of methods and compositions of the present invention are delivered to APC. In another embodiment, the peptide-pulsed APC are administered to a subject to elicit and immune response or treat or inhibit growth or recurrence of a tumor. Each possibility represents a separate embodiment of the present invention.

In another embodiment, the peptides are delivered to APC in the form of cDNA encoding the peptides. In another embodiment, the term "antigen-presenting cells" (APC) refers to dendritic cells (DC), monocytes/macrophages, B lymphocytes or other cell type(s) expressing the necessary MHC/co-stimulatory molecules, which effectively allow for T cell recognition of the presented peptide. In another embodiment, the APC is a cancer cell. Each possibility represents a separate embodiment of the present invention.

In another embodiment, the CTL are contacted with 2 or more APC populations. In another embodiment, the 2 or more APC populations present different peptides. Each possibility represents a separate embodiment of the present invention.

In another embodiment, techniques that lead to the expression of antigen in the cytosol of APC (e.g. DC) are used to deliver the peptides to the APC. Methods for expressing antigens on APC are well known in the art. In another embodiment, the techniques include (1) the introduction into the APC of naked DNA encoding a peptide of this invention, (2) infection of APC with recombinant vectors expressing a peptide of this invention, and (3) introduction of a peptide of this invention into the cytosol of an APC using liposomes. (See Boczkowski D. et al. (1996) J. Exp. Med. 184:465-472; Rouse et al. (1994) J. Virol. 68:5685-5689; and Nair et al. (1992) J. Exp. Med. 175:609-612).

In another embodiment, foster APC such as those derived from the human cell line 174xCEM.T2, referred to as T2, which contains a mutation in its antigen processing pathway that restricts the association of endogenous peptides with cell surface MHC class I molecules (Zweerink et al. (1993) J. Immunol. 150:1763-1771), are used, as exemplified herein.

In another embodiment, as described herein, the subject is exposed to a peptide, or a composition/cell population comprising a peptide of this invention, which differs from the native protein expressed, wherein subsequently a host immune cross-reactive with the native protein/antigen develops.

In another embodiment, the subject, as referred to in any of the methods or embodiments of this invention is a human. In other embodiments, the subject is a mammal, which can be a mouse, rat, rabbit, hamster, guinea pig, horse, cow, sheep, goat, pig, cat, dog, monkey, or ape. Each possibility represents a separate embodiment of the present invention.

In another embodiment, peptides, vaccines, and compositions of this invention stimulate an immune response that results in tumor cell lysis.

In another embodiment, any of the methods described herein is used to elicit CTL, which are elicited in vitro. In another embodiment, the CTL are elicited ex-vivo. In another embodiment, the CTL are elicited in vitro. The resulting CTL, are, in another embodiment, administered to the subject, thereby treating the condition associated with the peptide, an expression product comprising the peptide, or a homologue thereof. Each possibility represents a separate embodiment of the present invention.

In another embodiment, the method entails introduction of the genetic sequence that encodes the peptides of this invention using, e.g., one or more nucleic acid delivery techniques. Nucleic acids of the invention include, in another embodiment, DNA, RNA and mixtures of DNA and RNA, alone or in conjunction with non-nucleic acid components. In another embodiment, the method comprises administering to the subject a vector comprising a nucleotide sequence, which encodes a peptide of the present invention (Tindle, R. W. et al. Virology (1994) 200:54). In another embodiment, the method comprises administering to the subject naked DNA which encodes a peptide, or in another embodiment, two or more peptides of this invention (Nabel, et al. PNAS-USA (1990) 90: 11307). In another embodiment, multi-epitope, analogue-based cancer vaccines are utilized (Fikes et al, Design of multi-epitope, analogue-based cancer vaccines. Expert Opin Biol Ther. 2003 September; 3(6):985-93). Each possibility represents a separate embodiment of the present invention.

Nucleic acids can be administered to a subject via any means as is known in the art, including parenteral or intravenous administration, or in another embodiment, by means of a gene gun. In another embodiment, the nucleic acids are administered in a composition, which correspond, in other embodiments, to any embodiment listed herein.

Vectors for use according to methods of this invention can comprise any vector that facilitates or allows for the expression of a peptide of this invention. Vectors comprises, in some embodiments, attenuated viruses, such as vaccinia or fowlpox, such as described in, e.g., U.S. Pat. No. 4,722,848, incorporated herein by reference. In another embodiment, the vector is BCG (Bacille Calmette Guerin), such as described in Stover et al. (Nature 351:456-460 (1991)). A wide variety of other vectors useful for therapeutic administration or immunization of the peptides of the invention, e.g., *Salmonella typhi* vectors and the like, will be apparent to those skilled in the art from the description herein.

In another embodiment, the vector further encodes for an immunomodulatory compound, as described herein. In another embodiment, the subject is administered an additional vector encoding same, concurrent, prior to or following administration of the vector encoding a peptide of this invention to the subject.

In another embodiment, the peptides, compositions and vaccines of this invention are administered to a subject, or utilized in the methods of this invention, in combination with other anticancer compounds and chemotherapeutics, including monoclonal antibodies directed against alternate cancer antigens, or, in another embodiment, epitopes that consist of an AA sequence which corresponds to, or in part to, that from which the peptides of this invention are derived.

Various embodiments of dosage ranges are contemplated by this invention. [mu] refers to micro; [mu]g referring to microgram or micrograms. In another embodiment, the dosage is 20 [mu]g per peptide per day. In another embodiment, the dosage is 10 [mu]g/peptide/day. In another embodiment, the dosage is 30 [mu]g/peptide/day. In another embodiment, the dosage is 40 [mu]g/peptide/day. In another embodiment, the dosage is 60 [mu]g/peptide/day. In another embodiment, the dosage is 80 [mu]g/peptide/day. In another embodiment, the dosage is 100 [mu]g/peptide/day. In another embodiment, the dosage is 150 [mu]g/peptide/day. In another embodiment, the dosage is 200 [mu]g/peptide/day. In another embodiment, the dosage is 300 [mu]g/peptide/day. In another embodiment, the dosage is 400 [mu]g/peptide/day. In another embodiment, the dosage is 600 [mu]g/peptide/day. In another embodiment, the dosage is 800 [mu]g/peptide/day. In another embodiment, the dosage is 1000 [mu]g/peptide/day. In another embodiment, the dosage is 1500 [mu]g/peptide/day. In another embodiment, the dosage is 2000 [mu]g/peptide/day.

In another embodiment, the dosage is 10 [mu]g/peptide/dose. In another embodiment, the dosage is 30 [mu]g/peptide/dose. In another embodiment, the dosage is 40 [mu]g/peptide/dose. In another embodiment, the dosage is 60 [mu]g/peptide/dose. In another embodiment, the dosage is 80 [mu]g/peptide/dose. In another embodiment, the dosage is 100 [mu]g/peptide/dose. In another embodiment, the dosage is 150 [mu]g/peptide/dose. In another embodiment, the dosage is 200 [mu]g/peptide/dose. In another embodiment, the dosage is 300 [mu]g/peptide/dose. In another embodiment, the dosage is 400 [mu]g/peptide/dose. In another embodiment, the dosage is 600 [mu]g/peptide/dose. In another embodiment, the dosage is 800 [mu]g/peptide/dose. In another embodiment, the dosage is 1000 [mu]g/peptide/dose. In another embodiment, the dosage is 1500 [mu]g/peptide/dose. In another embodiment, the dosage is 2000 [mu]g/peptide/dose.

In another embodiment, the dosage is 10-20 [mu]g/peptide/dose. In another embodiment, the dosage is 20-30 [mu]g/peptide/dose. In another embodiment, the dosage is 20-40 [mu]g/peptide/dose. In another embodiment, the dosage is 30-60 [mu]g/peptide/dose. In another embodiment, the dosage is 40-80 [mu]g/peptide/dose. In another embodiment, the dosage is 50-100 [mu]g/peptide/dose. In another embodiment, the dosage is 50-150 [mu]g/peptide/dose. In another embodiment, the dosage is 100-200 [mu]g/peptide/dose. In another embodiment, the dosage is 200-300 [mu]g/peptide/dose. In another embodiment, the dosage is 300-400 [mu]g/peptide/dose. In another embodiment, the dosage is 400-600 [mu]g/peptide/dose. In another embodiment, the dosage is 500-800 [mu]g/peptide/dose. In another embodiment, the dosage is 800-1000 [mu]g/peptide/dose. In another embodiment, the dosage is 1000-1500 [mu]g/peptide/dose. In another embodiment, the dosage is 1500-2000 [mu]g/peptide/dose.

In another embodiment, the total amount of peptide per dose or per day is one of the above amounts. In another embodiment, the total peptide dose per dose is one of the above amounts.

Each of the above doses represents a separate embodiment of the present invention.

Various embodiments of dosage ranges are contemplated by this invention. In another embodiment, the dosage is 20 mg per peptide per day. In another embodiment, the dosage is 10 mg/peptide/day. In another embodiment, the dosage is 30 mg/peptide/day. In another embodiment, the dosage is 40 mg/peptide/day. In another embodiment, the dosage is 60 mg/peptide/day. In another embodiment, the dosage is 80 mg/peptide/day. In another embodiment, the dosage is 100 mg/peptide/day. In another embodiment, the dosage is 150 mg/peptide/day. In another embodiment, the dosage is 200 mg/peptide/day. In another embodiment, the dosage is 300 mg/peptide/day. In another embodiment, the dosage is 400 mg/peptide/day. In another embodiment, the dosage is 600 mg/peptide/day. In another embodiment, the dosage is 800 mg/peptide/day. In another embodiment, the dosage is 1000 mg/peptide/day.

In another embodiment, the dosage is 10 mg/peptide/dose. In another embodiment, the dosage is 30 mg/peptide/dose. In another embodiment, the dosage is 40 mg/peptide/dose. In another embodiment, the dosage is 60 mg/peptide/dose. In another embodiment, the dosage is 80 mg/peptide/dose. In another embodiment, the dosage is 100 mg/peptide/dose. In another embodiment, the dosage is 150 mg/peptide/dose. In another embodiment, the dosage is 200 mg/peptide/dose. In another embodiment, the dosage is 300 mg/peptide/dose. In another embodiment, the dosage is 400 mg/peptide/dose. In another embodiment, the dosage is 600 mg/peptide/dose. In another embodiment, the dosage is 800 mg/peptide/dose. In another embodiment, the dosage is 1000 mg/peptide/dose.

In another embodiment, the dosage is 10-20 mg/peptide/dose. In another embodiment, the dosage is 20-30 mg/peptide/dose. In another embodiment, the dosage is 20-40 mg/peptide/dose. In another embodiment, the dosage is 30-60 mg/peptide/dose. In another embodiment, the dosage is 40-80 mg/peptide/dose. In another embodiment, the dosage is 50-100 mg/peptide/dose. In another embodiment, the dosage is 50-150 mg/peptide/dose. In another embodiment, the dosage is 100-200 mg/peptide/dose. In another embodiment, the dosage is 200-300 mg/peptide/dose. In another embodiment, the dosage is 300-400 mg/peptide/dose. In another embodiment, the dosage is 400-600 mg/peptide/dose. In another embodiment, the dosage is 500-800 mg/peptide/dose. In another embodiment, the dosage is 800-1000 mg/peptide/dose.

In another embodiment, the total amount of peptide per dose or per day is one of the above amounts. In another embodiment, the total peptide dose per dose is one of the above amounts.

Each of the above doses represents a separate embodiment of the present invention.

In another embodiment, the present invention provides a kit comprising a peptide, composition or vaccine of the present invention. In another embodiment, the kit further comprises a label or packaging insert. In another embodiment, the kit is used for detecting a WT1-specific CD4 response through the use of a delayed-type hypersensitivity test. In another embodiment, the kit is used for any other method enumerated herein. In another embodiment, the kit is used for any other method known in the art. Each possibility represents a separate embodiment of the present invention.

Example 1. Materials and Methods

Peptide Design.

Using three computer-based predictive algorisms BIMAS (http://www-bimas.cit.nih.gov/cgi-bin/molbio/ken_parker-_comboform), SYFPEITHI (http://www.syfpeithi.de/) and RANKPEP (http://bio.dfci.harvard.edu/Tools/rankpep.html), epitopes were selected for both CD8 and CD4 T cells by starting with the native WT1 protein sequences that are capable of inducing immune response in normal donors. Heteroclitic peptides were designed by altering a single amino acid in the anchor residues of the native peptides for class I, which resulted in a higher predicted binding than its native sequences. The class II peptides were designed by adding flanking residues to the class I peptides, in order to simultaneously stimulate both CD4 and CD8 T cells. While many sequences can be predicted by the algorithms, these models do not predict binding to MHC when tested on live cells in 30% of cases (Gomez-Nunez et al. Leuk Res. 2006; 30(10): 1293-8), therefore in vitro testing is necessary. In addition, even if binding is demonstrated, a cytotoxic T cell response may not occur, requiring additional in vitro study.

Peptide Synthesis.

All peptides were purchased and synthesized by Genemed Synthesis, Inc. (San Antonio, TX). Peptides were sterile with purity of 70% to 90%. The peptides were dissolved in DMSO and diluted in saline at 5 mg/mL and stored at −80° C. Control peptides used are: for HLA-DR.B1: JAK-2-derived DR.B1-binding peptide JAK2-DR (GVCVCGDENILVQEF; SEQ ID NO:59) or BCR.ABL-derived peptide (IVHSATGFKQSSKALQRPVASDFEP; SEQ ID NO:60); for HLA-A0201: ewing sarcoma-derived peptide EW (QLQNPSYDK; SEQ ID NO:61) and for HLA-A2402: prostate-specific membrane antigen (PMSA)-derived peptide 624-632 (TYSVSFDSL; SEQ ID NO:62).

Cells Lines, Cytokines and Antibodies.

Human leukemia cell lines BA25 and HL-60 were used as a targets for measuring cytotoxicity of T cells. Human granulocyte-macrophage colony-stimulating factor (GM-CSF), interleukin (IL)-1beta, IL-4, IL-6, IL-15, tumor necrosis factor (TNF)-alpha and prostaglandin E2 (PGE2) were purchased from R&D Systems (Minneapolis, MN). Beta 2-microglobulin (b2-m) was purchased from Sigma (St. Louis, MO). The antibodies used for immunofluorescence assays including mAbs to human CD3, CD4, CD8, HLA-A2 (clone BB7.2) and isotype controls were obtained from BD Biosciences (San Diego, CA). Cell isolation kits for CD14 and CD3 were purchased from Miltenyi Biotec. (Bergisch Gladbach, Germany).

T2 Assay for Peptide Binding.

T2 cells (TAP-, HLA-A0201+) were incubated overnight at 37° C. at $1\times10^6$ cells/ml in FCS-free RPMI medium supplemented with 10 ug/ml human beta-2m (Sigma, St Louis, MO, USA) in the absence (negative control) or presence peptides at various final concentrations (50, 10 and 2 ug/ml). Brefeldin A (Sigma) at 5 ug/ml was added to the cultures for the final two hrs of incubation. Then T2 cells were washed and stained with anti-HLA-A2.1 (BB7.2) mAb conjugated to FITC for 30 min at 4° C. and followed by washing with staining buffer (PBS plus 1% FBS and 0.02% azide). The expression of the HLA-A2 on the cell surface was measured by flow cytometry on a FACScalibur (Becton Dickinson) and analyzed with FlowJo 9.6.3 software.

In Vitro Stimulation and Human T-Cell Cultures.

Peripheral blood mononuclear cells (PBMCs) from HLA-typed healthy donors were obtained by Ficoll density centrifugation. CD14+ monocytes were isolated by positive selection using mAb to human CD14 coupled with magnetic beads (Miltenyi Biotec) and were used for the first stimulation of T cells. The CD14− fraction of PBMC were used for isolation of CD3, by negative immunomagnetic cell separation using a pan T cell isolation kit (Miltenyi Biotec). The purity of the cells was always more than 98%. T cells were stimulated for 7 days in the presence of RPMI 1640 supplemented with 5% autologous plasma (AP), 20 ug/mL synthetic peptides, 1 ug/mL B2-m, and 10 ng/mL IL-15. Monocyte-derived dendritic cells (DCs) were generated from CD14+ cells, by culturing the cells in RPMI 1640 medium supplemented with 1% AP, 500 units/mL recombinant IL-4, and 1,000 units/mL GM-CSF. On days 2 and 4 of incubation, fresh medium with IL-4 and GM-CSF was either added or replaced half of the culture medium. On day 5, 20 ug/mL class II peptide was added to the immature DCs, for the processing. On day 6, maturation cytokine cocktail was added (Dao et al. Plos One 2009; 4(8):e6730). On day 7 or 8, T cells were re-stimulated with mature DCs, with IL-15. In most cases, T cells were stimulated 3 times in the same manner, using either DCs or CD14+ cells as antigen-presenting cells (APCs). A week after final stimulation, the peptide-specific T cell response was examined by IFN-g enzyme-linked immunospot (ELISPOT) assay and the cytotoxicity was tested, by $^{51}$ chromium (Cr)-release assay.

IFN-g ELISPOT.

HA-Multiscreen plates (Millipore) were coated with 100 uL of mouse anti-human IFN-g antibody (10 Ag/mL; clone 1-D1K; Mabtech) in PBS, incubated overnight at 4 C, washed with PBS to remove unbound antibody, and blocked with RPMI 1640/10% autologous plasma (AP) for 2 h at 37° C. Purified CD3+ T cells (>98% pure) were plated with either autologous CD14+ (10:1 E:APC ratio) or autologous DCs (30:1 E:APC ratio). Various test peptides were added to the wells at 20 ug/mL. Negative control wells contained APCs and T cells without peptides or with irrelevant peptides. Positive control wells contained T cells plus APCs plus 20 ug/mL phytohemagglutinin (PHA, Sigma). All conditions were done in triplicates. Microtiter plates were incubated for 20 h at 37° C. and then extensively washed with PBS/0.05% Tween and 100 ul/well biotinylated detection antibody against human IFN-g (2 ug/mL; clone 7-B6-1; Mabtech) was added. Plates were incubated for an additional 2 h at 37° C. and spot development was done as described (Dao et al., op. cit.). Spot numbers were automatically determined with the use of a computer-assisted video image analyzer with KS ELISPOT 4.0 software (Carl Zeiss Vision).

$^{51}$Chromium Release Assay.

The presence of specific CTLs was measured in a standard chromium release assay as described (Dao et al., op. cit.). Briefly, target cells alone, or pulsed with 50 ug/mL of synthetic peptides for 2 hours (in some cases for over night) at 37° C., are labeled with 50 uCi/million cells of $Na_2{}^{51}CrO_4$ (NEN Life Science Products, Inc.). After extensive washing, target cells are incubated with T cells at E:T ratios ranging from 100:1 to 10:1. All conditions were done in triplicate. Plates were incubated for 4-5 hrs at 37° C. in 5% CO2. Supernatant fluids were harvested and radioactivity was measured in a gamma counter. Percentage specific lysis was determined from the following formula: [(experimental release−spontaneous release)/(maximum release−spontaneous release)]×100%. Maximum release was determined by lysis of radiolabeled targets in 1% SDS.

Example 2. Binding of the Native and its Analogue Peptides to HLA-A0201 and HLA-A2402

Using a pool of 15 mer overlapping peptides spanning human WT1 protein to sensitize human T cells in vitro, the sequence 239-248 (NQMNLGATL; SEQ ID NO:5; herein abbreviated NQM or) has recently been identified as an immunogenic CD8 T cell epitope in the context of HLA-A2402 (Doubrovina et al., Blood 2012; 123(8):1633-46). In order to generate analog peptides with stronger immunogenicity, the prediction scores of the native peptide and possible analogs with various amino acid substitutions in the position 2 and 9 (class I anchor residues) was screened, using three online available databases (BIMAS, RANKPEP and SYFPEITHI). The predicted binding scores from all three databases showed better binding of the native NQMNLGATL (SEQ ID NO:5) peptide to HLA-A0201 than HLA-A2402 molecule (Table I). When the glutamine at the position 2 was substituted by leucine, the binding score to HLA-A2402 remained at the similar level by all 3 prediction programs. However, a significantly stronger binding score was predicted for HLA-A0201. On the other hand, when the glutamine at the position 2 was substituted by tyrosine, binding score to HLA-A2402 was dramatically improved, showing about 90-fold increased binding by BIMAS prediction. All three peptides were predicted to be cleaved at c-terminal by RANKPEP algorithm, suggesting the processing of the peptide fragment. The binding score was checked by substitution with various amino acids at position 9 but none of them showed a significant improved binding compared to the substitution at the position 2. Therefore, the two analogue peptides NLMNLGATL (SEQ ID NO:6; herein abbreviated NLM or A24-het-1) and NYMNLGATL (SEQ ID NO:7; herein abbreviated NYM or A24-het-2) were selected for further studies.

an increase in the level of surface HLA-A0201 recognizable by specific anti-HLA-A0201 mAb such as BB7.2.

The T2 binding assay showed that native NQMNLGATL (SEQ ID NO:5) peptide did not increase the HLA-A2 expression on T2 cells (FIG. 1, upper panel). However, the NLMNLGATL (SEQ ID NO:6) analogue peptide stabilized the HLA-A2 molecule by showing a dose-dependent increase in HLA-A2 expression, compared to the T2 cells without peptide pulsing (FIG. 1 middle panel). Similar to the native peptide NQMNLGATL, NYMNLGATL (SEQ ID NO:7) peptide did not increase the HLA-A2 expression (FIG. 1 lower panel). These data confirmed the HLA-A2 biding scores, predicted by the computer-based algorithm.

Example 4. Induction of a Peptide-Specific of CD8 T Cell Response the Context of HLA-A0201 and A2402 Molecules Although affinity for MHC molecules is necessary for the peptide presentation, T cell recognition of the peptide presented by HLA molecules is another important requirement for eliciting the peptide-specific response. Therefore, using an in vitro stimulation protocol, the new synthetic WT1 peptide analogs were evaluated for their ability to stimulate peptide-specific T cell response in both HLA-A0201 and A2402 donors.

To expand the peptide-specific T cell precursors, three to five in vitro stimulation were performed and the specific T cell response was measured by IFN-g production, when challenged with individual peptide. NLMNLGATL peptide

TABLE 1

Predictive binding scores of the peptides to HLA-A0201 and A2402

| Sequences (p 239-247) | BIMAS HLA-A0201 | BIMAS HLA-A2402 | SYFPETHI HLA-A0201 | SYFPETHI HLA-A24 | RANKPEP (score; % opt) HLA-A0201 | RANKPEP (score; % opt) HLA-A2402 |
|---|---|---|---|---|---|---|
| NQMNLGATL (SEQ ID NO: 5) | 8.014 | 7.200 | 17 | 10 | 34; 26.56% Cleaved | 10.482; 27.23%, Cleaved |
| NLMNLGATL (SEQ ID NO: 6) | 79.041 | 7.2 | 26 | 10 | 78; 60.94% Cleaved | 8.948; 23.24%, Cleaved |
| NYMNLGATL (SEQ ID NO: 7) | 0.011 | 360.000 | 9 | 20 | 41; 32.03% Cleaved | 23.573; 61.22%, Cleaved |

Example 3. Binding of the Peptides to HLA-A0201 and HLA-A2402 Molecules

Figure 2A:
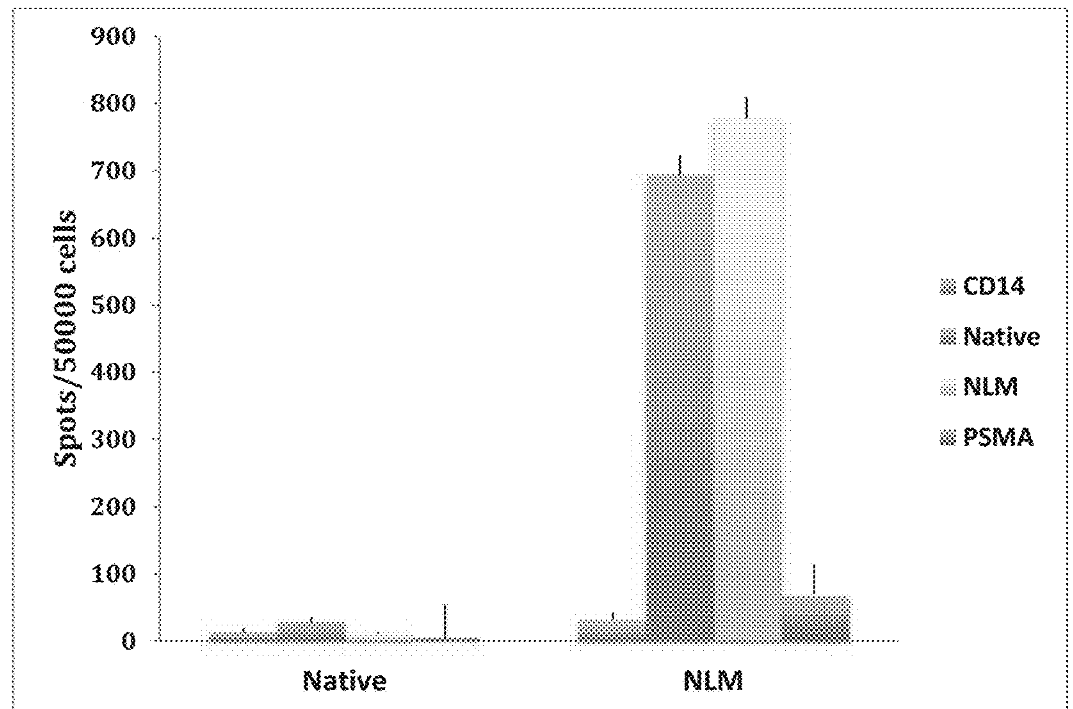
FIG. 2 A-B show that NLMNLGATL peptide induces strong peptide-specific T cell response which cross-reacts to its native sequence NQMNLGATL. For each peptide, the bars represent, from left to right, CD14, Native peptide, NLMNLGATL and PSMA, respectively. CD3 T cells from a healthy HLA-A0201 homozygous donor was stimulated with either NQM or NLMNLGATL peptide for 3 (A) or 5 (B) rounds. The peptide-specific response was measured by the IFN-g secretion upon challenged with individual peptide. Each data point represents average+/−SD from triplicate cultures.
Figure 2B:
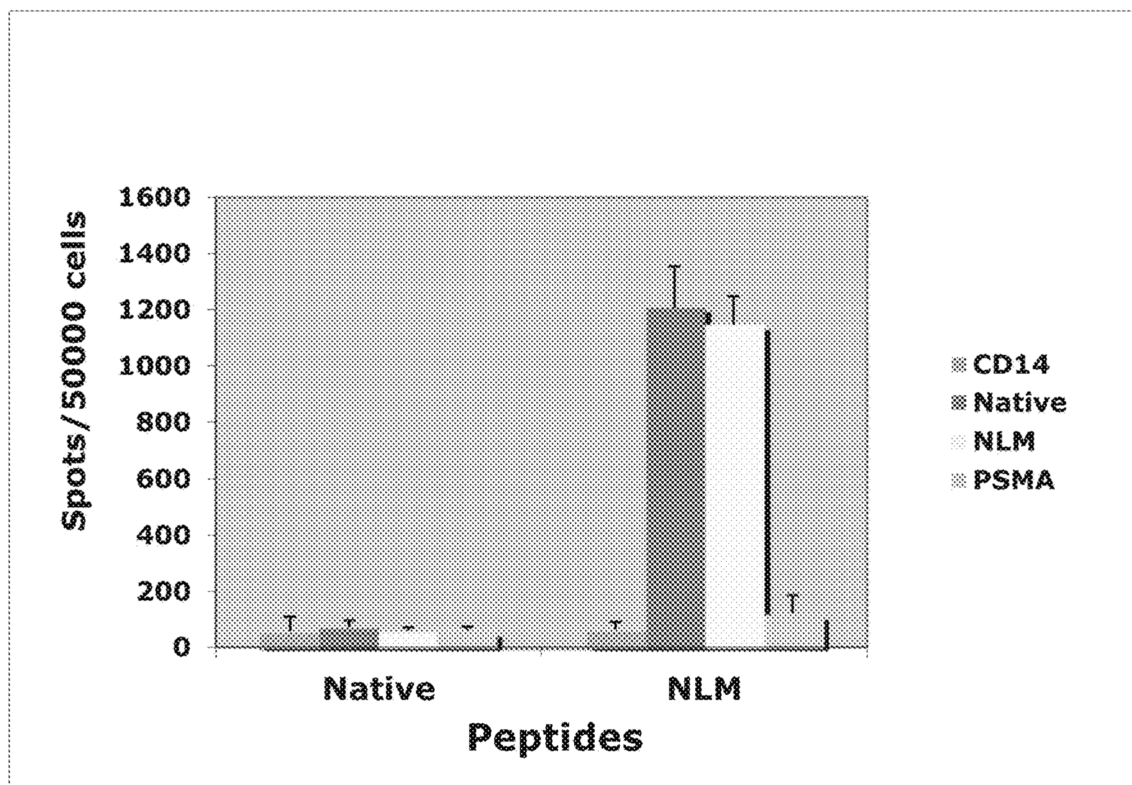
Figure 3:
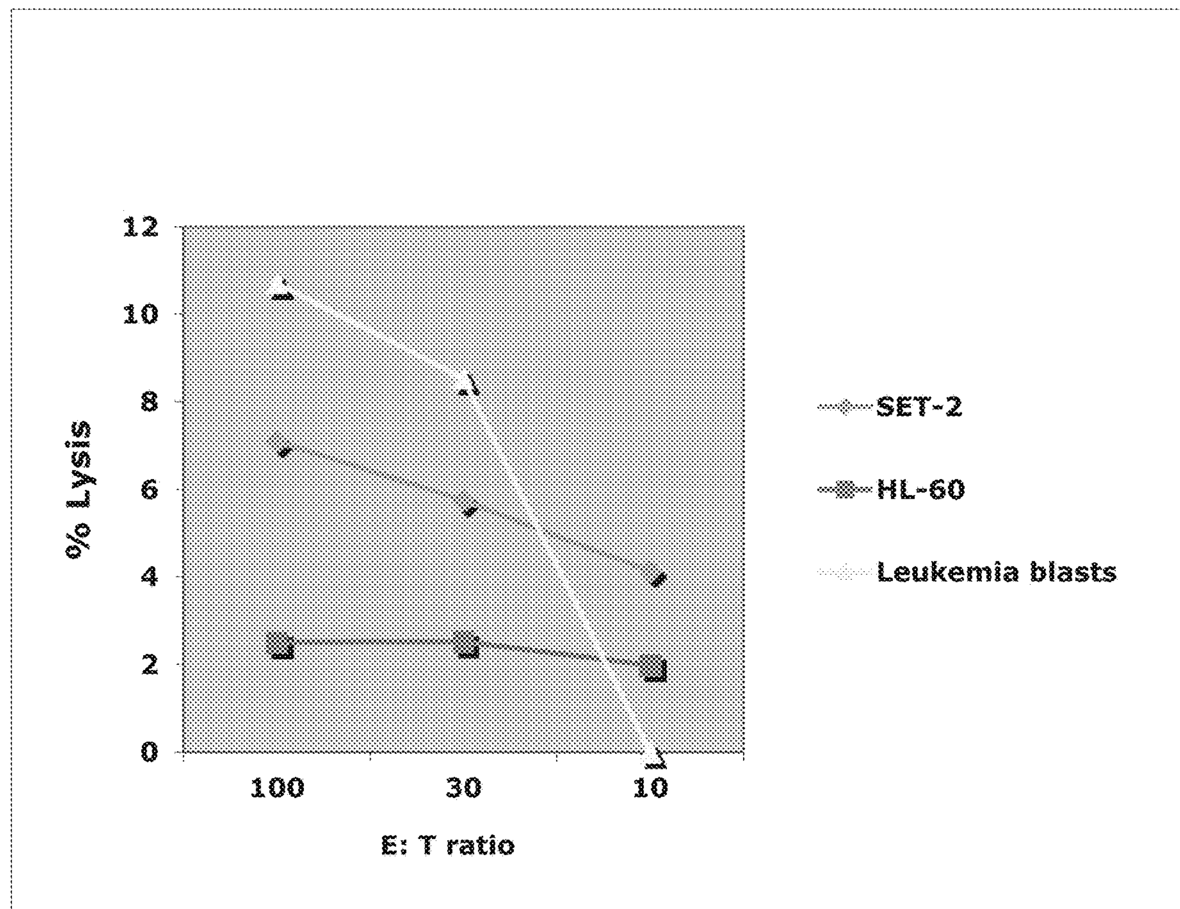
FIG. 3 shows that NLMNLGATL peptide induces cytotoxicity of T cells against WT1+HLA-A0201+ leukemia cells. The T cells from an HLA-A0201 positive donor were stimulated with NLMNLGATL peptide for 5 rounds. The cytotoxicity of the cells were measured by 5 hr-$^{51}$Cr release assay against AML cell line SET-2 (WT1+, HLA-A0201+), HL-60 (WT1+, HLA-A0201−) or primary leukemia blasts from a HLA-A2 positive patient. Each data point represents average+/−SD from triplicate cultures.
Figure 4A:
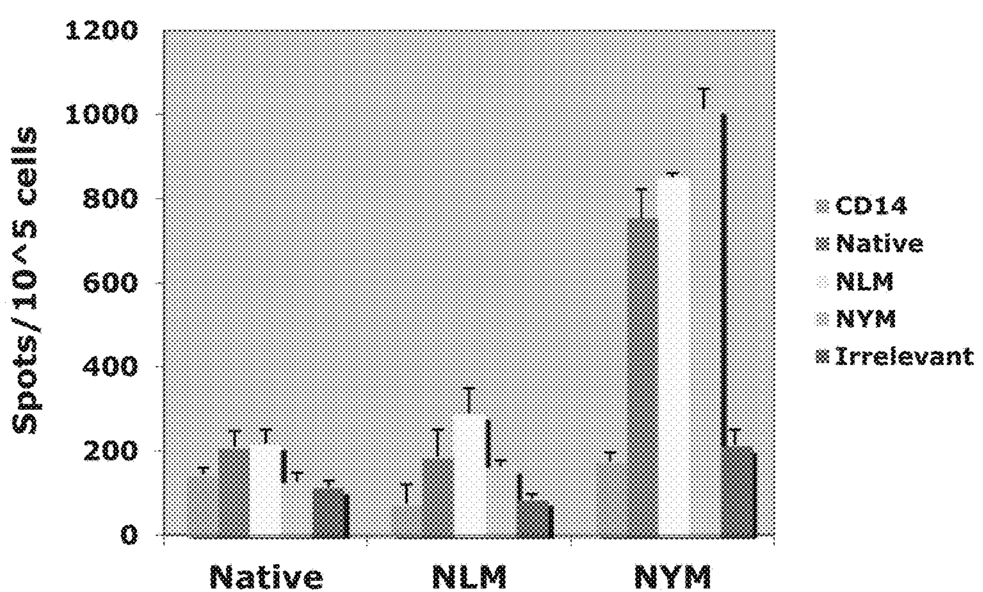
FIG. 4 A-B show peptide-specific T cell response in HLA-A2402 donor. CD3 T cells from a healthy HLA-A2402 homozygous donor was stimulated with NQMNLGATL, NLMNLGATL or NYMNLGATL peptides for 3 (A) or 5 (B) rounds. For each peptide, the bars represent, from left to right, CD14, Native peptide, NLMNLGATL, and irrelevant peptide, respectively. The peptide-specific response was measured by the IFN-g secretion upon challenged with individual peptide. Each data point represents average+/−SD from triplicate cultures.
Figure 4B:
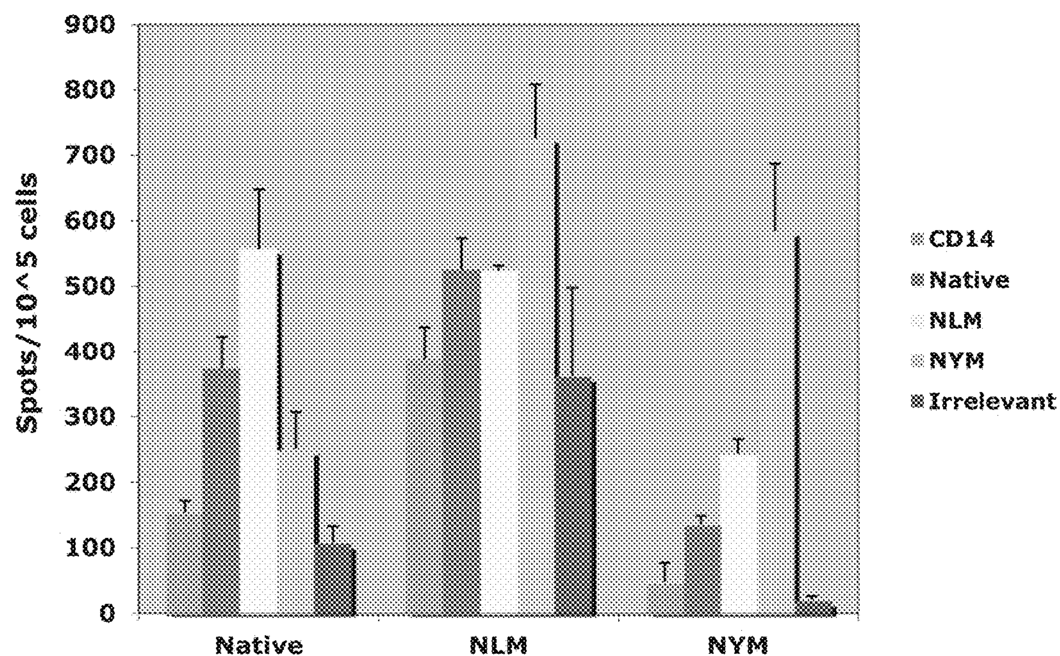

The immunogenicity of MHC class I-restricted peptides requires the capacity to bind and stabilize MHC class I molecules on the live cell surface. Moreover, the computer prediction has only up to 70% accuracy; therefore, direct measurement was sought of the strength of the interaction between the peptides and the HLA-A0201 molecules using a conventional binding and stabilization assay that uses the antigen-transporting-deficient (TAP2 negative) HLA-A0201 human T2 cells. T2 cells lack TAP function and consequently are defective in properly loading class I molecules with antigenic peptides generated in the cytosol. The association of exogenously added peptides with thermolabile, empty HLA-A0201 molecules stabilizes them and results in induced strong IFN-g secretion which crossed reacted with the native NQMNLGATL peptide. Five stimulations of T cells enhanced the response showing by more IFN-g spots (FIG. 2B) than 3 stimulation (FIG. 2A). T cells after 5 stimulation with NLMNLGATL peptide were also tested for the cytotoxicity using $^{51}$Cr release assay. No killing was observed against HL-60 cells that were WT1 positive but HLA-A2 negative. However, the T cells killed the WT1+ and HLA-A0201+ AML cell line SET-2 and primary leukemia blasts derived from a patient who is HLA-A0201 positive (FIG. 3). Whether both NLMNLGATL and NYMNLGATL heteroclitic peptides could induce a better CD8 T cell responses in HLA-A2402 donors was determined. NLMNLGATL peptide could induce T cell responses against both NLMNLGATL and the native NQMNLGATL peptides, but there was no significant enhancement compared to the T cell response induced by the native NQMNLGATL peptide. In the contrast, NYMNLGATL peptide induced a strong T cell response against itself and the native peptide after 3 stimulation (FIG. 4A) but the response was demised after 5 round stimulation (FIG. 4B), which also showed a weak cross reactivity with native sequence. These data demonstrated that NLMNLGATL heteroclitic peptide is a strong epitope for CD8 T cells in the context of HLA-A0201 molecule. NYMNLGATL peptide, on the other hand, induced CD8 T cell response in HLA-A0201 positive donors, but the response was not significantly better than the NQMNLGATL peptide.

Example 5. Induction of T Cell Response by HLA-DR.B1 Peptides that Recognizes NQMNLGATL CD8 T Cell Epitope It has been shown that a peptide combining both CD4 and CD8 epitopes is more effective than the single class I epitope in eliciting effective immune response for vaccine design, because CD4 T cells can help CD8 CTL by fully activating DCs through the CD40/CD40L signaling as well as by producing IL-2 and IFN-g. In addition, if T cells stimulated with longer peptides, in which CD8 T cell epitopes are imbedded in, could recognize the short peptides, it would confirm the processing of the CD8 T cell epitopes. Therefore, four HLA-DR.B1-binding peptides that span the NQMNLGATL and NLMNLGATL epitopes, respectively, were designed:

```
                         (SEQ ID NO: 8)
DR-Native-1: cmtwNQMNLGATLkg

                         (SEQ ID NO: 9)
DR-Native-2: wNQMNLGATLkgvaa

                        (SEQ ID NO: 14)
DR-het-1: cmtwNLMNLGATLkg

                        (SEQ ID NO: 17)
DR-het-2: wNLMNLGATLkgvaa
```

Since there is no definitive method to predict the class II peptide cleavage, two different versions of the class II peptides were designed using the BIMAS, SYFPEITHI and RANKPEP algorithms (Table 2).

TABLE 2

Predictive binding scores of HLA-DRB binding peptides.

| SYFPEITHI | DR.B1-0101 | DR.B1-0301 | DR.B1-0401 | DR.B1-0701 | DR.B1-1101 | DR.B1-1501 |
|---|---|---|---|---|---|---|
| Native-1 | | | | | | |
| DR-Native 1 cmtwNQMNLGATLkg SEQ ID NO: 8 | 17 | 1 | 16 | 10 | 16 | 4 |
| Het-1 | | | | | | |
| DR-het-1 cmtwNLMNLGATLkg SEQ ID NO: 14 | 18 | 2 | 16 | 10 | 16 | 4 |
| Native-2 | | | | | | |
| DR-Native-2 wNQMNLGATLkgvaa SEQ ID NO: 9 | 17 | 13 | 14 | 16 | 13 | 24 |
| Het-2 | | | | | | |
| DR-het-2 wNLMNLGATLkgvaa SEQ ID NO: 17 | 17 | 13 | 14 | 16 | 13 | 24 |

Figure 5A:
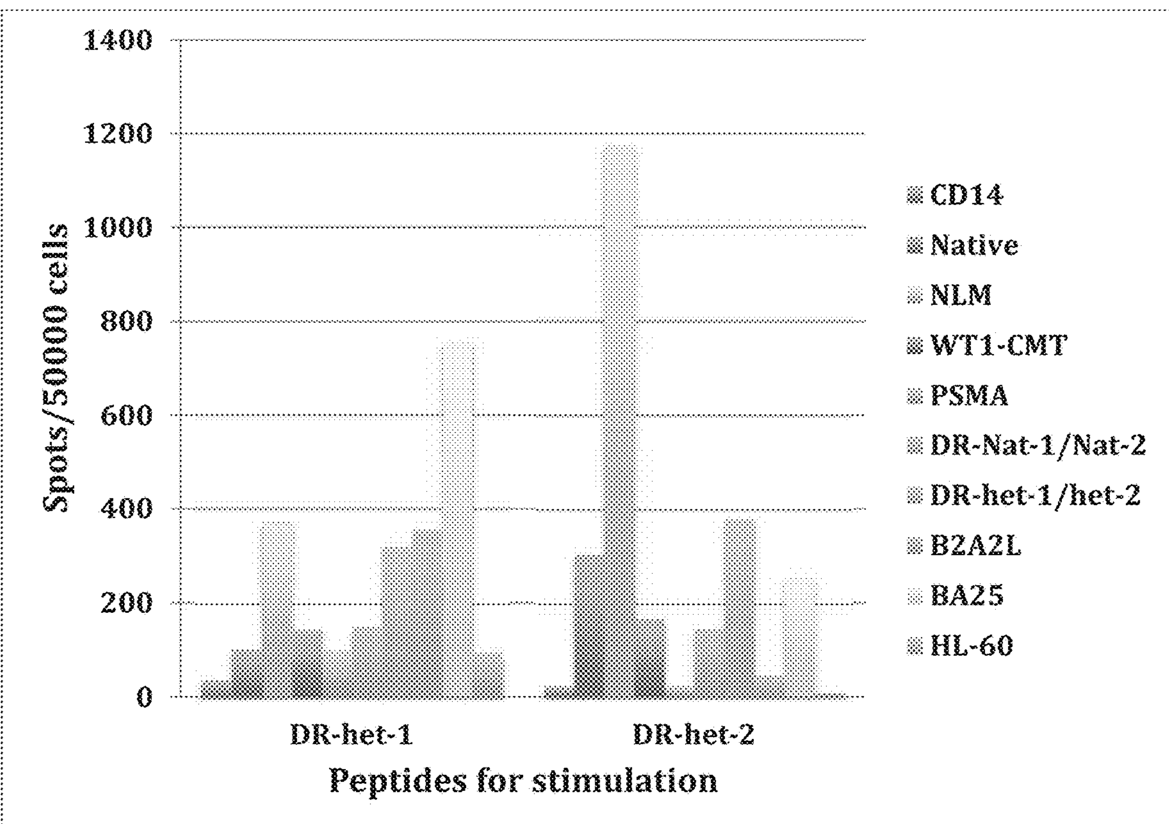
FIG. 5 A-B show HLA-DR.B1 peptide-specific T cell responses. (A). CD3 T cells were stimulated with DR-het-1 or DR-het-2 peptide for 5 rounds and the epitope-specific response was measured by IFN-g Elispot assay. For each peptide, the bars represent, from left to right, CD14, Native peptide, NLMNLGATL, WT1-CMT, PSMA, DR-Nat-1/Nat-2, DR-het-1/het-2, B2A2L, BA25 and HL-60, respectively. (B). CD3 T cells were stimulated with short peptides NQMNLGATL, NLMNLGATL and long peptides DR-native-1, DR-native-2, DR-het-1 or DR-het-2 peptide for 5 rounds and the cytotoxicity was measured by $^{51}$Cr-release assay, against Leukemia cell line BA-25 (HLA-A2+/A24+, WT1+) and the control HL-60 cells. Each data point represents average+/−SD from triplicate cultures.
Figure 5B:
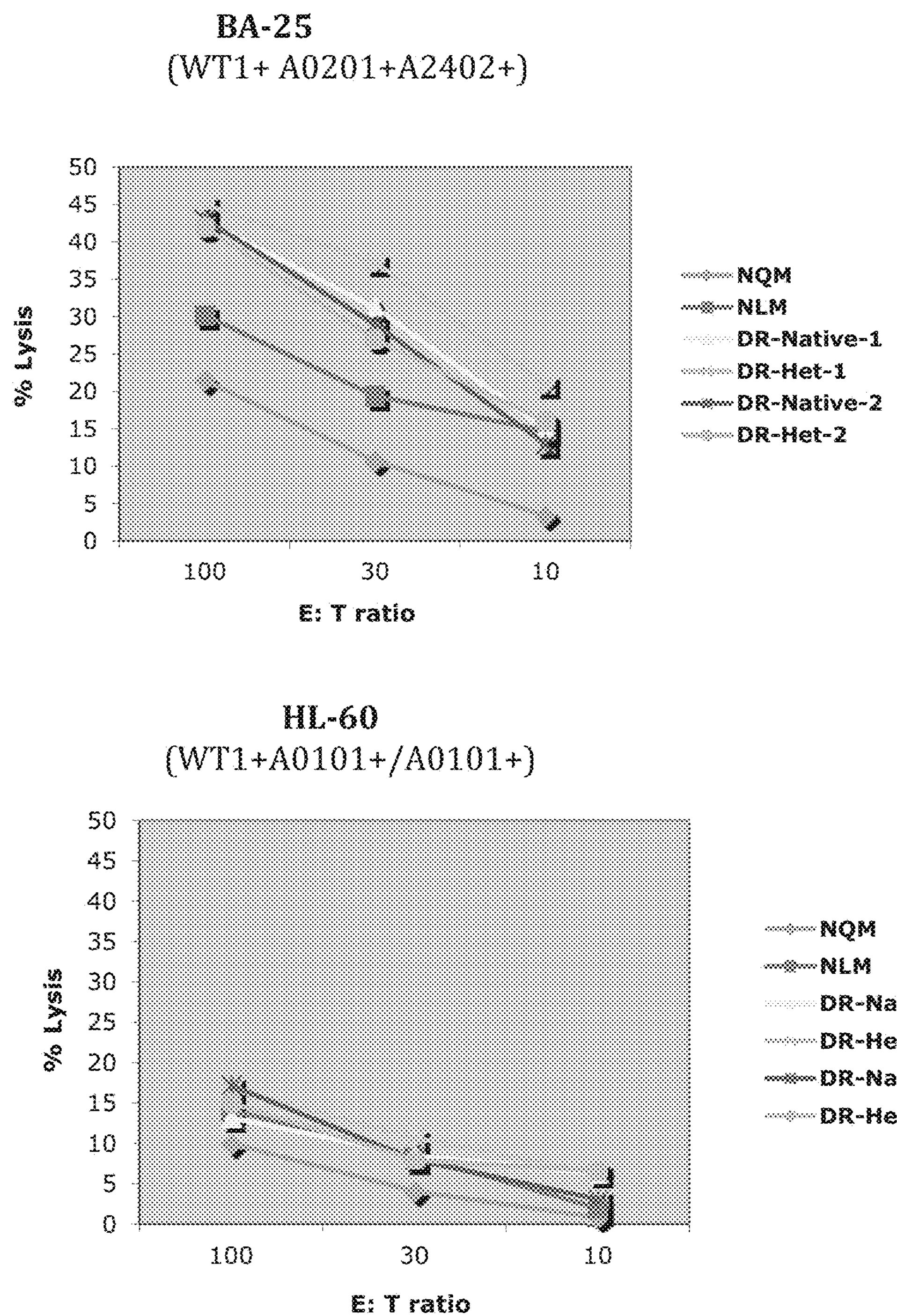

When T cells were stimulated with two "heteroclitic" DR.B1 peptides spanning the NLMNLGATL epitope, they induced T cell responses that were specific for both short and long peptides, showing by IFN-g secretion. Since CD4 peptides induce more potent response due to their massive production of cytokines, the background is usually higher than CD8 T cell peptide stimulation. Therefore, although both DR-heteroclitic peptides induced specific responses, DR-het-2 peptide showed a more clear response than the DR-het-1 peptide in a donor shown in FIG. 5A. It was evident that DR-het-2 peptide induced responses were specific for both short peptides NQMNGATL and NLMNGATL, and DR-native 2 and het-2 peptides. More importantly, the responses were directed against irradiated tumor cell line BA-25 (WT1+A2+), but not for the HL-60 cells that were WT1+ but A0201 negative. Similarly, when T cells were stimulated with short peptides (NQMNLGATL or NLMNGATL) or long peptides as indicated in FIG. 5B, only BA-25 but not HL-60 cells were killed.

Example 6. Other HLA-DR.B1 Binding Peptides that Recognize NQMNLGATL CD8 T Cell Epitope In addition to those DR peptides described above, additional HLA-DR.B1-binding peptides that span the NQMNLGATL, NLMNLGATL and NLMNLGATL epitopes were designed and evaluated (Table 3):

TABLE 3

| Predictive binding scores of the peptides to HLA-DR.B1 SYFPEITHI | | | | | | |
|---|---|---|---|---|---|---|
| | DR.B1-0101 | DR.B1-0301 | DR.B1-0401 | DR.B1-0701 | DR.B1-1101 | DR.B1-1501 |
| Native | | | | | | |
| cmtwNQMNLGATLkg (SEQ ID NO: 8) | 17 | 1 | 16 | 10 | 16 | 4 |
| mtwNQMNLGATLkgv (SEQ ID NO: 12) | 17 | 11 | 6 | 8 | 0 | 8 |
| twNQMNLGATLkgva (SEQ ID NO: 13) | 18 | 2 | 12 | 0 | 7 | 8 |
| wNQMNLGATLkgvaa (SEQ ID NO: 9) | 17 | 13 | 14 | 16 | 13 | 24 |
| Het24-1 | | | | | | |
| cmtwNLMNLGATLkg (SEQ ID NO: 14) | 18 | 2 | 16 | 10 | 16 | 4 |
| mtwNLMNLGATLkgv (SEQ ID NO: 15) | 17 | 13 | 6 | 8 | 0 | 8 |
| twNLMNLGATLkgva (SEQ ID NO: 16) | 26 | 12 | 20 | 8 | 13 | 18 |
| wNLMNLGATLkgvaa (SEQ ID NO: 17) | 17 | 13 | 14 | 16 | 13 | 24 |
| Het24-2 | | | | | | |
| cmtwNYMNLGATLkg (SEQ ID NO: 10) | 17 | 1 | 16 | 10 | 16 | 4 |
| mtwNYMNLGATLkgv (SEQ ID NO: 19) | 17 | 11 | 6 | 8 | 0 | 8 |
| twNYMNLGATLkgva (SEQ ID NO: 20) | 28 | 2 | 22 | 10 | 17 | 8 |
| wNYMNLGATLkgvaa (SEQ ID NO: 11) | 17 | 13 | 14 | 16 | 13 | 24 |
| RANKPEP | DR.B1-0101 | DR.B1-0301 | DR.B1-0401 | DR.B1-0701 | DR.B1-1101 | DR.B1-1501 |
| cmtwNQMNLGATLkgva Native (SEQ ID NO:21) | 10.188; 21.12% Binder: wNQMN LGAT (CMT-LKG-15aa) (SEQ ID NO: 24) | 3.577; 8.78% | 13.521; 30.67% Binder: twNQM NLGA (CM-TLK-14aa) (SEQ ID NO: 26) | 7.85; 15.27% | 21.138; 32.2% Binder: mtwNQ MNLG (C-ATL-13aa) (SEQ ID NO: 28) | 1.731; 4.14% |

TABLE 3-continued

| Predictive binding scores of the peptides to HLA-DR.B1 SYFPEITHI | | | | | | |
|---|---|---|---|---|---|---|
| cmtwNLMNLGATLkgva Het24-1 (SEQ ID NO: 22) | 9.377; 1 9.44% Binder: wNLMN LGAT (CMT-LKG-15aa) (SEQ ID NO: 25) | 2.728; 6.7% | 11.145; 25.28% Binder: MNLGA TLkg (WNL-VA-14aa) (SEQ ID NO: 27) | 7.85; 15.27% | 22.089; 33.65% Binder: mtwNQ MNLG (C-ATL-13aa) (SEQ ID NO:28) | 6.209; 14.84% |
| cmtwNYMNLGATLkgva Het24-2 (SEQ ID NO: 23) | 7.184; 14.89% | 4.061; 9.97% | 11.145; 25.28% Binder: MNLGA TLkg (WNY-VA-14aa) (SEQ ID NO: 18) | 7.85; 15.27% | 18.539; 28.23% Binder: mtwNQ MNLG (C-ATL-13aa) (SEQ ID NO: 28) | 8.439; 20.17% |

Figure 6:
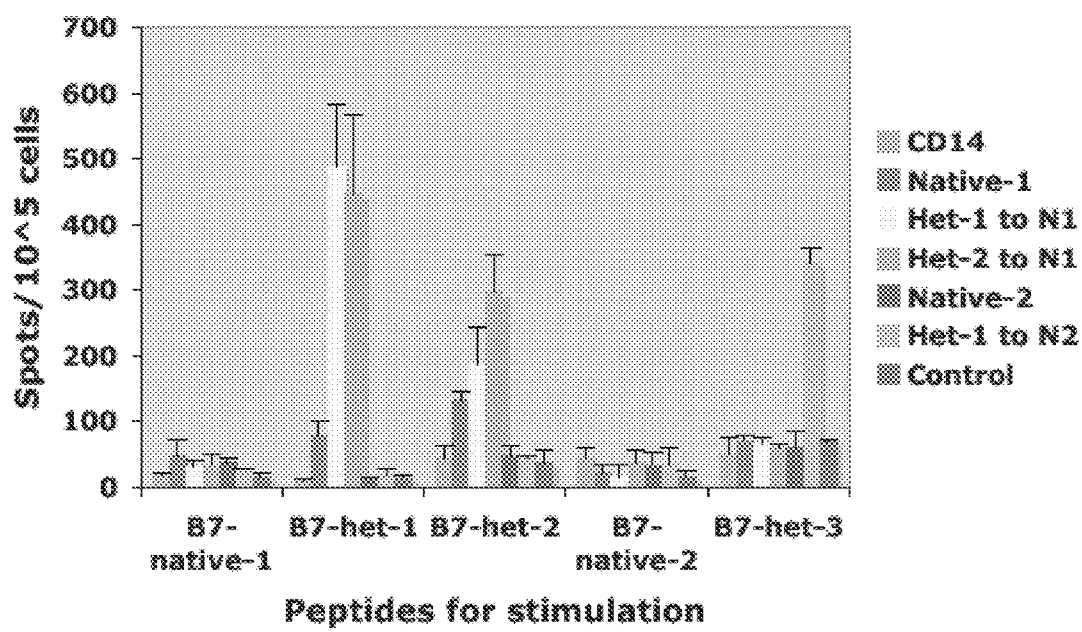
FIG. 6 depicts CD3 T cells from a HLA-B0702-positive donor were stimulated with 2 sets of peptides (total five) for 5 times in vitro. The peptide-specific response was measured by IFN-gamma ELISPOT assay, against individual peptide; peptides tested from left to right are SEQ ID NOS:34, 37, 38, 30 and 31; and for each peptide, the bars represent, from left to right, responses to CD14, Native-1 peptide, Het-1 to Native-1, Het-2 to Native-1, Native-2, Het-1 to Native-2 and control, respectively.

Example 7. Generation of Peptides Derived from WTI Oncoprotein that Bind to Human HLA-B7 Class I and HLA-Dr Class II Molecules Peptides were also designed that that bind to HLA-B0702 (Table 4). The following peptide sequences were designed: RQRPHPGAL (B7-Native 1; SEQ ID NO:34), RLRPHPGAL (B7-het-1; SEQ ID NO:37), RIRPHPGAL (B7-het-2; SEQ ID NO:38), GALRNPTAC (Native 2; SEQ ID NO:29), and GALRNPTAL (B7-het-3; SEQ ID NO:31). The predictive binding scores of these and other variants are shown in Table 4. These peptides were tested in vitro and stimulate heteroclitic T cell responses (FIG. 6). CD3 T cells from a HLA-B0702-positive donor were stimulated with 2 sets of peptides (total five) for 5 times in vitro. The peptide-specific response was measured by IFN-gamma ELISPOT assay, against individual peptide.

For the first set of peptides, both heteroclitic-1 and 2, induced the peptide-specific responses, but the cross reactivity to the native 1 (N1) peptide was stronger for the het-2 than the het-1 peptide. For the second set of the peptides, heteroclitic peptide induced strong IFN-g production, when challenged with the stimulating peptide, but no cross-reactivity to the native sequence was found.

TABLE 4

Predictive binding scores of B7 peptides to HLA-B7 and other haplotypes.

| | RANKPEP B0702 Score; | % Opt | SYFPEITHI-B0702 | SYFPEITHI-A0201 | SYFPEITHI-A0301 | SYFPEITHI-A0101 | SYFPEITHI-B-08 | SYFPEITHI-B-2705 | SYFPEITHI-B-3902 |
|---|---|---|---|---|---|---|---|---|---|
| 1. GALRNPTAC (p -118 to -110) SEQ ID NO: 29 | -18.084 | -44.75% | 2 | | | | | | 14 (B5101) |
| GYLRNPTAC SEQ ID NO: 30 | -20.632 | -51.06% | | | | All below 8 | | | |
| GALRNPTAL SEQ ID NO: 31 | -9.401 | -23.27% | 12 | 18 | 8 | | 16 | 17 | 20 (B5101) |
| YALRNPTAC SEQ ID NO: 32 | -14.528 | -35.95% | 10 | | | All below 10 | | | |
| GLLRNPTAC SEQ ID NO: 33 | -20.18 | -49.94% | 2 | 14 | 18 | | | | 14 |
| 2. RQRPHPGAL (p -125 to -117) SEQ ID NO: 34 | -3.687 | -9.12% | 15 | 13 | 13 | | 17 | 14 (1501) | 23 |
| RYRPHPGAL SEQ ID NO: 35 | -4.517 | -11.18% | 15 | 13 | 13 | | 17 | | |

TABLE 4-continued

| Predictive binding scores of B7 peptides to HLA-B7 and other haplotypes. | | | | | | | | |
|---|---|---|---|---|---|---|---|---|
| YQRPHPGAL<br>SEQ ID NO: 36 | −5.618 | −13.90% | | 15 | | | | |
| RLRPHPGAL<br>SEQ ID NO: 37 | −4.065 | −10.06% | 15 | 23 | 23 | | 23 | 17<br>(B37) |
| RIRPHPGAL<br>SEQ ID NO: 38 | −2.674 | −6.62% | 15 | 21 | 21 | | 21 | |
| | BIMAS-B7 | | | | | | | |
| GALRNPTAC<br>SEQ ID NO: 30 | 0.3 | | | | | | | |
| GALRNPTAL<br>SEQ ID NO: 31 | 12 | | | | | | | |
| RQRPHPGAL<br>SEQ ID NO: 34 | 40 | | | | | | | |
| RLRPHPGAL<br>SEQ ID NO: 37 | 40 | | | | | | | |
| RIRPHPGAL<br>SEQ ID NO: 38 | 40 | | | | | | | |

Based in the finding that the native peptides RQRPHPGAL (p-125 to -117; SEQ ID NO:34) and GALRNPTAC (p-118 to -110; SEQ ID NO:29) induce T cells responses in the context of HLA-B7 molecule, using HLA-binding prediction algorithms, one heteroclitic peptide for the GALRNPTAC peptide was designed (SEQ ID NO:31), and two heteroclitic peptides for RQRPHPGAL (SEQ ID NOS: 37 and 38). Based on the binding prediction, these peptides may also be able to stimulate T cells in the context of other HLA haplotypes, such as: A0201, A0301, B8, B1501, B37 and B5101 (Table 4).

Example 8. Generation of Peptides Derived from WTI Oncoprotein that Bind to Human HLA-B35, A0101, A0301, A1101 Class I and HLA-DR Class II Molecules Peptide QFPNHSFKHEDPMGQ (p170-182) (SEQ ID NO:39) induces T cells response in the context of HLA-DR.B1 0301 and 0401. The short sequences imbedded within the long peptide, HSFKHEDPM, induces T cell response in the context of B3501. Based on the predictions by the HLA-binding prediction algorithms, one heteroclitic long peptide was designed, which is the extension of the het-B35-1 short peptide.

The sequences of the peptides are: Class II peptide: DR.B1-03/04-Native: QFPNHSFKHEDPM (SEQ ID NO:42), DR.B1-03/04-Het: QFPNHSFKHEDPY (SEQ ID NO:43; Class I peptides: 1. Native: HSFKHEDPM (SEQ ID NO:40), 2. Het-01/03-1: HSFKHEDPY (for A0101 and A0301) (SEQ ID NO:41), and 3. Het-03/11-1 HSFKHEDPK (for A0301 and A1101) (SEQ ID NO:42). Heteroclitic peptides for the HLA-B3501 haplotype were tested in silico (Table 5).

TABLE 5

Predictive binding scores of the natural peptides to HLA-DR.B1-0301, 0402 and B3501, A0101, A0301 and A1101.

| Class II<br>SYFPEITHI (15 mer) | DR.B1-<br>0101 | DR.B1-<br>0301 | DR.B1-<br>0401 | DR.B1-<br>0701 | DR.B1-<br>1101 | DR.B1-<br>1501 |
|---|---|---|---|---|---|---|
| QFPNHSFKHEDPMGQ<br>SEQ ID NO: 39 | 8 | 2 | 12 | 0 | 14 | 14 |
| RANKPEP | | | | | | |
| QFPNHSFKHEDPMGQ<br>SEQ ID NO: 39 | −1.949;<br>−4.04% | −2.786;<br>−6.84% | 6.717; 15.23%<br>(0401)<br>6.165; 13.82%<br>(0402) | −4.04;<br>−8.56% | 3.393;<br>5.17% | 8.864;<br>21.18% |

TABLE 5-continued

| Predictive binding scores of the natural peptides to HLA-DR.B1-0301, 0402 and B3501, A0101, A0301 and A1101. | | | |
|---|---|---|---|
| Class I | SYFPEITHI | BIMAS | RANKPEP |
| HSFKHEDPM (B35-native) SEQ ID NO: 40 | | | |
| B3501 | N/A | 10 | -3.568; -8.95% |
| A0101 | 4 | 0.002 | -16.2; -26.61% |
| A0301 | 0 | 0.005 | -3.832; -10.86% |
| A1101 | 11 | 0 | -12.047; -30.69% |
| HSFKHEDPY (B35-het1) SEQ ID NO: 41 | | | |
| B3501 | N/A | 10 | -2.86; -7.18% Cleaved |
| A0101 | 19 | 0.075 | -5.164; -8.48% Cleaved |
| A0301 | 6 | 0.1 | 7.127; 20.20% Cleaved |
| A1101 | 11 | 0 | 0.433; 1.1% Cleaved |
| HSFKHEDPK (B35-het-2) SEQ ID NO: 42 | | | |
| B3501 | N/A | 0.05 | -11.223; -28.16% |
| A0101 | 4 | 0.03 | -15.83; -26% |
| A0301 | 10 | 0.5 | -8.783; 24.77% |
| A1101 | 21 | 0.04 | 4.316; 11% |

Example 9. Generation of Peptides Derived from WT1 Oncoprotein that Bind to Human HLA-A1, A3, A11 Class I and HLA-DR.B1-0401 Class II Molecules Peptide KRPFMCAYPGCNK (320-332) (SEQ ID NO:44) was shown to induce T cell response in the context of HLA-DR.B1 0401. The short sequence imbedded within the long peptide, FMCAYPGCN (SEQ ID NO:45), induces T cell response in the context of B35, B7 and A0101 (Table 6). The binding scores were investigated of the peptides to multiple HLA haplotypes using prediction algorithms. One heteroclitic long peptide was designed, which is the extension of the het-1 short peptide. Two short heteroclitic peptides were designed that bind better to HLA-A0101, 0301 and 1101. The sequences of the peptides are: Class II peptide: DR.B1-04 Native: KRPFMCAYPGCNK (SEQ ID NO:44), DR.B1-04 het: KRPFMCAYPGCYK (SEQ ID NO:46); Class I peptides: 1. Native: FMCAYPGCN (SEQ ID NO:45), 2. DR.B1-04-Het-1 short: FMCAYPGCY (for A0101) (SEQ ID NO:47), 3. DR.B1-04-Het-2-short: FMCAYPGCK (for A0301 and A1101) (SEQ ID NO:48). KRPFMCAYPGCYK (SEQ ID NO:46) is the extension of DR.B1-04-het 1 short, FMCAYPGCN (SEQ ID NO:45), in which the end of the sequences CN becomes CY.

TABLE 6

| Predictive binding scores of the peptides to HLA-DR.B1-0401 and B35, B7, A0101, A0301 and A1101. | | | | | | |
|---|---|---|---|---|---|---|
| HLA-DR.B1 SYFPEITHI (15 mer) | DR.B1-0101 | 0301 | 0401 | 0701 | 1101 | 1501 |
| KRPFMCAYPGCNKRY SEQ ID NO: 49 | 16 | 8 | 22 | 16 | 10 | 16 |
| KRPFMCAYPGCYKRY SEQ ID NO: 55 | 16 | 16 | 16 | 22 | 10 | 12 |
| SEKRPFMCAYPGCNK SEQ ID NO: 50 | 15 | 0 | 0 | 0 | 12 | 8 |

TABLE 6-continued

| Predictive binding scores of the peptides to HLA-DR.B1-0401 and B35, B7, A0101, A0301 and A1101. | | | | | | |
|---|---|---|---|---|---|---|
| RANKPEP | | | | | | |
| KRPFMCAYPGCNK SEQ ID NO: 44 | 5.381; 11.15% | -9.13; -22.35% | 3.131; 7.1% | -0.486; -0.95% | 0.756; 1.15% | 4.199; 10.04% |
| Class I | SYFPEITHI | BIMAS | RANKPEP | | | |
| FMCAYPGCN (native) SEQ ID NO: 45 | | | | | | |
| A0101 | 0 | 0.005 | -4.165; -6.84% | | | |
| B7 | 1 | 0.02 | -21.654; 53.59% | | | |
| B35 | N/A | N/A | -23.926; -60.03% | | | |
| A0301 | 4 | 0.018 | -2.503; -7.09% | | | |
| A1101 | 8 | 0 | -2.509; 5.25% | | | |
| FMCAYPGCY (DR.B1-04-het1-short) SEQ ID NO: 47 | | | | | | |
| A0101 | 15 | 0.25 | 6.613; 10.86% Cleaved | | | |
| B7 | 1 | 0.02 | -13.887; 34.37%, cleaved | | | |
| B35 | N/A | 0.02 | -11.078; 27.8% | | | |
| A0301 | 10 | 3.6 | 7.557; 21.42%, cleaved | | | |
| A1101 | 8 | 0.004 | 9.516; 24.24%, cleaved | | | |
| FMCAYPGCK (DR.B1-04-Het-2 short) SEQ ID NO: 48 | | | | | | |
| A0101 | 0 | 0.1 | 4.053; -6.66% | | | |
| B7 | 1 | 0.01 | -20.85, 51.71% | | | |
| B35 | N/A | 0.01 | -21.886; 47.27% | | | |
| A0301 | 14 | 18 | 9.168; 25.99% | | | |
| A1101 | 18 | 0.4 | 8.883; 22.09% | | | |

Example 10. Additional Cross-Reactivity Studies

Figure 7:
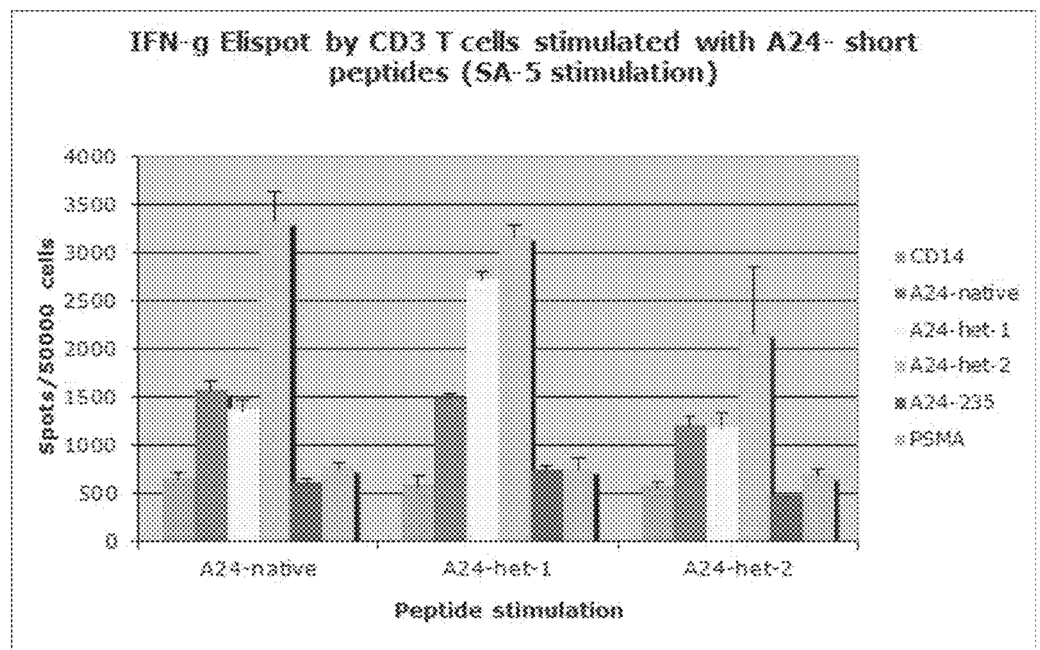
FIG. 7 depicts the results of an ELISPOT assay using donor SA (5 stimulations) for the Het-1 (SEQ ID NO:6) and Het-2 (SEQ ID NO:7) A24 peptide, in comparison to the native sequence (SEQ ID NO:5). For each peptide, the bars represent, from left to right, CD14, A24-native peptide, A24-het-1, A24-het-2, A24-235, and PSMA, respectively. The heteroclitic peptides generate cross-reactive responses.

An ELISPOT assay was conducted using donor SA after 5 stimulations for the Het24-1 (SEQ ID NO:6) and Het24-2 (SEQ ID NO:7) A24 peptides, in comparison to the native sequence (SEQ ID NO:5). As shown in FIG. 7, the heteroclitic peptides generate cross-reactive responses.

What is claimed is:

1. An isolated peptide comprising the amino acid sequence NYMNLGATL (SEQ ID NO:7) other than the isolated peptide consisting of the amino acid sequence NYMNLGATL (SEQ ID NO:7).

2. The isolated peptide of claim 1, comprising the amino acid sequence selected from the group consisting of CMTWNYMNLGATLKG (SEQ ID NO: 10), WNYMNLGATLKGVAA (SEQ ID NO:11), MTWNYMNLGATLKGV (SEQ ID NO:19), TWNYMNLGATLKGVA (SEQ ID NO:20), and CMTWNYMNLGATLKGVA (SEQ ID NO:23).

3. The isolated peptide of claim 1, wherein said isolated peptide binds to an HLA class I molecule, an HLA class II molecule, or the combination thereof.

4. A pharmaceutical composition comprising the isolated peptide of claim 1 and a pharmaceutically acceptable carrier, vehicle or excipient.

5. A vaccine comprising (a) at least one said isolated peptide of claim 1, and (b) an adjuvant or a carrier.

6. The vaccine of claim 5, wherein said adjuvant is QS21, Freund's incomplete adjuvant, aluminum phosphate, aluminum hydroxide, BCG, alum, a growth factor, a cytokine, a chemokine, an interleukin, Montanide ISA 51, or GM-CSF.

7. A method of treating a subject with a WT1-expressing cancer or reducing an incidence of a WT1-expressing cancer, or its relapse, the method comprising administering to the subject in need thereof the vaccine of claim 5.

8. The method of claim 7, wherein said WT1-expressing cancer is a leukemia, a desmoplastic small round cell tumor, a gastric cancer, a colon cancer, a lung cancer, a breast cancer, a germ cell tumor, an ovarian cancer, a uterine cancer, a thyroid cancer, a liver cancer, a renal cancer, a Kaposi's sarcoma, a sarcoma, a hepatocellular carcinoma, a Wilms' tumor, an acute myelogenous leukemia (AML), a myelodysplastic syndrome (MDS), mesothelioma, or a non-small cell lung cancer (NSCLC).

9. A method of inducing formation and proliferation of CTL specific for cells of a WT1-expressing cancer in a subject in need thereof, the method comprising administering to said subject the vaccine of claim 5.

10. The method of claim 9, wherein said WT1-expressing cancer is a leukemia, a desmoplastic small round cell tumor, a gastric cancer, a colon cancer, a lung cancer, a breast cancer, a germ cell tumor, an ovarian cancer, a uterine cancer, a thyroid cancer, a liver cancer, a renal cancer, a Kaposi's sarcoma, a sarcoma, a hepatocellular carcinoma, a Wilms' tumor, an acute myelogenous leukemia (AML), a myelodysplastic syndrome (MDS), mesothelioma, or a non-small cell lung cancer (NSCLC).

11. A composition comprising (a) an antigen-presenting cell and (b) the isolated peptide of claim 1.

12. The isolated peptide of claim 1 consisting of the amino acid sequence WNYMNLGATLKGVAA (SEQ ID NO:11).

13. A nucleic acid molecule encoding a peptide comprising the isolated peptide of claim 1.

14. A vector comprising the nucleic acid molecule of claim 13.

15. The vector of claim 14, wherein the vector further encodes an immunomodulatory compound.

16. A pharmaceutical composition comprising the nucleic acid of claim 13 or a vector thereof.

17. A method of treating a subject with a WT1-expressing cancer or reducing an incidence of a WT1-expressing cancer, or its relapse, the method comprising administering to said subject in need thereof the nucleic acid of claim 13 or a vector thereof.

18. The method of claim 17, wherein said WT1-expressing cancer is a leukemia, a desmoplastic small round cell tumor, a gastric cancer, a colon cancer, a lung cancer, a breast cancer, a germ cell tumor, an ovarian cancer, a uterine cancer, a thyroid cancer, a liver cancer, a renal cancer, a Kaposi's sarcoma, a sarcoma, a hepatocellular carcinoma, a Wilms' tumor, an acute myelogenous leukemia (AML), a myelodysplastic syndrome (MDS), mesothelioma or a non-small cell lung cancer (NSCLC).

19. An isolated class II binding peptide selected from the group consisting of CMTWNYMNLGATLKG (SEQ ID NO:10), WNYMNLGATLKGVAA (SEQ ID NO:11), MTWNYMNLGATLKGV (SEQ ID NO:19), TWNYMNLGATLKGVA (SEQ ID NO:20) and CMTWNYMNLGATLKGVA (SEQ ID NO:23).

20. An isolated class II binding peptide having the sequence WNYMNLGATLKGVAA (SEQ ID NO:11).

* * * * *